United States Patent [19]
Satow et al.

[11] Patent Number: 5,356,863
[45] Date of Patent: Oct. 18, 1994

[54] URACIL DERIVATIVES

[75] Inventors: Jun Satow, Funabashi; Kenzou Fukuda, Onoda; Kaoru Itoh, Funabashi; Hiroshi Kita, Funabashi; Yasuo Kawamura, Funabashi; Koichi Suzuki, Saitama; Tsutomu Nawamaki, Saitama; Shigeomi Watanabe, Saitama; Toshiharu Endo, Saitama; Kimihiro Ishikawa, Saitama, all of Japan

[73] Assignee: Nissan Chemical Industries, Ltd., Tokyo, Japan

[21] Appl. No.: 75,529

[22] PCT Filed: Dec. 16, 1991

[86] PCT No.: PCT/JP91/01716

§ 371 Date: Oct. 21, 1993

§ 102(e) Date: Oct. 21, 1993

[87] PCT Pub. No.: WO92/11244

PCT Pub. Date: Jul. 9, 1992

[30] Foreign Application Priority Data

Dec. 17, 1990 [JP] Japan ................ 2-402753
May 27, 1991 [JP] Japan ................ 3-121420
Nov. 15, 1991 [JP] Japan ................ 3-300341

[51] Int. Cl.$^5$ ............ A01N 43/80; A01N 47/02; A01N 47/04; A01N 47/20; C07D 239/54; C07D 239/56; C07D 401/10; C07D 403/10

[52] U.S. Cl. .................... 504/243; 504/221; 504/222; 504/225; 544/3; 544/8; 544/60; 544/123; 544/263; 544/295; 544/296; 544/310; 544/311; 544/312; 544/313; 544/314

[58] Field of Search ............ 544/310–314, 544/295, 296, 263, 3, 8, 60, 123; 504/243, 221, 222, 225, 243

[56] References Cited

U.S. PATENT DOCUMENTS

| | | | |
|---|---|---|---|
| 4,859,229 | 8/1989 | Wemper et al. | 544/309 |
| 4,941,909 | 7/1990 | Wemper et al. | 544/314 |
| 5,041,156 | 8/1991 | Suchy et al. | 544/309 |
| 5,084,084 | 1/1992 | Satow et al. | 504/243 |
| 5,116,404 | 5/1992 | Ishii et al. | 504/243 |
| 5,127,935 | 7/1992 | Satow et al. | 504/243 |
| 5,134,145 | 7/1992 | Brouwer et al. | 544/313 |
| 5,154,755 | 10/1992 | Satow et al. | 504/243 |
| 5,169,430 | 12/1992 | Strunk et al. | 544/314 |
| 5,183,492 | 2/1993 | Suchy et al. | 544/313 |

FOREIGN PATENT DOCUMENTS 221178 10/1986 Japan .
41466 2/1988 Japan .
107967 5/1988 Japan .

*Primary Examiner*—Cecilia Tsang
*Attorney, Agent, or Firm*—Oblon, Spivak, McClelland, Maier & Neustadt

[57] ABSTRACT

The present invention relates to an uracil derivative represented by the formula (1):

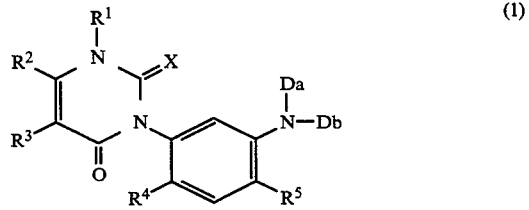

in which $R^1$ represents hydrogen, alkyl or haloalkyl; $R^2$ represents haloalkyl; $R^3$ represents hydrogen, alkyl, haloalkyl, hydroxymethyl, halogen or nitro; $R^4$ represents hydrogen or halogen; $R^5$ represents hydrogen, halogen, nitro or cyano; X represents oxygen or sulfur: provided that the case where both of Da and Db represent hydrogen is excluded and a herbicide containing the same. The compound can be safely applied to important crops and shows high effect against many weeds in a low amount.

6 Claims, No Drawings

URACIL DERIVATIVES

TECHNICAL FIELD

This invention relates to a novel uracil derivative and a selective herbicide containing the derivative as an effective ingredient.

PRIOR ARTS

Many herbicides have heretofore been practically used in order to protect sugar important crops such as rice, soybean, wheat, corn, cotton, sugar, beet, etc. from weeds and to enhance productivities of these important crops. These agents may be roughly classified into three classes depending on application loci, i.e. the agent for upland field, the agent for paddy field and the agent for non-cultivated field. Further, each class can be classified to a soil incorporation treatment type, a pre-emergence soil treatment type, a post-emergence treatment (foliar treatment) type, etc., depending on methods for application of the agents.

In recent years, accompanying with a worldwide increase in population, it is clear that the productivities of the important crops have influence to food economy in respective countries. Accompanying with these changes, it is unavoidable that the form of conventional agriculture will be changed toward the 21th century. Actually, to provide for persons engaged in agriculture a herbicide which can economically and efficiently kill or control the weeds which may be obstacles to crop cultivation becomes increasingly necessary than before.

Such a herbicide is required to have the following requirements:

(1) it has a high herbicidal effect with a low amount (particularly in view of environmental protection, it is necessary to kill the weeds in the application amount as low as possible);

(2) it has a suitable residual effect (in recent years, it has become a problem that the agent remaining in soil for a long period damages succeeding crops, thereby it is important to show the suitable residual effect after application);

(3) it promptly kills the weeds after application (after a short period from a chemical treatment, next crops can be seeded and transplanted).

(4) a frequency of its application is fewer (for a person engaged in agriculture, it is important to make the frequency of a complicated work for controlling the weeds as fewer as possible).

(5) its spectrum of controlling the weeds is wide (it is desirable that the agent is capable of controlling weed species of different characteristics such as broad leaf weeds, grassy weeds, perennial weeds, etc. with the single agent).

(6) it is applied according various methods (more potent herbicidal effects can be obtained by combining a soil treatment effect, a foliar treatment effect, etc.).

(7) it shows no damage which causes problems against the crops (the agent which can selectively kill only weeds is preferred in the cultivated field where the crops and the weeds mixedly exist).

On the other hand, it has been known that specific compounds of uracil derivative show herbicidal activities. For example, bromacil has been described in The Pesticide Manual, 8th Edition, p. 89, The British Crop Protection Council (1987), etc. as one of the herbicide having an uracil structure.

Further, it has also been known that the following aryl uracil derivatives have the herbicidal activities.

For example, the compound represented by the formula:

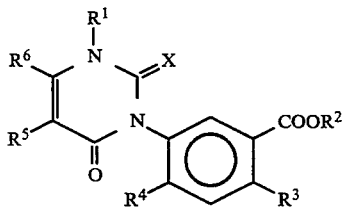

in which
$R^1$ represents hydrogen, $C_{1-4}$ alkyl, $C_{2-4}$ alkenyl, $C_{2-4}$ alkynyl, $C_{2-6}$ alkoxyalkyl, formyl, $C_{2-6}$ alkanoyl or $C_{2-6}$ alkoxycarbonyl;
$R^2$ represents hydrogen, $C_{1-6}$ alkyl, $C_{2-4}$ alkenyl, $C_{2-4}$ alkynyl or $C_{2-6}$ alkoxyalkyl,
$^3$ represents halogen or nitro,
$^4$ represents hydrogen or halogen,
$^5$ represents hydrogen, halogen, $C_{1-4}$ alkyl, chloromethyl, bromomethyl, hydroxymethyl, ($C_{1-5}$ alkoxy)methyl, ($C_{1-5}$ alkylthio)methyl, cyano, nitro or thiocyanato,
$R^6$ represents hydrogen, $C_{1-4}$ alkyl or $C_{1-4}$ fluoroalkyl, and alternatively $R^5$ and $R^6$ represent tri- or tetramethylene in which one methylene group may be replaced by oxygen or sulfur and which may be optionally substituted by $C_{1-3}$ alkyl, and
X represents oxygen or sulfur,
provided that (I) when $R^5$ represents fluorine, $R^6$ necessarily represents $C_{1-4}$ alkyl or $C_{1-4}$ fluoroalkyl, and (II) when $R^5$ represents cyano, $R^6$ necessarily represents hydrogen or $C_{1-4}$ alkyl and X necessarily represents oxygen, and a salt of the compound wherein $R^1$ and/or $R^2$ represent hydrogen [Japanese Patent Application Laid Open No. 61-221178 (=U.S. Pat. No. 4,746,352, U.S. Pat. No. 4,760,163)]:

a compound of the formula:

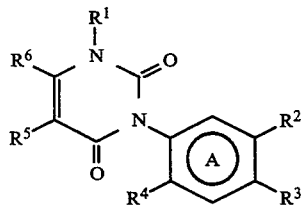

in which
$R^1$ represents hydrogen, $C_{1-4}$ alkyl, $C_{1-4}$ haloalkyl, formyl or $C_{2-6}$ alkanoyl,
$R^2$ represents an ether group, or a residue containing (thio)carbonyloxy group or sulfonyloxy group, the residue being directly bonded to a benzene ring A through oxygen atom,
$R^3$ represents halogen or cyano,
$R^4$ represents hydrogen or halogen,
$R^5$ represents hydrogen, halogen or $C_{1-4}$ alkyl,
$R^6$ represents $C_{1-4}$ alkyl or $C_{1-4}$ haloalkyl, and alternatively $R^5$ and $R^6$ represent tri- or tetramethylene, and a salt of the compound wherein $R^1$ represents hydrogen [Japanese Patent Application Laid Open No. 63-41466 (=U.S. Pat. No. 4,859,229)]:

$C_{1-4}$ alkyl, $C_{2-4}$ alkenyl and $C_3$ or $C_4$ alkynylenol ethers of 3-aryluracil represented by the following formula:

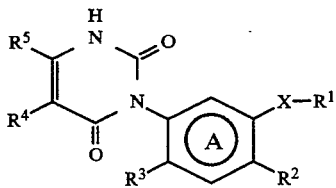

in which

R$^1$ represents $C_{1-8}$ alkyl, $C_{2-6}$ alkenyl, $C_{2-6}$ alkynyl, $C_{2-8}$ alkoxyalkyl or

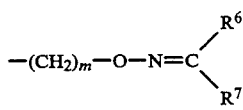

group,

R$^2$ represents halogen or cyano,

R$^3$ represents hydrogen or halogen,

R$^4$ represents hydrogen, fluorine or $C_{1-4}$ alkyl,

R$^5$ represents $C_{1-4}$ alkyl or $C_{1-4}$ haloalkyl, and alternatively R$^4$ and R$^5$ represent tri or tetramethylene, R$^6$ and R$^7$ each independently represents $C_{1-4}$ alkyl, m is 1 or 2, and X represents O, O—C(O), O—C(O)—O or C(O)—O [Japanese Patent Application Laid Open No. 63-107967 (=U.S. Pat. No. 4,812,164)]:

compounds disclosed as an aryluracil derivative in Japanese Patent Application Laid Open No. 54-147923 (=U.S. Pat. No. 4,266,056, U.S. Pat. No. 4,338,318), WO/89-03825, U.S. Pat. No. 4,927,451, U.S. Pat. No. 4,941,909, etc. may be mentioned.

There have been desired to provide an aryl uracil compound which promptly show high effect against many kinds of weeds including perennial weeds in an extremely low application amount and have the suitable residual effect with substantially no damage against important crops according to either of the soil treatment method or the foliar treatment method.

DISCLOSURE OF THE INVENTION

We have been studied in order to develop a herbicide showing selectivity against important crops, having excellent herbicidal effect against many weeds in a low application amount, and having both of soil treatment and foliar treatment effects. And as the result, we have found an uracil derivative (hereinafter referred to the compound of the present invention) represented by the formula (1):

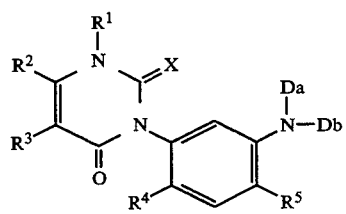

in which

R$^1$ represents a hydrogen atom, a C$_1$ to C$_3$ alkyl group or a C$_1$ to C$_3$ haloalkyl group;

R$^2$ represents a C$_1$ to C$_6$ haloalkyl group;

R$^3$ represents a hydrogen atom, a C$_1$ to C$_6$ alkyl group, a C$_1$ to C$_6$ haloalkyl group, a hydroxymethyl group, a halogen atom or a nitro group;

R$^4$ represents a hydrogen atom or a halogen atom;

R$^5$ represents a hydrogen atom, a halogen atom, a nitro group or a cyano group;

X represents an oxygen atom or a sulfur atom;

D$_a$ and D$_b$ each independently represents a hydrogen atom, a C$_1$ to C$_8$ alkyl group, a C$_1$ to C$_6$ haloalkyl group, a C$_3$ to C$_8$ cycloalkyl group, a C$_3$ to C$_8$ cycloalkyl(C$_1$ to C$_4$)alkyl group, a C$_2$ to C$_8$ alkenyl group, a C$_2$ to C$_8$ alkynyl group, a C$_2$ to C$_8$ haloalkenyl group, a C$_3$ to C$_8$ haloalkynyl group, a C$_3$ to C$_8$ halocycloalkyl group, a C$_3$ to C$_8$ halocycloalkyl(C$_1$ to C$_4$)alkyl group, CH(OH)CCl$_3$, Ar in which Ar represents a phenyl group or a naphthyl group each of which may be substituted by one or two or more substituents, —L$^1$—Ar in which Ar has the same meaning as above, and L$^1$ represents a C$_1$ to C$_6$ alkyl chain, a C$_2$ to C$_6$ alkenyl chain or a C$_2$ to C$_6$ alkynyl chain each of which may be branched, Het in which Het represents a 5-membered heterocyclic residue, a 6-membered heterocyclic residue or a fused heterocyclic residue each of which contains, as a ring constituent atom, at least one atom selected from a sulfur atom, an oxygen atom and a nitrogen atom and may be substituted by one or two or more substituents, —L$^1$—Het in which Het and L$^1$ have the same meanings as above, —L$^2$—D$^{52}$ in which D$^{52}$ represents a hydrogen atom, a C$_1$ to C$_{20}$ alkyl group, a C$_1$ to C$_{20}$ haloalkyl group, a C$_3$ to C$_8$ cycloalkyl group, a C$_3$ to C$_8$ cycloalkyl(C$_1$ to C$_4$)alkyl group, a C$_2$ to C$_8$ alkenyl group, a C$_3$ to C$_8$ alkynyl group, a C$_2$ to C$_8$ haloalkenyl group, a C$_3$ to C$_8$ haloalkynyl group, C$_3$ to C$_8$ halocycloalkyl group, a C$_3$ to C$_8$ halocycloalkyl(C$_1$ to C$_4$)alkyl group, a C$_1$ to C$_4$ alkoxy(C$_1$ to C$_4$)alkyl group, Ar (Ar has the same meaning as above), —L$^1$—Ar group (Ar and L$^1$ have the same meanings as above), Het (Het has the same meaning as above) or —L$^1$—Het (Het and L$^1$ have the same meanings as above), and L$^2$ represents —C(O)—, —C(S)—, —O$_2$—, —S(O)—, —S—, —O—, —C(O)O—, —C(O)S—, —C(S)O—, —C(S)S— or —C(O)C(O)O—, —L$^3$—O—D$^{52}$ in which D$^{52}$ has the same meaning as above, and L$^3$ represents a C$_1$ to C$_6$ alkyl chain, a C$_2$ to C$_6$ alkenyl chain or a C$_2$ to C$_6$ alkynyl chain each of which may be substituted by one or two or more substituents and may be branched, and the substituent may be selected from a C$_1$ to C$_4$ alkyloxycarbonyl group, a C$_1$ to C$_4$ haloalkyl group, a C$_1$ to C$_4$ alkoxy(C$_1$ to C$_4$)alkyl group, a C$_1$ to C$_4$ alkylthio group, Ar (Ar has the same meaning as above), —L$^1$—Ar (Ar and L$^1$ have the same meanings as above), Her (Het has the same meaning as above) and —L$^1$—Het (Het and L$^1$ have the same meanings as above), —L$^3$—S—D$^{52}$ in which D$^{52}$ and L$^3$ have the same meanings as above, —L$^3$—C(O)—D$^{52}$ in which D$^{52}$ and L$^3$ have the same meanings as above, —$L^3$—C(S)—$D^{52}$ in which $D^{52}$ and $L^3$ have the same meanings as above, —$L^3$—C(O)O—$D^{52}$ in which $D^{52}$ and $L^3$ have the same meanings as above, —O—$L^3$—C(O)O—$D^{52}$ in which $D^{52}$ and $L^3$ have the same meanings as above, —$L^3$—C(O)S—$D^{52}$ in which $D^{52}$ and $L^3$ have the same meanings as above, —O—$L^3$—C(O)S—$D^{52}$ in which $D^{52}$ and $L^3$ have the same meanings as above, —C(O)—$ND^{52}D^{53}$ in which $D^{52}$ has the same meanings as above and $D^{53}$ represents a hydrogen atom, a $C_1$ to $C_8$ alkyl group, a $C_1$ to $C_8$ haloalkyl group, a $C_1$ to $C_6$ alkoxy group, a $C_1$ to $C_6$ alkylcarbonyl group, a $C_1$ to $C_6$ haloalkylcarbonyl group, a $C_1$ to $C_6$ alkoxycarbonyl group, a $C_1$ to $C_6$ alkylsulfonyl group, a $C_1$ to $C_6$ haloalkylsulfonyl group, Ar (Ar has the same meaning as above), —$L^1$—Ar (Ar and $L^1$ have the same meanings, as above), —C(O)—Ar (Ar has the same meaning as above), —C(O)—Ar (Ar has the same meaning as above) or —$SO_2$—Ar (Ar has the same meaning as above), and alternatively $D^{52}$ and $D^{53}$ together with a nitrogen atom to which they are attached may form a 5- to 7-membered ring, and the ring constituent atoms are selected from a carbon atom, a nitrogen atom, an oxygen atom and a sulfur atom, —C(S)—$ND^{52}D^{53}$ in which $D^{52}$ and $D^{53}$ have the same meanings as above, —$L^3$—C(O)—$ND^{52}D^{53}$ in which $D^{52}$, $D^{53}$ and $L^3$ have the same meanings as above, —$L^3$—C(S)—$ND^{52}D^{53}$ in which $D^{52}$, $D^{53}$ and $L^3$ have the same meanings as above, —$SO_2$—$ND^{52}D^{53}$ in which $D^{52}$ and $D^{53}$ have the same meanings as above, —$SO_2O$—$D^{53}$ in which $D^{53}$ has the same meaning as above, —$SO_2O$—$Si(CH_3)_3$, —$SO_2$—$L_1$—$Si(CH_3)_3$ in which $L^1$ has the same meaning as above,

—$SO_2CH_2SO_2CH_3$,

—P(O) ($OD^{52}$) ($OD^{53}$) in which $D^{52}$ and $D^{53}$ have the same meanings as above, —P(O) ($OD^{52}$) ($SD^{53}$) in which $D^{52}$ and $D^{53}$ have the same meanings as above, —P(O) ($OD^{52}$)$D^{53}$ in which $D^{52}$ and $D^{53}$ have the same meanings as above, —P(O)($SD^{52}$)$D^{53}$ in which $D^{52}$ and $D^{53}$ have the same meanings as above, —P(S) ($OD^{52}$) ($OD^{53}$) in which $D^{52}$ and $D^{53}$ have the same meanings as above, —P(S) ($OD^{52}$) ($SD^{53}$) in which $D^{52}$ and $D^{53}$ have the same meanings as above, —P(S) ($OD^{52}$)$D^{53}$ in which $D^{52}$ and $D^{53}$ have the same meanings as above, —P(S) ($SD^{52}$)$D^{53}$ in which $D^{52}$ and $D^{53}$ have the same meanings as above, —$L^3$—P(O) ($OD^{52}$) ($OD^{53}$) in which $D^{52}$, $D^{53}$ and $L^3$ have the same meanings as above, —$L^3$—P(O) ($OD^{52}$) ($SD^{53}$) in which $D^{52}$, $D^{53}$ and $L^3$ have the same meanings as above, —$L^3$—P(O) ($OD^{52}$)$D^{53}$ in which $D^{52}$, $D^{53}$ and $L^3$ have the same meanings as above, —$L^3$—P(O) ($SD^{52}$)$D^{53}$ in which $D^{52}$, $D^{53}$ and $L^3$ have the same meanings as above, —$L^3$—P(S) ($OD^{52}$) ($OD^{53}$) in which $D^{52}$, $D^{53}$ and $L^3$ have the same meanings as above, —$L^3$—P(S) ($OD^{52}$) ($SD^{53}$) in which $D^{52}$, $D^{53}$ and $L^3$ have the same meanings as above, —$L^3$—P(S) ($OD^{52}$)$D^{53}$ in which $D^{52}$, $D^{53}$ and $L^3$ have the same meanings as above, —$L^3$—P(S) ($SD^{52}$)$D^{53}$ in which $D^{52}$, $D^{53}$ and $L^3$ have the same meanings as above, —C($D^{53}$) (P(O) ($OD^{52}$)$_2$)$_2$ in which $D^{52}$ and $D^{53}$ have the same meanings as above, =$CD^{52}D^{54}$ in which $D^{52}$ has the same meaning as above, and $D^{54}$ represents a hydrogen atom, a halogen atom, a $C_1$ to $C_6$ alkyl group, a $C_1$ to $C_6$ alkoxy group, a $C_1$ to $C_6$ alkylthio group or Ar (Ar has the same meaning as above), —$L^3$—CN in which $L^3$ has the same meaning as above, —$ND^{52}D^{53}$ in which $D^{52}$ and $D^{53}$ have the same meanings as above, —CH=N—O—$D^{52}$ in which $D^{52}$ has the same meaning as above, =$CD^{54}$—$ND^{52}D^{53}$ in which $D^{52}$, $D^{53}$ and $D^{54}$ have the same meanings as above, —$L^2$—$D^{55}$ in which $L^2$ has the same meaning as above, and $D^{55}$ represents a $C_1$ to $C_6$ alkyl group, a $C_2$ to $C_6$ alkenyl group or a $C_2$ to $C_6$ alkynyl group each of which may be substituted by one or two or more of a $C_1$ to $C_6$ haloalkyl group or one or two or more of a $C_1$ to $C_4$ alkyloxycarbonyl group and may be branched, or —$L^1$—$SO_2$—$D^{56}$ in which $L^1$ has the same meaning as above, and $D^{56}$ represents a $C_1$ to $C_6$ alkyl group, and alternatively $D_a$ and $D_b$ together with a nitrogen atom to which they are attached may form a 3- to 8-membered ring and the ring constituent atoms are selected from a carbon atom, a nitrogen atom, an oxygen atom, a sulfur atom and a phosphorus atom, and the ring may be substituted:

provided that except for the case where $D_a$ and $D_b$ both represent hydrogen atoms, the case where $D_a$ represents —$L^2$—$D^{52}$ ($L^2$ represents —$SO_2$— and $D^{52}$ represents the $C_1$ to $C_4$ alkyl group or the $C_1$ to $C_3$ haloalkyl group) and $D_b$ represents the hydrogen atom, the $C_1$ to $C_4$ alkyl group, the $C_2$ to $C_5$ alkenyl group, the $C_3$ to $C_5$ alkynyl group, the $C_2$ to $C_5$ acyl group, the $C_1$ to $C_4$ alkylsulfonyl group or the ($C_1$ to $C_3$ alkoxy) $C_1$ to $C_2$ alkyl group is excluded, has the above characteristics. The above finding leads to the present invention.

Characteristic features in the structure of the compound of the present invention are to have a haloalkyl group at 6-position of the uracil ring and have specific combination of $R^4$, $R^5$ and $N(D_a)D_b$ as the substituents on the benzene ring at 3-position of the uracil ring. By having such a structure, the compound of the present invention has a permeation and translocation and the very high herbicidal activity. As the results, the compound of the present invention has great merits that it can be applied according to either the soil treatment or the foliar treatment against many kinds of weeds including the perennial weeds, that it can develop the high effect promptly even if the application amount is very low, and that it has the suitable residual effect.

Incidentally, the compound of the present invention represented by the formula (1) may be a tautomer as shown below, when the substituent $R^1$ is the hydrogen atom, and the compound of the present invention includes all of these forms.

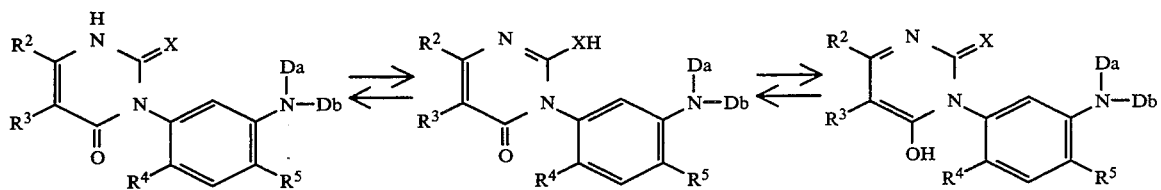

As the general method for synthesizing an uracil derivative, uracil skeleton can be synthesized by referring to the synthesis method described in, for example, A. R. Katritzky et al., Comprehensive Heterocyclic Chemistry, 3, p. 57 (1984), etc. 3-Amino-4,4,4-trifluorocrotonate ester which is one of starting materials may be synthesized by referring to A. W. Lutz et al., Journal of Heterocyclic Chemistry, 9 (3), p. 513 (1972), etc.

Including the above methods, the compound of the present invention can be synthesized by, for example, the methods shown in Schemes 1 to 5. $R^1$, $R^2$, $R^3$, $R^4$, $R^5$, X, $D_a$ and $D_b$ in Schemes 1 to 5 have the same meanings as described in the above, $G^1$ represents an alkyl group having 1 to 4 carbon atoms, $G^2$ represents an alkyl group having 1 to 4 carbon atoms or a phenyl group, and Hal represents a halogen atom, methanesulfonyloxy group or a paratoluenesulfonyloxy group.

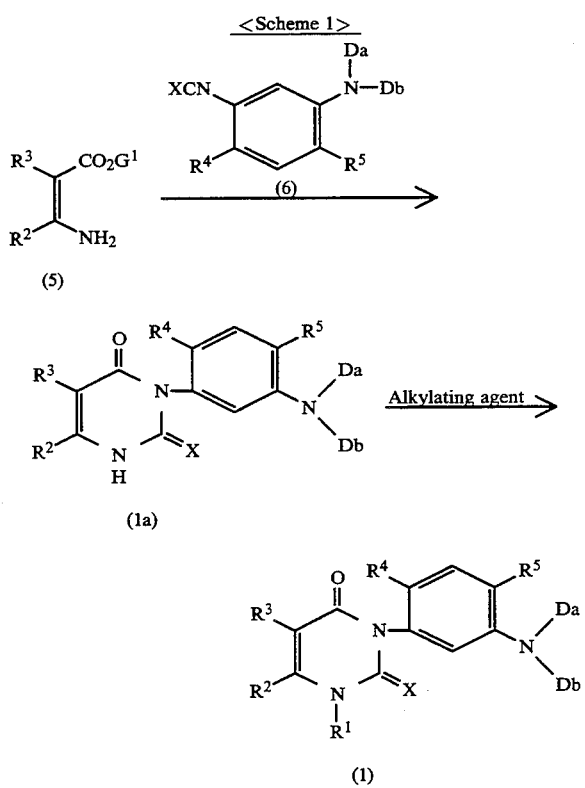

1. Scheme 1 shows a method for preparing an uracil derivative (1) by reacting phenyliso(thio)cyanate (6) with β-aminoacrylate ester (5) to form an uracil derivative (1a) in a first step, and after isolation of the derivative (1a) or subsequently, without isolation, alkylating 1-position of the uracil ring in a second step.

① Reaction in the First Step

The compound (6) is generally used in an amount of 0.5 to 1.5 equivalent, preferably 0.8 to 1.2 equivalent based on the compound (5).

The reaction may proceed without any solvent, but it is generally promoted by using a solvent. As the solvent, there may be mentioned aliphatic hydrocarbons such as hexane, heptane, ligroin, petroleum ether, etc.; aromatic hydrocarbons such as benzene, toluene, xylene, chlorobenzene, etc.; halogenated hydrocarbons such as chloroform, methylene chloride, etc.; ethers such as diethyl ether, dioxane, tetrahydrofuran, etc.; ketones such as acetone, methyl ethyl ketone, etc.; nitriles such as acetonitrile, isobutyronitrile, etc.; tertiary amines such as pyridine, N,N-diethylaniline, etc.; acid amides such as N, N-dimethylacetamide, N, N-dimethylformamide, N-methylpyrrolidone, etc.; sulfur-containing compounds such as dimethylsulfoxide, sulfolane, etc.; water and their mixture, and preferably the aliphatic hydrocarbons, the aromatic hydrocarbons, the acid amides, the sulfur-containing compounds and their mixture.

The reaction may proceed without any base, but generally a base in an amount of 0.5 to 10 equivalents, preferably 1.0 to 3.0 equivalents based on the compound (5) is used. As the base, there may be mentioned nitrogen-containing organic bases such as pyridine, triethylamine, N,N-dimethylaniline, N,N-diethylaniline, 4-(N,N-dimethylamino)pyridine, 1,4-diazabicyclo[2.2.2]octane, etc.; inorganic bases such as sodium hydride, potassium hydride, sodium hydroxide, potassium hydroxide, sodium carbonate, potassium carbonate, etc.; and metal alcoholates such as sodium methoxide, sodium ethoxide, potassium tert-butoxide, etc., and preferably sodium hydride, sodium hydroxide and potassium hydroxide.

The reaction temperature is generally −70° to 200° C., preferably −30° C. to the reflux temperature of the reaction mixture.

The reaction time is generally 5 minutes to 72 hours, preferably 10 minutes to 12 hours.

After the reaction is completed followed by acidifying with a mineral acid such as hydrochloric acid, etc., or an organic acid such as acetic acid, trifluoroacetic acid, p-toluenesulfonic acid, etc., the derivative (1a) can be isolated.

② The Second Step

The alkylating agent is used in an amount of 0.5 to 10 equivalents, preferably 0.8 to 5.0 equivalents based on the derivative (1a). As the alkylating agent, there may be mentioned alkylsulfates such as dimethylsulfate, diethylsulfate, etc.; and halogenated alkyls such as methyl chloride, ethyl chloride, methyl bromide, ethyl bromide, methyl iodide, ethyl iodide, etc.

The reaction may proceed without any solvent, but it is generally promoted by using a solvent. As the solvent, there may be mentioned aliphatic hydrocarbons such as hexane, heptane, ligroin, petroleum ether, etc.; aromatic hydrocarbons such as benzene, toluene, xylene, chlorobenzene, etc.; halogenated hydrocarbons such as chloroform, methylene chloride, etc.; ethers such as diethyl ether, dioxane, tetrahydrofuran, etc.; ketones such as acetone, methyl ethyl ketone, etc.; nitriles such as acetonitrile, isobutyronitrile, etc.; tertiary amines such as pyridine, N,N-diethylaniline, etc.; acid amides such as N,N-dimethylacetamide, N,N-dimethylformamide, N-methylpyrrolidone, etc.; sulfur-containing compounds such as dimethylsulfoxide, sulfolane, etc.; water and their mixture, and preferably the aliphatic hydrocarbons, the aromatic hydrocarbons, the ethers, the ketones, the nitriles, the acid amides, the sulfur-containing compounds and their mixture.

A base is generally used in an amount of 0.5 to 10 equivalents, preferably 0.8 to 3.0 equivalents based on the derivative (1a). As the base, there may be mentioned nitrogen-containing organic bases such as pyridine, triethylamine, N,N-dimethylaniline, N,N-diethylaniline, 4-(N,N-dimethylamino)pyridine, 1,4-diazabicyclo[2.2.2]octane, etc. and inorganic bases such as sodium hydride, potassium hydride, sodium hydroxide, potassium hydroxide, sodium carbonate, potassium carbonate, etc., and preferably the inorganic bases such as sodium hydride, potassium carbonate, etc.

The reaction temperature is generally $-30°$ to $150°$ C., preferably $-10°$ C. to the reflux temperature of the reaction mixture.

The reaction time is generally 10 minutes to 96 hours, preferably 30 minutes to 48 hours.

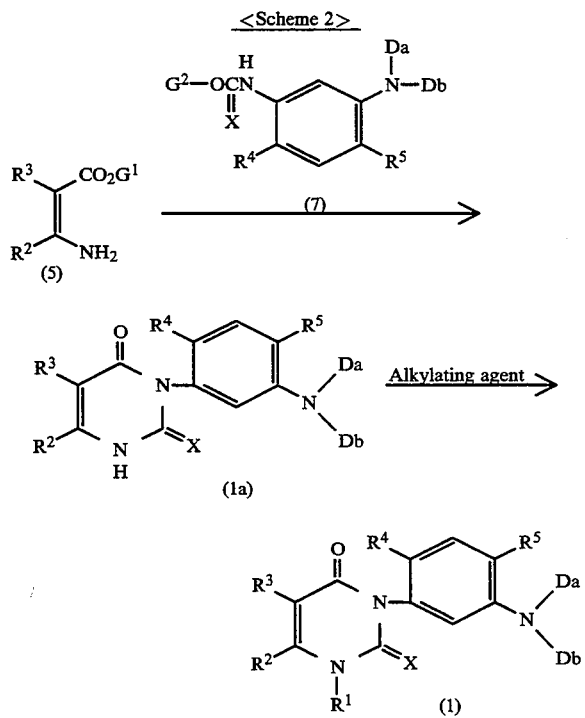

2. Scheme 2 shows a method for preparing an uracil derivative (1) by reacting N-phenyl(thio)carbamate (7) with β-aminoacrylate ester (5) to form an uracil derivative (1a) in a first step, and after isolation of the derivative (1a) or subsequently, without isolation, alkylating 1-position of the uracil ring in a second step.

① Reaction in the First Step

The compound (7) is generally used in an amount of 0.5 to 1.5 equivalent, preferably 0.8 to 1.2 equivalent based on the compound (5).

The reaction generally requires a solvent. As the solvent, there may be mentioned aliphatic hydrocarbons such as hexane, heptane, ligroin, petroleum ether, etc.; aromatic hydrocarbons such as benzene, toluene, xylene, chlorobenzene, etc.; halogenated hydrocarbons such as chloroform, methylene chloride, etc.; ethers such as diethyl ether, dioxane, tetrahydrofuran, etc.; ketones such as acetone, methyl ethyl ketone, etc.; nitriles such as acetonitrile, isobutyronitrile, etc.; tertiary amines such as pyridine, N,N-diethylaniline, etc.; acid amides such as N,N-dimethylacetamide, N,N-dimethylformamide, N-methylpyrrolidone, etc.; sulfur-containing compounds such as dimethylsulfoxide, sulfolane, etc.; alcohols such as methanol, ethanol, propanol, butanol, etc.; water and their mixture, and preferably the aliphatic hydrocarbons, the aromatic hydrocarbons, the acid amides, the sulfur-containing compounds and their mixture.

A base is generally used in an amount of 0.5 to 10 equivalents, preferably 1.0 to 3.0 equivalents based on the compound (5). As the base, there may be mentioned nitrogen-containing organic bases such as pyridine, triethylamine, N,N-dimethylaniline, N,N-diethylaniline, 4-(N,N-dimethylamino)pyridine, 1,4-diazabicyclo[2.2.21]octane, etc.; inorganic bases such as sodium hydride, potassium hydride, sodium hydroxide, potassium hydroxide, sodium carbonate, potassium carbonate, etc.; metal alcoholates such as sodium methoxide, sodium ethoxide, potassium tert-butoxide, etc.; and metal alkylmercaptides such as sodium methylmercaptide, sodium ethylmercaptide, etc., and preferably the inorganic bases such as sodium hydride, sodium hydroxide, potassium hydroxide, sodium carbonate, potassium carbonate, etc., and the metal alcoholates such as sodium methoxide, etc.

The reaction temperature is generally $0°$ to $200°$ C., preferably the room temperature to the reflux temperature of the reaction mixture.

The reaction time is generally 10 minutes to 72 hours, preferably 30 minutes to 24 hours.

After completion of the reaction followed by acidifying with a mineral acid such as hydrochloric acid, etc., or an organic acid such as acetic acid, trifluoroacetic acid, p-toluenesulfonic acid, etc., the derivative (1a) can be isolated.

② The Second Step

Alkylation can be carried out under the same reaction conditions as in the second step of Scheme 1.

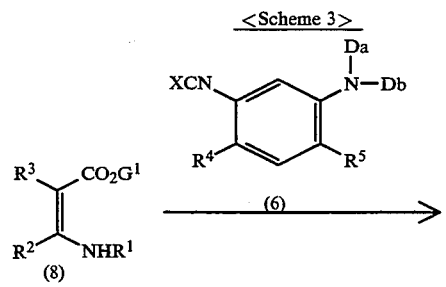

-continued

<Scheme 3>

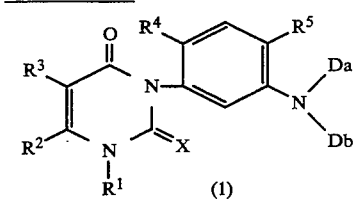

3. Scheme 3 shows a method for preparing an uracil derivative (1) by reacting phenyliso (thio) cyanate (6) with N-alkyl-β-aminoacrylate ester (8) in one step and may be carried out under the same reaction conditions as in Scheme 1.

<Scheme 4>

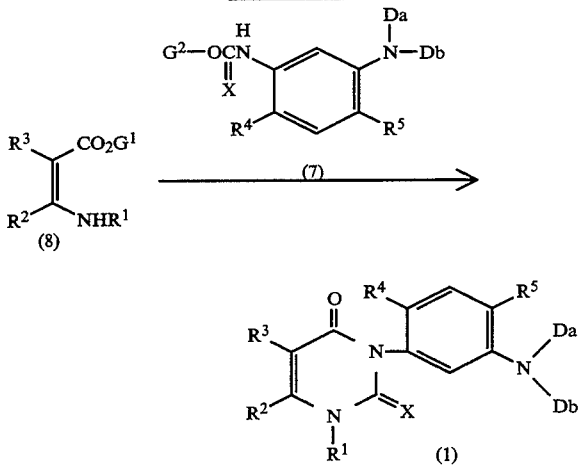

4. Scheme 4 shows a method for preparing an uracil derivative (1) by reacting N-phenyl(thio)carbamate (7) with N-alkyl-β-aminoacrylate ester (8) in one step and may be carried out under the same reaction conditions as in Scheme 2.

<Scheme 5>

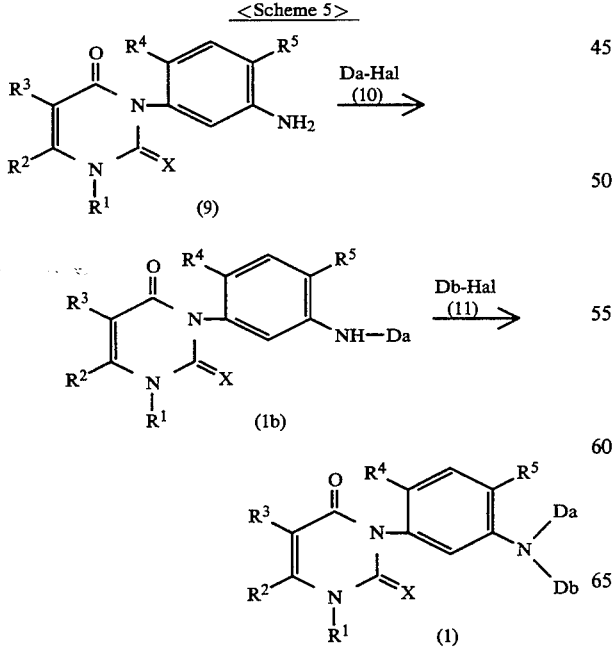

5. Scheme 5 shows a method for preparing an uracil derivative (1) by reacting $D_a$-Hal (10) with an amino material (9) to form an uracil derivative (1b) in a first step, and after isolation of the derivative (1b) or subsequently, without isolation, reacting $D_b$-Hal (11) with the derivative (1b) in a second step.

① Reaction in the First Step

The compound (10) is generally used in an amount of 0.3 to 10 equivalents, preferably 0.5 to 2.0 equivalents based on the compound (9).

The reaction may proceed without any solvent, but it is generally promoted by using a solvent. As the solvent, there may be mentioned aliphatic hydrocarbons such as hexane, heptane, ligroin, petroleum ether, etc.; aromatic hydrocarbons such as benzene, toluene, xylene, chlorobenzene, etc.; halogenated hydrocarbons such as chloroform, methylene chloride, etc.; ethers such as diethyl ether, dioxane, tetrahydrofuran, etc.; ketones such as acetone, methyl ethyl ketone, etc.; nitriles such as acetonitrile, isobutyronitrile, etc.; tertiary amines such as pyridine, N,N-diethylaniline, etc.; acid amides such as N,N-dimethylacetamide, N,N-dimethylformamide, N-methylpyrrolidone, etc.; sulfur-containing compounds such as dimethylsulfoxide, sulfolane, etc., and their mixture.

The reaction may proceed without any base, but generally a base in an amount of 0.3 to 10 equivalents based on the compound (9) is used. Also, it may be used in a very excess amount as a solvent. As the base, there may be mentioned nitrogen-containing organic bases such as pyridine, triethylamine, N,N-dimethylaniline, N,N-diethylaniline, 4-(N,N-dimethylamino)pyridine, 1,4-diazabicyclo[2.2.2][octane, etc.; inorganic bases such as sodium hydride, potassium hydride, sodium hydroxide, potassium hydroxide, sodium carbonate, potassium carbonate, etc.; and metal alcoholates such as sodium methoxide, sodium ethoxide, potassium tert-butoxide, etc., and preferably the nitrogen-containing organic bases and the inorganic bases.

The reaction temperature is generally −30° to 160° C., preferably −10° C. to 130° C.

The reaction time is generally 10 minutes to 48 hours, preferably 30 minutes to 24 hours.

② The Second Step

The reaction can be carried out under the same conditions as in the first step of Scheme 5.

Among the compounds of the present invention represented by the formula (1), obtained according to the above methods, the following uracil compounds are preferred.

In the formula (1), $R^1$ represents a hydrogen atom, a $C_1$ to $C_3$ alkyl group, a $C_1$ to $C_3$ haloalkyl group;

$R^2$ represents a $C_1$ to $C_6$ haloalkyl group;

$R^3$ represents a hydrogen atom, a $C_1$ to $C_6$ alkyl group, a $C_1$ to $C_6$ haloalkyl group, a hydroxymethyl group, a halogen atom or a nitro group;

$R^4$ represents a hydrogen atom or a halogen atom;

$R^5$ represents a hydrogen atom, a halogen atom, a nitro group or cyano group;

X represents an oxygen atom or a sulfur atom;

$D_a$ and $D_b$ each independently represents a hydrogen atom, a $C_1$ to $C_8$ alkyl group, a $C_1$ to $C_6$ haloalkyl group, a $C_3$ to $C_8$ cycloalkyl group, a $C_3$ to $C_8$ cycloalkyl($C_1$ to $C_4$)alkyl group, a $C_2$ to $C_8$ alkenyl group, a $C_3$ to $C_8$ alkynyl group, a $C_2$ to $C_8$ haloalkenyl group, a $C_3$ to $C_8$ haloalkynyl group, a $C_3$ to $C_8$ halocycloalkyl group, a $C_3$ to $C_8$ halocycloalkyl($C_1$ to $C_4$)alkyl group, $CH(OH)CCl_3$, Ar in which Ar represents a phenyl group or a naphthyl group each of which may be substituted by one or two or more substituents, and the substituent may be selected from a $C_1$ to $C_4$ alkyl group, a $C_3$ to $C_6$ cycloalkyl group, a $C_1$ to $C_4$ haloalkyl group, a $C_3$ to $C_6$ halocycloalkyl group, a halogen atom, a cyano group, a nitro group, a hydroxy group, a $C_1$ to $C_4$ alkoxy group, a $C_1$ to $C_4$ haloalkoxy group, a $C_1$ to $C_4$ alkylcarbonyl group, a carboxyl group, a $C_1$ to $C_4$ alkoxycarbonyl group, an amino group, a $C_1$ to $C_4$ alkylamino group, an acetamino group, N,N-dimethylamino group and methanesulfonyl group, —$L^1$—Ar in which Ar has the same meaning as above, and $L^1$ represents a $C_1$ to $C_6$ alkyl chain, a $C_2$ to $C_6$ alkenyl chain or a $C_2$ to $C_6$ alkynyl chain each of which may be branched, Het in which Het represents a 5-membered heterocyclic residue, a 6-membered heterocyclic residue or a fused heterocyclic residue each of which contains, as a ring constituent atom, at least one atom selected from a sulfur atom, an oxygen atom and a nitrogen atom and may be substituted by one or two or more substituents, and the substituent may be selected from a $C_1$ to $C_4$ alkyl group, a $C_3$ to $C_6$ cycloalkyl group, a $C_1$ to $C_4$ haloalkyl group, a $C_3$ to $C_6$ halocycloalkyl group, a halogen atom, a cyano group, a nitro group, a hydroxy group, a $C_1$ to $C_4$ alkoxy group, a $C_1$ to $C_4$ haloalkoxy group, a $C_1$ to $C_4$ alkylcarbonyl group, a carboxyl group, a $C_1$ to $C_4$ alkoxycarbonyl group, an amino group, a $C_1$ to $C_4$ alkylamino group, an acetamino group, N,N-dimethylamino group and methanesulfonyl group, —$L^1$—Het in which Het and $L^1$ have the same meanings as above, —$L^2$—$D^{52}$ in which $D^{52}$ represents a hydrogen atom, a $C_1$ to $C_{20}$ alkyl group, a $C_1$ to $C_{20}$ haloalkyl group, a $C_3$ to $C_8$ cycloalkyl group, a $C_3$ to $C_8$ cycloalkyl($C_1$ to $C_4$)alkyl group, a $C_2$ to $C_8$ alkenyl group, a $C_3$ to $C_8$ alkynyl group, a $C_2$ to $C_8$ haloalkenyl group, a $C_3$ to $C_8$ haloalkynyl group, a $C_3$ to $C_8$ halocycloalkyl group, a $C_3$ to $C_8$ halocycloalkyl($C_1$ to $C_4$)alkyl group, a $C_1$ to $C_4$ alkoxy($C_1$ to $C_4$)alkyl group, Ar (Ar has the same meaning as above), —$L^1$—Ar (Ar and $L^1$ have the same meanings as above), Het (Het has the same meaning as above) or —$L^1$—Het (Het and $L^1$ have the same meanings as above), and $L^2$ represents —C(O)—, —C(S)—, —$SO_2$—, —S(O)—, —S—, —O—, —C(O)O—, —C(S)O—, —C(S)S— or —C(O)C(O)O—, —$L^3$—O—$D^{52}$ in which $D^{52}$ has the same meaning as above, and $L^3$ represents a $C_1$ to $C_6$ alkyl chain, a $C_2$ to $C_6$ alkenyl chain or a $C_2$ to $C_6$ alkynyl chain each of which may be substituted by one or two or more substituents and may be branched, and the substituent may be selected from a $C_1$ to $C_4$ alkyloxycarbonyl group, a $C_1$ to $C_4$ haloalkyl group, a $C_1$ to $C_4$ alkoxy($C_1$ to $C_4$)alkyl group, a $C_1$ to $C_4$ alkylthio group, Ar (Ar has the same meaning as above), —$L^1$—Ar (Ar and $L^1$ have the same meanings as above), Het (Het has the same meaning as above) and —$L^1$—Het (Het and $L^1$ have the same meanings as above), —$L^3$—S—$D^{52}$ in which $D^{52}$ and $L^3$ have the same meanings as above, —$L^3C(O)$—(O)—$D^{52}$ in which $D^{52}$ and $L^3$ have the same meanings as above, —$L^3$—C(S)—$D^{52}$ in which $D^{52}$ and $L^3$ have the same meanings as above, —$L^3$—C(O)O—$D^{52}$ in which $D^{52}$ and $L^3$ have the same meanings as above, —O—$L^3$—C(O)O—$D^{52}$ in which $D^{52}$ and $L^3$ have the same meanings as above, —$L^3$—C(O)S—$D^{52}$ in which $D^{52}$ and $L^3$ have the same meanings as above, —O—$L^3$—C(O)S—$D^{52}$ in which $D^{52}$ and $L^3$ have the same meanings as above, —C(O)—$ND^{52}D^{53}$ in which $D^{52}$ has the same meaning as above, and $D^{53}$ represents a hydrogen atom, a $C_1$ to $C_8$ alkyl group, a $C_1$ to $C_8$ haloalkyl group, a $C_1$ to $C_6$ alkoxy group, a $C_1$ to $C_6$ alkylcarbonyl group, a $C_1$ to $C_6$ haloalkylcarbonyl group, a $C_1$ to $C_6$ alkoxycarbonyl group, a $C_1$ to $C_6$ alkylsulfonyl group, a $C_1$ to $C_6$ haloalkylsulfonyl group, Ar (Ar has the same meaning as above), —$L^1$—Ar (Ar and $L^1$ have the same meanings as above), —C(O)—Ar (Ar has the same meaning as above), —C(S)—Ar (Ar has the same meaning as above) or —$SO_2$—Ar (Ar has the same meaning as above), and alternatively $D^{52}$ and $D^{53}$ together with a nitrogen atom to which they are attached may form a 5- to 7-membered ring and ring constituent atoms are selected from a carbon atom, a nitrogen atom, an oxygen atom and a sulfur atom, —C(S)—$ND^{52}D^{53}$ in which $D^{52}$ and $D^{53}$ have the same meanings as above, —$L^3$—(O)—$ND^{52}D^{53}$ in which $D^{52}$, $D^{53}$ and $L^3$ have the same meanings as above, —$L^3$—C(S)—$ND^{52}D^{53}$ in which $D^{52}$, $D^{53}$ and $L^3$ have the same meanings as above, —$SO_2$—$ND^{52}D^{53}$ in which $D^{52}$ and $D^{53}$ have the same meanings as above, —$SO_2O$—$D^{53}$ in which $D^{53}$ has the same meaning as above, —$SO_2O$—$Si(CH_3)_3$, —$SO_2$—$L^1$—$Si(CH_3)_3$ in which $L^1$ has the same meaning as above,

—$SO_2CH_2SO_2CH_3$,

—P(O) ($OD^{52}$) ($OD^{53}$) in which $D^{52}$ and $D^{53}$ have the same meanings as above, —P(O) ($OD^{52}$) ($SD^{53}$) in which $D^{52}$ and $D^{53}$ have the same meanings as above, —P(O) ($OD^{52}$)$D^{53}$ in which $D^{52}$ and $D^{53}$ have the same meanings as above, —P(O) ($SD^{52}$)$D^{53}$ in which $D^{52}$ and $D^{53}$ have the same meanings as above, —P(S) ($OD^{52}$) ($OD^{53}$) in which $D^{52}$ and $D^{53}$ have the same meanings as above, —P(S) ($OD^{52}$) ($SD^{53}$) in which $D^{52}$ and $D^{53}$ have the same meanings as above, —P(S) ($OD^{52}$)$D^{53}$ in which $D^{52}$ and $D^{53}$ have the same meanings as above, —P(S) ($SD^{52}$)$D^{53}$ in which $D^{52}$ and $D^{53}$ have the same meanings as above, —$L^3$—P(O) ($OD^{52}$) ($OD^{53}$) in which $D^{52}$, $D^{53}$ and $L^3$ have the same meanings as above, —$L^3$—P(O) ($OD^{52}$) ($SD^{53}$) in which $D^{52}$, $D^{53}$ and $L^3$ have the same meanings as above, —$L^3$—P(O) ($OD^{52}$)$D^{53}$ in which $D^{52}$, $D^{53}$ and $L^3$ have the same meanings as above, —$L^3$—P(O) (SD$^{52}$)D$^{53}$ in which D$^{52}$, D$^{53}$ and L$^3$ have the same meanings as above, —$L^3$—P(S) (OD$^{52}$) (OD$^{53}$) in which D$^{52}$, D$^{53}$ and L$^3$ have the same meanings as above, —$L^3$—P(S) (OD$^{52}$) (SD$^{53}$) in which D$^{52}$, D$^{53}$ and L$^3$ have the same meanings as above, —$L^3$—P(S) (OD$^{52}$)D$^{53}$ in which D$^{52}$, D$^{53}$ and L$^3$ have the same meanings as above, —$L^3$—P(S) (SD$^{52}$)D$^{53}$ in which D$^{52}$, D$^{53}$ and L$^3$ have the same meanings as above, —C (D$^{53}$) (P(O) (OD$^{52}$)$_2$)$_2$ in which D$^{52}$ and D$^{53}$ have the same meanings as above, =CD$^{52}$D$^{54}$ in which D$^{52}$ has the same meaning as above, and D$^{54}$ represents a hydrogen atom, a halogen atom, a $C_1$ to $C_6$ alkyl group, a $C_1$ to $C_6$ alkoxy group, a $C_1$ to $C_6$ alkylthio group or Ar (Ar has the same meaning as above), —$L^3$—CN in which $L^3$ has the same meaning as above, —ND$^{52}$D$^{53}$ in which D$^{52}$ and D$^{53}$ have the same meanings as above, —CH=N—O—D$^{52}$ in which D$^{52}$ has the same meaning as above, =CD$^{54}$—ND$^{52}$D$^{53}$ in which D$^{52}$, D$^{53}$ and D$^{54}$ have the same meanings as above, —$L^2$—D$^{55}$ in which $L^2$ has the same meaning as above, and D$^{55}$ represents a $C_1$ to $C_6$ alkyl group, a $C_2$ to $C_6$ alkenyl group or a $C_2$ to $C_6$ alkynyl group each of which may be substituted by one or two or more of a $C_1$ to $C_6$ haloalkyl group or one or two or more of a $C_1$ to $C_4$ alkyloxycarbonyl group and may be branched, or —$L^1$—SO$_2$—D$^{56}$ in which $L^1$ has the same meaning as above, and D$^{56}$ represents a $C_1$ to $C_4$ alkyl group, and alternatively $D_a$ and $D_b$ together with a nitrogen atom to which they are attached may form a 3- to 8-membered ring and the ring constituent atoms are selected from a carbon atom, a nitrogen atom, an oxygen atom, a sulfur atom and a phosphorus atom, and the ring may be substituted by one or more substituents and the substituent may be selected from a $C_1$ to $C_4$ alkyl group, a $C_3$ to $C_6$ cycloalkyl group, a $C_1$ to $C_4$ haloalkyl group, a $C_3$ to $C_6$ halocycloalkyl group, a halogen atom, a cyano group, a nitro group, a hydroxy group, a $C_1$ to $C_4$ alkoxy group, a $C_1$ to $C_4$ haloalkoxy group, a $C_1$ to $C_4$ alkylcarbonyl group, a carboxyl group, a $C_1$ to $C_4$ alkoxycarbonyl group, an amino group, a $C_1$ to $C_4$ alkylamino group, an acetamino group, N,N-dimethylamino group and methanesulfonyl group:

provided that except for the case where $D_a$ and $D_b$ both represent the hydrogen atoms, the case where $D_a$ represents —$L^2$—D$^{52}$ in which $L^2$ represents —SO$_2$— and D$^{52}$ represents the $C_1$ to $C_4$ alkyl group or the $C_1$ to $C_3$ haloalkyl group and $D_b$ represents the hydrogen atom, the $C_1$ to $C_4$ alkyl group, the $C_2$ to $C_5$ alkenyl group, the $C_3$ to $C_5$ alkynyl group, the $C_2$ to $C_5$ acyl group, the $C_1$ to $C_4$ alkylsulfonyl group or the ($C_1$ to $C_3$ alkoxy) $C_1$ to $C_2$ alkyl group are excluded.

The more preferred compounds are those represented by the formula (I) wherein $R^1$ represents methyl group;

$R^2$ represents trifluoromethyl group;

$R^3$ represents hydrogen atom;

$R^4$ represents hydrogen atom or halogen atom;

$R^5$ represents a halogen atom;

X represents oxygen atom;

$D_a$ and $D_b$ each independently represents hydrogen atom, $C_1$ to $C_6$ alkyl group, $C_3$ to $C_6$ alkenyl group, $C_3$ to $C_6$ alkynyl group, —$L^1$—Ar in which $L^1$ represents a $C_1$ to $C_6$ alkyl chain, a $C_2$ to $C_6$ alkenyl chain or a $C_2$ to $C_6$ alkynyl chain each of which may be branched, and Ar represents a phenyl group or a naphthyl group each of which may be substituted by one or two or more substituents and the substituent may be selected from a $C_1$ to $C_4$ alkyl group, a $C_1$ to $C_4$ haloalkyl group, a halogen atom, a nitro group, a $C_1$ to $C_4$ alkoxy group and a $C_1$ to $C_4$ alkoxycarbonyl group, Het in which Het represents a pyridine ring, a thiophen ring and a furan ring, —$L^1$—Het in which Het and $L^1$ have the same meanings as above, —$L^2$—D$^{52}$ in which D$^{52}$ represents a hydrogen atom, a $C_1$ to $C_6$ alkyl group, a $C_1$ to $C_6$ haloalkyl group, a $C_3$ to $C_8$ cycloalkyl group, a $C_3$ to $C_8$ cycloalkyl($C_1$ to $C_2$)alkyl group, a $C_3$ to $C_6$ alkenyl group, a $C_3$ to $C_6$ alkynyl group, a $C_1$ to $C_4$ alkoxy($C_1$ to $C_4$)alkyl group, Ar (Ar has the same meaning as above), —$L^1$—Ar (Ar and $L^1$ have the same meanings as above), Het (Het has the same meaning as above) or —$L^1$— Het (Het and $L^1$ have the same meanings as above), and $L^2$ represents —C(O)—, —C(S)—, —SO$_2$—, —S(O)—, —S—, —C(O)O—, —C(O)S—, —C(S)O—, —C(S)S— or —C(O)C(O)O—, —$L^3$—S—D$^{52}$ in which D$^{52}$ has the same meaning as above, and $L^3$ represents a $C_1$ to $C_6$ alkyl chain, a $C_2$ to $C_6$ alkenyl chain or a $C_2$ to $C_6$ alkynyl chain each of which may be substituted by one or two or more of a $C_1$ to $C_4$ haloalkyl group or a $C_1$ to $C_4$ alkyloxycarbonyl group and may be branched, —$L^3$—C(O)O—D$^{52}$ in which D$^{52}$ and $L^3$ have the same meanings as above, —C(O)—ND$^{52}$D$^{53}$ in which D$^{52}$ has the same meaning as above, and D$^{53}$ represents a hydrogen atom, a $C_1$ to $C_6$ alkyl group, a $C_1$ to $C_6$ alkoxy group, a $C_1$ to $C_4$ alkylsulfonyl group, Ar (Ar has the same meaning as above) or —$L^1$—Ar group (Ar and $L^1$ have the same meanings as above), and alternatively D$^{52}$ and D$^{53}$ together with a nitrogen group to which they are attached may form a 5- or 6-membered ring, —C(S)—ND$^{52}$D$^{53}$ in which D$^{52}$ and D$^{53}$ have the same meanings as above, —$L^3$—C(O)—ND$^{52}$D$^{53}$ in which D$^{52}$, D$^{53}$ and $L^3$ have the same meanings as above, —$L^3$—C(S)—ND$^{52}$D$^{53}$ in which D$^{52}$, D$^{53}$ and $L^3$ have the same meanings as above, P(O) (OD$^{52}$) (OD$^{53}$) in which D$^{52}$ and D$^{53}$ have the same meanings as above, —$L^3$—P(O) (OD$^{52}$) (OD$^{53}$) in which D$^{52}$, D$^{53}$ and $L^3$ have the same meanings as above, —$L^3$—CN in which $L^3$ has the same meaning as above, =CD$^{54}$—ND$^{52}$D$^{53}$ in which D$^{52}$ and D$^{53}$ have the same meanings as above, and D$^{54}$ represents a hydrogen atom, a halogen atom, a $C_1$ to $C_6$ alkyl group, a $C_1$ to $C_6$ alkoxy group, a $C_1$ to $C_4$ alkylthio group or Ar (Ar has the same meaning as above), —$L^2$—D$^{55}$ in which $L^2$ has the same meaning as above, and D$^{55}$ represents a $C_1$ to $C_6$ alkyl group, a $C_2$ to $C_6$ alkenyl group or a $C_2$ to $C_6$ alkynyl group each of which may be substituted by one or two or more of a $C_1$ to $C_4$ haloalkyl group or one or two or more of a $C_1$ to $C_4$ alkyloxycarbonyl group and may be branched, or —$L^1$—$SO_2$—$D^{56}$ in which $L^1$ has the same meaning as above, and $D^{56}$ represents a $C_1$ to $C_4$ alkyl group, and alternatively $D_a$ and $D_b$ together with a nitrogen atom to which they are attached may form a ring represented by

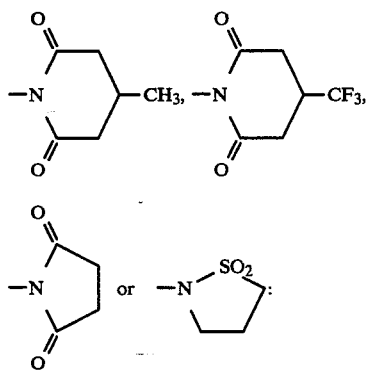

provided that except for the case where $D_a$ and $D_b$ both represent hydrogen atoms, the case where $D_a$ represents —$L^2$—$D^{52}$ in which $L^2$ represents —$SO_2$— and $D^{52}$ represents the $C_1$ to $C_4$ alkyl group or the $C_1$ to $C_3$ haloalkyl group, and $D_b$ represents the hydrogen atom, the $C_1$ to $C_4$ alkyl group, the $C_2$ to $C_5$ alkenyl group, the $C_3$ to $C_5$ alkynyl group, the $C_2$ to $C_5$ acyl group, the $C_1$ to $C_4$ alkylsulfonyl group or the ($C_1$ to $C_3$ alkoxy) $C_1$ to $C_2$ alkyl group are excluded.

The compound of the present invention can be used in treatment methods either of a soil treatment or a foliar treatment, as herbicides for upland field, paddy field and non-cultivated field.

As subjective weeds of the compound of the present invention, there may be mentioned broad-leaved weeds such as *Solanum nigrum, Datura nigrum, Abutilon theophrasti, Side spinosa, Ipomoea* spps. of *Ipomoea purpurea, Amaranthus lividus, Amaranthus vividis, Xanthium strumarium, Ambrosia artemisiaefolia, Helianthus annuus, Galinsoga ciliata, Cirsium arvense, Senecio vulgaris, Erigeron annus, Rorippa indica, Sinapis arvensis, Capsella Bursapastris, Polygonum Blumei, Polygonum convolvulus, Portulaca oleracea, Chenopodium album, Chenopodium ficifolium, Kochias coparia, Stellaria media, Veronica persica, Commelina communis, Lamium amplexicaule, Lamium purpureum, Euphorbia supina, Euphorbia maculata, Galium aparine, Rubiaakane, Viola arvensis, Sesbania exaltata, Cassia obtusifolia* and *Bidens pilosa*; Graminaceous weeds such as *Sorgham bicolor, Panicum dichotomiflorum, Sorphum halepense, Echinochloa crusgalli, Digitaria adscendens, Avena fatua, Eleusine indica, Setaria viridis* and *Alopecurus aequalis*; Cyperaceous weeds such as *Cyperus rotundus*; and *Alisma canaliculatum, Sagittaria trifolia, Sagittaria pygmaea, Cyperus difformis, Cyperus serotinus, Scirpus juncoides, Eleocharis kuroguwai, Lindemia pyxidaria, Monochoria Vaginalis, Potamogeton distinctus, Rotala indica* and *Echinochloa oryzicola*.

The compound of the present invention contains a compound which can be used safely to wheat, corn, barley, soybean, rice, cotton, sugar, beet, sorghum, etc. which are important crops.

Also, the compound of the present invention is available as a defoliant.

For applying the compound of the present invention as a herbicide, it may be generally applied by mixing with a suitable carrier such as a solid carrier, for example, clay, talc, bentonite, diatomaceous earth, white carbon, etc., or a liquid carrier, for example, water, alcohols including isopropanol, butanol, benzyl alcohol and furfuryl alcohol, aromatic hydrocarbons including toluene and xylene, ethers including anisol, ketones including cyclohexanone and isophoron, esters including butyl acetate, acid amides including N-methylpyrrolidone, or halogenated hydrocarbons including chlorobenzene and the like. If desired, by adding a surfactant, an emulsifier, a dispersant, a penetrating agent, a spreading agent, a thickening agent, an antifreezing agent, an anticaking agent, a stabilizer, etc., it can be provided practically in an optional formulation such as a liquid formulation, an emulsifiable concentrate, a wettable powder, a dry flowable formulation, a flowable formulation, a dust, a granule, etc.

The content of the compound of the present invention in the herbicide of the present invention may be an amount which develops the herbicidal activity and not particularly limited, but it is preferably 1 mg to 95 g per 100 g of the herbicide.

If necessary, the compound of the present invention may be mixed with any other herbicides, various insecticides, plant growth regulators, synergists, etc., and applied, when the formulation is prepared or applied.

Particularly, by mixing and applying with the other herbicides, a cost reduction by decreasing an applied dosage, an enlargement in weed control spectrum or an improvement in herbicidal activity due to synergistic effect of mixed agents can be expected. At this time, a plural known herbicides can be combined simultaneously. As a kind of a herbicide to be mixed with the compound of the present invention, there may be mentioned, for example, compounds described in Farm Chemicals Handbook, issued in 1990.

When the compound of the present invention is applied to the soybean, particularly preferred agents to be mixed with the compound of the present invention are trifluralin, pendimethalin, alachlor, metolachlor, metribuzin, linuron, chlorimuron ethyl, imazaquin, imazethapyr, dinoseb, bifenox, clomazone, etc.

When the compound of the present invention is mixed with the other agents, a mixing ratio (by weight) of the compound of the present invention to active components of the other agents is preferably 0.001 to 100:1 and a content proportion of the compound of the present invention in the mixed agents (herbicides) is preferably 1 mg to 95 g per 100 g of the herbicide.

An applied dosage of the compound of the present invention may vary depending on a locus to be applied, a time to be applied, a method for application, cultivated crops, etc., but generally it is suitable in an amount of about 0.0001 to 10 kg, preferably about 0.001 to 5 kg of active component per hectare (ha).

The compound of the present invention is a compound having the high herbicidal effect and the suitable residual activity with an extremely low dose, killing the weeds promptly after applying, having broad object of controlling the weeds, having many methods for application of agents, and showing substantially no chemical damage against the important crops.

BEST MODE FOR PRACTICING THE INVENTION

In the following, the present invention will be explained in more detail by referring to Examples, but the present invention is not limited by the following Examples so long as not exceeding the gist of the invention.

EXAMPLES

Example 1

Synthesis of
3-(4-chloro-2-fluoro-5-(2-thienylsulfonylamino)-phenyl)-1-methyl-6-trifluoromethyl-2,4(1H, 3H)-pyrimidinedione (Compound D-12)

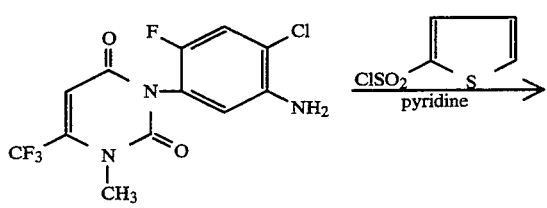

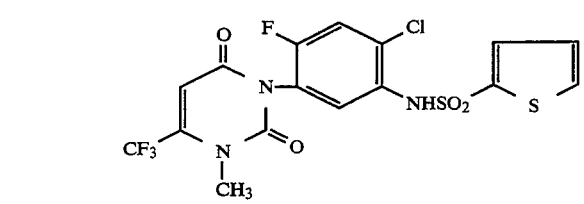

In 5 ml of pyridine was dissolved 0.32 g of 3-(5-amino-4-chloro-2-fluorophenyl)-1-methyl-6-trifluoromethyl-2,4(1H,3H)-pyrimidinedione, and then 0.19 g of 2-thiophensulfonyl chloride was added to the solution at 5° C. or lower. Thereafter, the temperature was increased to room temperature and the reaction was continued overnight. Then, pyridine was removed by distillation and the residue was dissolved in ethyl acetate. The solution was washed successively with water, diluted hydrochloric acid and a saturated saline solution, and dried over anhydrous sodium sulfate followed by removing ethyl acetate by distillation to obtain a crude product. This was washed with diisopropyl ether to obtain 0.3 g of the desired compound as white crystal.

Example 2

Synthesis of
3-(4-chloro-2-fluoro-5-(2,3,4,5-tetrahydroisothiazol-1,1-dioxide-2-yl)phenyl)-1-methyl-6-trifluoromethyl-2,4(1H, 3H)-pyrimidinedione (Compound D-15)

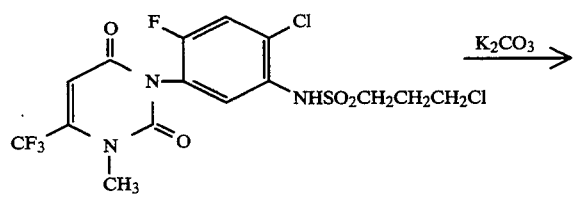

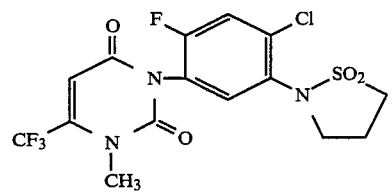

In 5 ml of N,N-dimethylformamide was dissolved 0.25 g of 3-(4-chloro-2-fluoro-5-(3-chloropropansulfonylamino)phenyl)-1-methyl-6-trifluoromethyl-2,4(1H,3H)-pyrimidinedione, and 0.08 g of anhydrous potassium carbonate was added thereto and the mixture was stirred at room temperature for 2 days. After removing N,N-dimethylformamide by distillation, the residue was dissolved in ethyl acetate, washed successively with water and a saturated saline solution, and dried over anhydrous sodium sulfate. By removing ethyl acetate by distillation, a crude product was obtained. This was purified by a preparative thin layer chromatography (developing solvent hexane:ethyl acetate=3:2) to obtain 0.1 g of the desired compound as white crystal.

Example 3

Synthesis of
3-(4-chloro-2-fluoro-5-(O,O-diethylphosphorylamino)-phenyl)-1-methyl-6-trifluoromethyl-2,4(1H, 3H)-pyrimidinedione (Compound D-16)

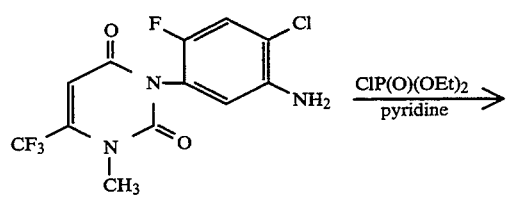

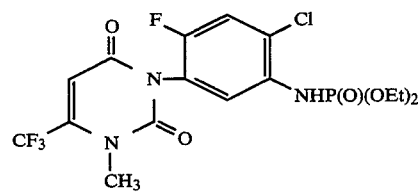

In 2 ml of pyridine was dissolved 0.50 g of 3-(5-amino-4-chloro-2-fluorophenyl)-1-methyl-6-trifluoromethyl-2,4(1H,3H)-pyrimidinedione, and then 0.22 ml of diethylchlorophosphate was added dropwise thereto at 5° C. or lower. Thereafter, the temperature was increased to room temperature and the reaction was continued overnight. Then, pyridine was removed by distillation and the residue was dissolved in ethyl acetate. The solution was washed successively with water, diluted hydrochloric acid and a saturated saline solution, and dried over anhydrous sodium sulfate followed by removing ethyl acetate by distillation to obtain a crude product. This was washed with diisopropyl ether to obtain 0.39 g of the desired compound as white crystal.

Example 4

Synthesis of 3-(4-chloro-2-fluoro-5-(methoxycarbonylaminophenyl)-1-methyl-6-trifluoromethyl-2,4(1H,3H)-pyrimidinedione (Compound D-22)

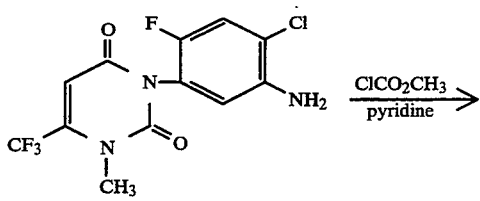

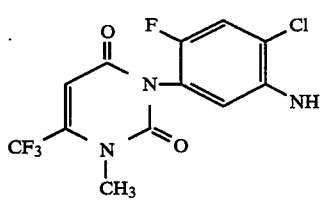

In 5 ml of pyridine was dissolved 0.38 g of 3-(5-amino-4-chloro-2-fluorophenyl)-1-methyl-6-trifluoromethyl-2,4(1H,3H)-pyrimidinedione, and then 0.11 g of methyl chloroformate was added thereto at 5° C. or lower. Thereafter, the temperature was increased to room temperature and the reaction was continued overnight. Then, pyridine was removed by distillation and the residue was dissolved in ethyl acetate. The solution was washed successively with water, diluted hydrochloric acid and a saturated saline solution, and dried over anhydrous sodium sulfate followed by removing ethyl acetate by distillation to obtain a crude product. This was washed with diisopropyl ether to obtain 0.28 g of the desired compound as white crystal.

Example 5

Synthesis of 3-(4-chloro-2-fluoro-5-(N-methyl)ethoxycarbonylaminophenyl)-1-methyl-6-trifluoromethyl-2,4(1H,3H)-pyrimidinedione (Compound D-24)

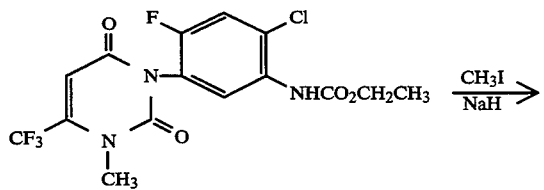

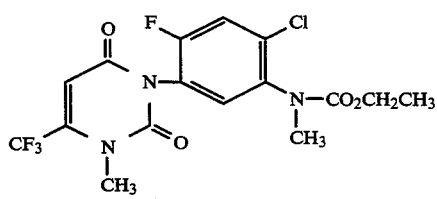

After adding 0.38 g of 3-(4-chloro-5-ethoxycarbonylamino-2-fluorophenyl)-1-methyl-6-trifluoromethyl-2,4-(1H,3H)-pyrimidinedione to a suspension of 0.04 g of sodium hydride in tetrahydrofuran (10 ml), 0.06 ml of methyl iodide was added dropwise thereto. After 2 hours, ice-water was added thereto and the mixture was extracted with ethyl acetate. The ethyl acetate layer was washed with a saturated saline solution and dried over anhydrous sodium sulfate followed by removing ethyl acetate by distillation to obtain a crude product. This was purified by a preparative thin layer chromatography (developing solvent hexane:ethyl acetate=5:2) to obtain 0.22 g of the desired compound as white crystal.

Example 6

Synthesis of 3-(5-acetylamino-4-chloro-2-fluorophenyl)-1-methyl-6-trifluoromethyl-2,4(1H,3H)-pyrimidinedione (Compound D-17)

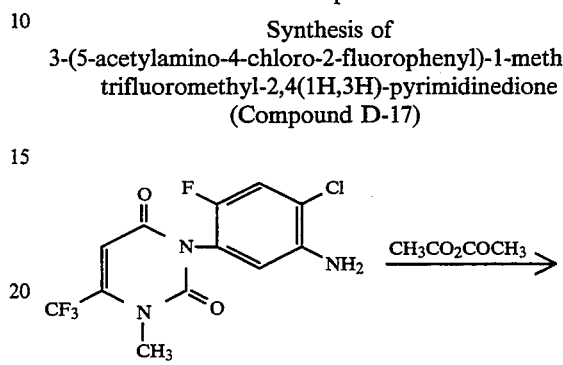

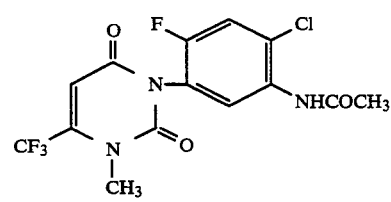

In 5 ml of benzene was dissolved 2.00 g of 3-(5-amino-4-chloro-2-fluorophenyl)-1-methyl-6-trifluoromethyl-2,4(1H,3H)-pyrimidinedione, and 0.61 ml of anhydrous acetic acid was added thereto and the mixture was refluxed for one hour. Benzene was removed by distillation to obtain a crude product. This was washed with hexane to obtain 2.20 g of the desired compound as white crystal.

Example 7

Synthesis of 3-(4-chloro-2-fluoro-5-formylaminophenyl)-1-methyl-6-trifluoromethyl-2,4(1H,3H)-pyrimidinedione (Compound D-21)

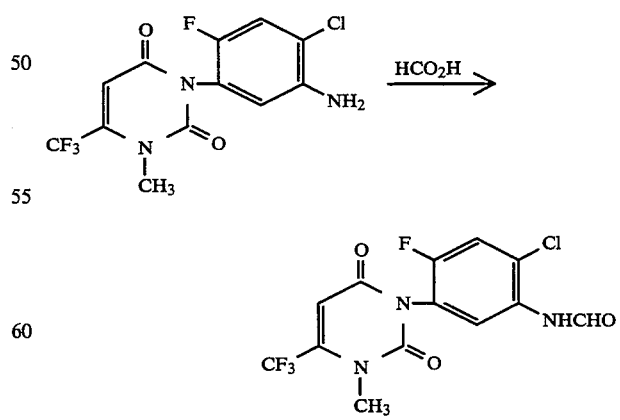

After stirring 0.080 g of formic acid and 0.180 g of anhydrous acetic acid at 60° C. for one hour, the mixture was cooled to 30° C. To the mixture was added a mixture of 0.500 g of 3-(5-amino-4-chloro-2-fluorophenyl) -1-methyl-6-trifluoromethyl-2,4(1H,3H)-pyrimidinedione and 4 ml of chloroform, and the mixture was stirred for one hour. After refluxing for further one hour, 1.3 ml of formic acid was added to the mixture and the mixture was refluxed for one hour. The solvent was removed by distillation using a vacuum pump to obtain a crude product. This was washed with hexane and dried to obtain 0.510 g of the desired compound as brownish white crystal.

Example 8

Synthesis of 3-(4-chloro-5-ethoxalylamino-2-fluorophenyl)-1-methyl-6-trifluoromethyl-2,4(1H,3H)-pyrimidinedione (Compound D-35)

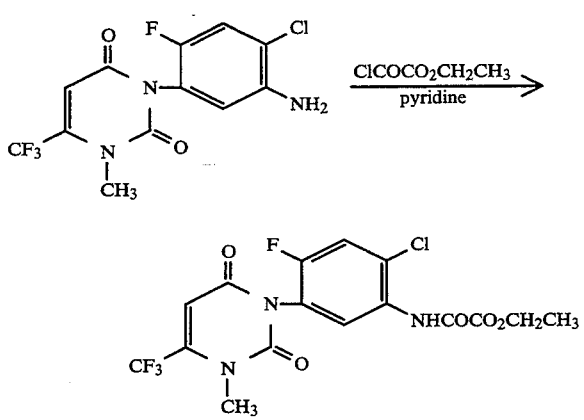

In 5 ml of pyridine was dissolved 0.39 g of 3-(5-amino-4-chloro-2-fluorophenyl)-1-methyl-6-trifluoromethyl-2,4(1H,3H)-pyrimidinedione, and 0.17 g of ethyl oxalyl chloride was added thereto at 5° C. or lower. Thereafter, the temperature was increased to room temperature and the reaction was continued overnight. Then, pyridine was removed by distillation and the residue was dissolved in ethyl acetate. The mixture was washed successively with water, diluted hydrochloric acid and a saturated saline solution, and dried over anhydrous sodium sulfate followed by removing ethyl acetate by distillation to obtain a crude product. This was washed with diisopropyl ether to obtain 0.29 g of the desired compound as white crystal.

Example 9

Synthesis of 3-(4-chloro-2fluoro-5-(3-methansulfonylureyen-1-yl)phenyl)-1)-1-methyl-6-trifluoromethyl-2,4(1H,3H)-pyrimidinedione (Compound D-33)

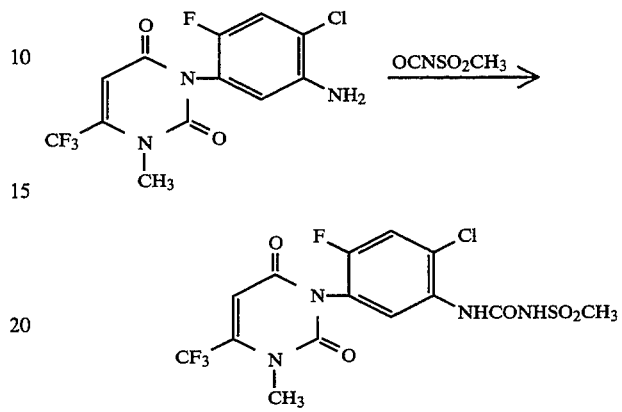

In 10 ml of dry tetrahydrofuran was dissolved 0.34 g of 3-(5-amino-4-chloro-2-fluorophenyl)-1-methyl-6-trifluoromethyl-2,4(1H,3H)-pyrimidinedione, and 0.15 g of methylsulfonylisocyanate was added thereto and the mixture was stirred at 30°–40° C. for 2 hours. After cooling by allowing to stand, precipitated crystals were collected by filtration and washed with n-hexane to obtain 0.28 g of the desired compound as white crystal.

Example 10

Synthesis of 3-(4-chloro-5-(2,6-dioxo-4-trifluoromethylpiperidin-1-yl)-2-fluorophenyl)-1-methyl-6-trifluoromethyl-2,4(1H,3H)-pyrimidinedione (Compound D-40)

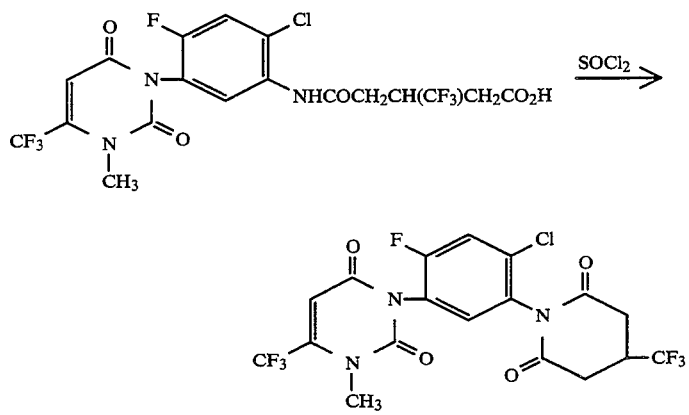

To a solution of 0.50 g of 4-(N-(2-chloro-4-fluoro-5(1-methyl-6-trifluoromethyl-2,4(1H,3H)-pyrimidinedion-3-yl)phenyl)carbamoyl)-3-trifluoromethylbutyric acid and 7 ml of dry tetrahydrofuran was added dropwise 0.23 g of thionyl chloride at room temperature. After stirring for 2 hours under reflux, the temperature was cooled to room temperature, and the solvent was removed by distillation under reduced pressure. The resulting crude product was extracted with ethyl acetate, washed successively with water, a saturated aqueous solution of sodium hydrogen carbonate and a saturated saline solution, and dried over anhydrous sodium sulfate followed by removing ethyl acetate by distillation to obtain 0.50 g of the desired compound as crystal.

Example 11

Synthesis of 4-(N-(2-chloro-4-fluoro-5-(1-methyl-6-trifluoromethyl-2,4(1H,3H)-pyrimidinedion-3-yl)phenyl)carbamoyl)-3-trifluoromethylbutyric acid (Compound D-37)

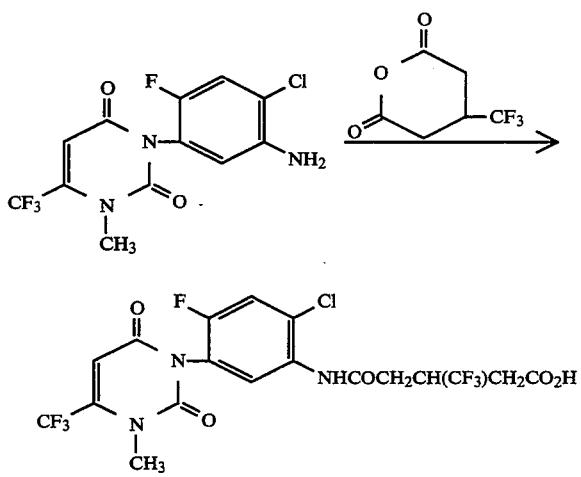

A mixture of 0.50 g of 3-(5-amino-4-chloro-2-fluorophenyl)-1-methyl-6-trifluoromethyl-2,4(1H,3H)-pyrimidinedione, 0.27 g of 3-trifluoromethylglutaric anhydride and 6 ml of toluene was stirred at 100° C. for one hour. After cooling to room temperature, the solvent was removed by distillation under reduced pressure to obtain 0.7 g of the desired compound as crystal.

Example 12

Synthesis of methyl 4-(N-(2-chloro-4-fluoro-5-(1-methyl-6-trifluoromethyl-2,4(1H,3H)-pyrimidinedion-3-yl)phenyl)carbamoyl)-3-trifluoromethylbutyrate (Compound D-38)

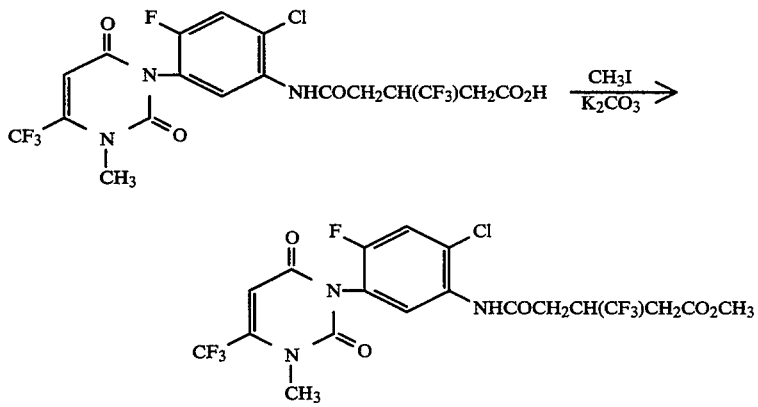

To a mixture of 0.20 g of 4-(N-(2-chloro-4-fluoro-5-(1-methyl-6-trifluoromethyl-2,4(1H,3H)-pyrimidinedion-3-yl)phenyl)carbamoyl)-3-trifluoromethylbutyric acid, 0.06 g of potassium carbonate and 4 ml of N,N-dimethylformamide was added 0.05 g of methyl iodide at room temperature and the mixture was stirred at room temperature for 3 hours. The mixture was diluted with ethyl acetate and washed successively with water and a saturated saline solution, and dried over anhydrous sodium carbonate followed by removing ethyl acetate by distillation to obtain 0.44 g of the desired compound as crystal.

Example 13

Synthesis of 3-(5-(N-acetyl)propargylamino-4-chloro-2-fluorophenyl)-1-methyl-6-trifluoromethyl-2,4(1H,3H)-pyrimidinedione (Compound D-20)

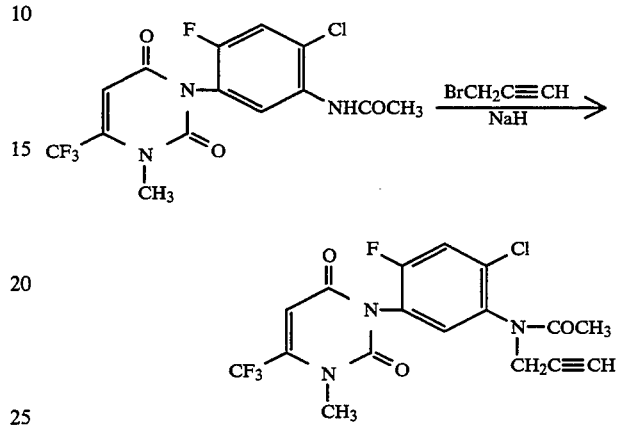

A mixture of 1.05 g of 3-(5-acetylamino-4-chloro-2-fluorophenyl)-1-methyl-6-trifluoromethyl-2,4-(1H,3H)-pyrimidinedione and 9 ml of N,N-dimethylformamide was cooled to 0° C., and 0.13 g of sodium hydride was added to the solution and the mixture was stirred until the temperature was increased to room temperature. Then, 0.33 g of propargyl bromide was added to the mixture and the mixture was stirred at room temperature for 2 days. The mixture was diluted with ethyl acetate and washed successively with water and a saturated saline solution, and dried over anhydrous sodium carbonate followed by removing ethyl acetate by distillation to obtain 0.93 g of the desired compound as crystal.

Example 14

Synthesis of
3-(4-chloro-2-fluoro-5-(N-methanesulfonyl)methoxycarbonylmethylaminophenyl)-1-methyl-6-trifluoromethyl-2,4(1H,3H)-pyrimidinedione (Compound D-13)

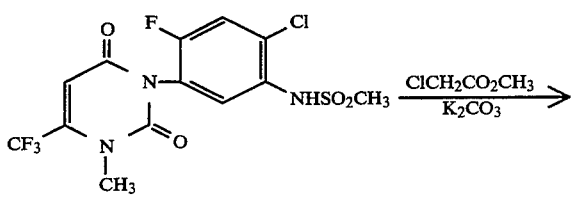

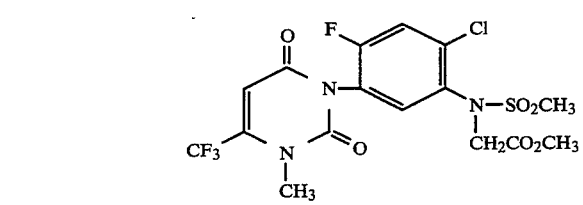

In 5 ml of N,N-dimethylformamide was dissolved 0.50 g of 3-(4-chloro-2-fluoro-5-methanesulfonylaminophenyl)-1-methyl-6-trifluoromethyl-2,4(1H,3H)-pyrimidinedione, and 0.17 g of anhydrous potassium carbonate and 0.11 ml of methyl chloroacetate were added thereto and the mixture was stirred at room temperature overnight. After removing N,N-dimethylformamide by distillation, the residue was dissolved in ethyl acetate, washed successively with water and a saturated saline solution, and dried over anhydrous sodium sulfate. By removing ethyl acetate by distillation, a crude product was obtained. This was purified by a preparative thin layer chromatography (developing solvent hexane: ethyl acetate=1:1) to obtain 0.19 g of the desired compound as colorless viscous oily product.

Example 15

Synthesis of
3-(4-chloro-5-(N-ethanesulfonyl)ethoxycarbonylmethylamino-2-fluorophenyl)-1-methyl-6-trifluoromethyl-2,4(1H,3H)-pyrimidinedione (Compound D-14)

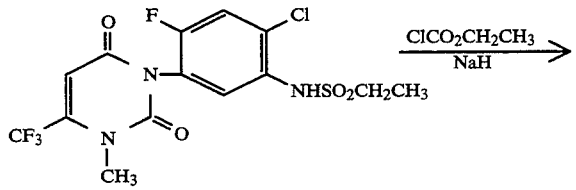

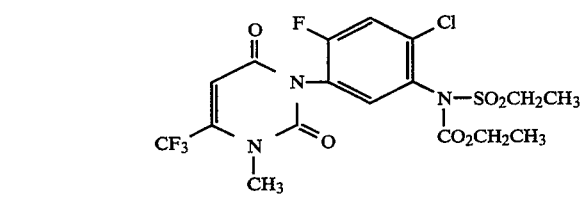

In 5 ml of N,N-dimethylformamide was dissolved 0.30 g of 3-(4-chloro-5-ethanesulfonylamino-2-fluorophenyl)-1-methyl-6-trifluoromethyl-2,4(1H,3H)-pyrimidinedione, and 0.03 g of 60% sodium hydride and 0.10 g of ethyl chloroformate were added thereto and the mixture was stirred at room temperature for 4 days. After removing N,N-dimethylformamide by distillation, the residue was dissolved in ethyl acetate, washed successively with water and a saturated saline solution, and dried over anhydrous sodium sulfate. By removing ethyl acetate by distillation, a crude product was obtained. This was purified by a preparative thin layer chromatography (developing solvent hexane: ethyl acetate=3:2) to obtain 0.10 g of the desired compound as white crystal.

Example 16

Synthesis of
3-(5-benzensulfinamino-4-chlorophenyl)-1-methyl-6-trifluoromethyl-2,4(1H,3H)-pyrimidinedione (Compound D-46)

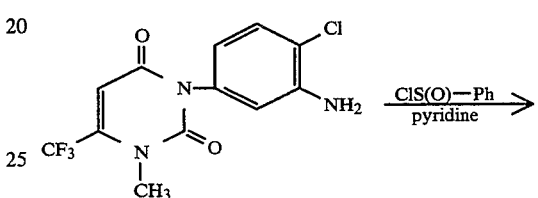

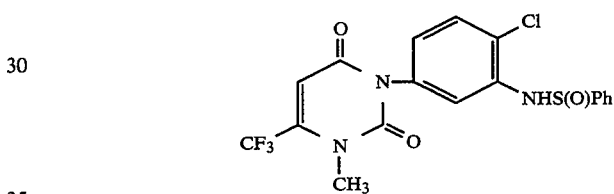

In 5 ml of pyridine was dissolved 0.34 g of 3-(3-amino-4-chlorophenyl-1-methyl-6-trifluoromethyl-2,4(1H,3H)pyrimidinedione, and 0.19 g of benzenesulfinyl chloride was added thereto at 5° C. or lower. After reacting the mixture for one hour, pyridine was removed by distillation and the residue was dissolved in ethyl acetate. The reaction mixture was washed successively with water, diluted hydrochloric acid and a saturated saline solution, and dried over anhydrous sodium sulfate followed by removing ethyl acetate by distillation to obtain a crude product. This was purified by a preparative thin layer chromatography (developing solvent hexane: ethyl acetate=3:1) and recrystallized from n-hexane to obtain 0.03 g of the desired compound as white crystal.

Example 17

Synthesis of
3-(4-chloro-2-fluoro-5-trichloromethylthioaminophenyl)-1-methyl-6-trifluoromethyl-2,4(1H,3H)-pyrimidinedione (Compound D-42)

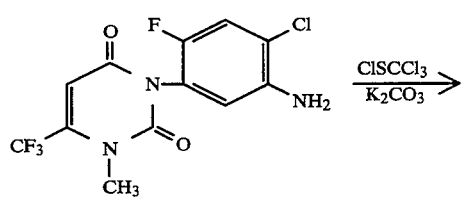

-continued

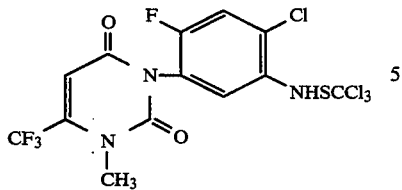

In 5 ml of N,N-dimethylformamide was dissolved 0.73 g of 3-(5-amino-4-chloro-2-fluorophenyl)-1-methyl-6-trifluoromethyl-2,4(1H,3H)-pyrimidinedione, and 0.33 g of anhydrous sodium carbonate and 0.44 g of perchloromethylmercaptane were added thereto and the mixture was stirred at room temperature for 1.5 hours. After removing N,N-dimethylformamide by distillation, the residue was dissolved in ethyl acetate, washed successively with water and a saturated saline solution, and dried over anhydrous sodium sulfate. By removing ethyl acetate by distillation, a crude product was obtained. This was purified by a preparative thin layer chromatography (developing solvent hexane: ethyl acetate=3:1) to obtain 0.79 g of the desired compound as colorless viscous oily product.

Example 18

Synthesis of 3-(4-chloro-2-fluoro-5-trichloromethanesulfinaminophenyl)-1-methyl-6-trifluoromethyl-2,4(1H,3H)-pyrimidinedione (Compound D-43)

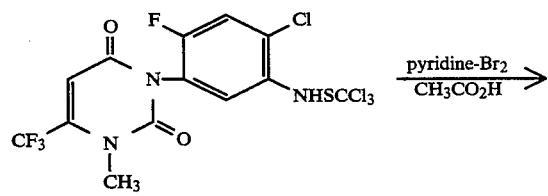

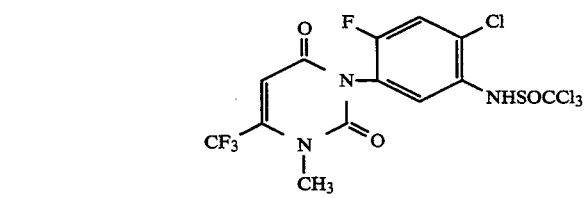

In 10 ml of 70% acetic acid was dissolved 0.29 g of 3-(4-chloro-2-fluoro-5-trichloromethylthioaminophenyl)-1-methyl-6-trifluoromethyl-2,4(1H,3H)-pyrimidinedione, and 0.14 g of pyridine-bromine complex was added thereto and the mixture was stirred at room temperature for one hour. After removing acetic acid by distillation, the residue was dissolved in ethyl acetate, washed successively with water, a saturated aqueous solution of sodium hydrogen carbonate and a saturated saline solution, and dried over anhydrous sodium sulfate. By removing ethyl acetate by distillation, a crude product was obtained. This was purified by a preparative thin layer chromatography (developing solvent hexane: ethyl acetate=5:1) to obtain 0.05 g of the desired compound as white crystal.

Example 19

Synthesis of 3-(4-chloro-2-fluoro-5-(2-thenoylamino)phenyl)-1-methyl-6-trifluoromethyl-2,4(1H,3H)-pyrimidinedione (Compound D-45)

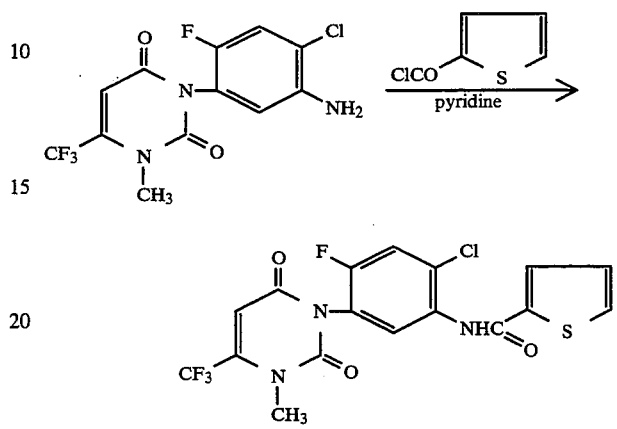

In 5 ml of pyridine was dissolved 0.34 g of 3-(5-amino-4-chloro-2-fluorophenyl)-1-methyl-6-trifluoromethyl-2,4(1H,3H)-pyrimidinedione, and 0.17 g of 2-thiophencarbonyl chloride was added thereto at 5° C. or lower. Thereafter, the temperature was increased to room temperature and the reaction was continued overnight. Then, pyridine was removed by distillation and the residue was dissolved in ethyl acetate. The solution was washed successively with water, diluted hydrochloric acid and a saturated saline solution, and dried over anhydrous sodium sulfate followed by removing ethyl acetate by distillation to obtain a crude product. This was washed with diisopropyl ether to obtain 0.30 g of the desired compound as white crystal.

Example 20

Synthesis of 3-(4-chloro-2-fluoro-5-(N,N-dimethylmethylideneamino)phenyl)-1-methyl-6-trifluoromethyl-2,4(1H,3H)-pyrimidinedione (Compound D-44)

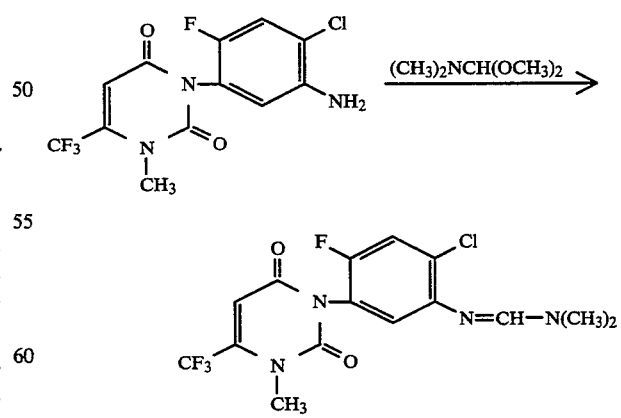

In 2 ml of N,N-dimethylformamide was dissolved 0.40 g of 3-(5-amino-4-chloro-2-fluorophenyl)-1-methyl-6-trifluoromethyl-2,4(1H,3H)-pyrimidinedione, and 0.14 g of N,N-dimethylformamidedimethylacetal was added thereto. After reacting the mixture at 80° C. for 10 hours, N,N-dimethylformamide was removed by distillation to obtain 0.50 g of the desired compound as brownish viscous oily product.

The compounds of the present invention synthesized in accordance with the above scheme or Examples including the compounds synthesized in the above Examples are shown in Tables 1 and 2 with their chemical structures and physical properties, respectively.

TABLE 1

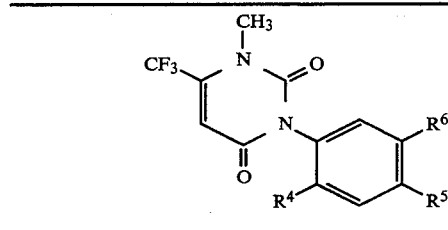

| Compound No. | $R^4$ | $R^5$ | $R^6$ |
|---|---|---|---|
| D-1 | F | Cl | $NHSO_2C_6H_5$ |
| D-2 | F | Cl | $N(CH_3)SO_2C_6H_5$ |
| D-3 | F | Cl | $NHSO_2$-(4-F—$C_6H_4$) |
| D-4 | F | Cl | $NHSO_2$-(4-Cl—$C_6H_4$) |
| D-5 | F | Cl | $NHSO_2$-(4-$OCH_3$—$C_6H_4$) |
| D-6 | F | Cl | $NHSO_2$-(2-$CH_3$—$C_6H_4$) |
| D-7 | F | Cl | $NHSO_2$-(3-$CH_3$—$C_6H_4$) |
| D-8 | F | Cl | $NHSO_2$-(4-$CH_3$—$C_6H_4$) |
| D-9 | F | Cl | $NHSO_2$-(2-$NO_2$—$C_6H_4$) |
| D-10 | F | Cl | $NHSO_2$-(3-$NO_2$—$C_6H_4$) |
| D-11 | F | Cl | $NHSO_2$-(4-$NO_2$—$C_6H_4$) |
| D-12 | F | Cl | $NHSO_2$-$Q_4$ |
| D-13 | F | Cl | $N(SO_2CH_3)CH_2CO_2CH_3$ |
| D-14 | F | Cl | $N(SO_2C_2H_5)CO_2C_2H_5$ |
| D-15 | F | Cl | $Q_{38}$ |
| D-16 | F | Cl | $NHP(O)(OC_2H_5)_2$ |
| D-17 | F | Cl | $NHCOCH_3$ |
| D-18 | F | Cl | $NHCOCCl_3$ |
| D-19 | F | Cl | $NHCOCF_3$ |
| D-20 | F | Cl | $N(CH_2C{\equiv}CH)COCH_3$ |
| D-21 | F | Cl | $NHCHO$ |
| D-22 | F | Cl | $NHCO_2CH_3$ |
| D-23 | F | Cl | $NHCO_2C_2H_5$ |
| D-24 | F | Cl | $N(CH_3)CO_2C_2H_5$ |
| D-25 | F | Cl | $NHCO_2CH_2CH_2CH_3$ |
| D-26 | F | Cl | $NHCO_2(CH_2)_3CH_3$ |
| D-27 | F | Cl | $NHCO_2CH_2CH(CH_3)_2$ |
| D-28 | F | Cl | $NHCO_2CH_2CH_2Cl$ |
| D-29 | F | Cl | $NHCO_2CH_2CCl_3$ |
| D-30 | F | Cl | $NHCO_2CH_2CH_2OCH_3$ |
| D-31 | F | Cl | $NHCO_2CH_2C_6H_5$ |
| D-32 | F | Cl | $NHCO_2C_6H_5$ |
| D-33 | F | Cl | $NHCONHSO_2CH_3$ |
| D-34 | F | Cl | $NHCONHCH_3$ |
| D-35 | F | Cl | $NHCOCO_2C_2H_5$ |
| D-36 | F | Cl | $NHCOCH_2CH(CH_3)CH_2CO_2H$ |
| D-37 | F | Cl | $NHCOCH_2CH(CF_3)CH_2CO_2H$ |
| D-38 | F | Cl | $NHCOCH_2CH(CF_3)CH_2CO_2CH_3$ |
| D-39 | F | Cl | 4-Me-$Q_{30}$ |
| D-40 | F | Cl | 4-$CF_3$-$Q_{30}$ |
| D-41 | F | Cl | $Q_{43}$ |
| D-42 | F | Cl | $NHSCCl_3$ |
| D-43 | F | Cl | $NHSOCCl_3$ |
| D-44 | F | Cl | $N{=}CHN(CH_3)_2$ |
| D-45 | F | Cl | $NHCO$-$Q_4$ |
| D-46 | H | Cl | $NHSOC_6H_5$ |
| D-47 | Cl | F | $NHCOCH_2CH(CF_3)CH_2CO_2C_2H_5$ |
| D-48 | H | Cl | $NHSO_2C_6H_5$ |
| D-49 | F | Cl | $NHSO_2$-(2-$CO_2C_2H_5$—$C_6H_4$) |
| D-50 | F | Cl | $NHC(O)SCH_3$ |
| D-51 | F | Cl | $NHCO_2CH_2$-(4-F—$C_6H_4$) |
| D-52 | F | Cl | $NHCO_2CH_2$-(4-Cl—$C_6H_4$) |
| D-53 | F | Cl | $NHCO_2CH_2$-(4-$CH_3$—$C_6H_4$) |
| D-54 | F | Cl | $NHCO_2CH_2C(CH_3)_3$ |
| D-55 | F | Cl | $NHC(O)SCH_2C_6H_5$ |
| D-56 | F | F | $NHSO_2C_6H_5$ |
| D-57 | Cl | Cl | $NHSO_2C_6H_5$ |
| D-58 | H | Cl | $NHCO_2CH_3$ |
| D-59 | F | F | $NHCO_2CH_3$ |
| D-60 | Cl | Cl | $NHCO_2CH_3$ |

TABLE 1-continued

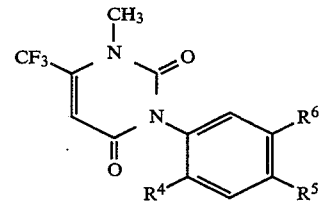

| Compound No. | $R^4$ | $R^5$ | $R^6$ |
|---|---|---|---|
| D-61 | F | Br | $NHCO_2C_2H_5$ |
| D-62 | F | Br | $NHSO_2C_6H_5$ |
| D-63 | F | Cl | $NHCO_2CH_2$-(4-$CH_3O$—$C_6H_4$) |
| D-64 | F | Cl | $NHCO_2CH_2$-(3-$CH_3$—$C_6H_4$) |
| D-65 | F | Cl | $NHCO_2CH_2$-(2-$CH_3$—$C_6H_4$) |
| D-66 | F | Br | $NHCO_2CH_3$ |
| D-67 | F | Br | $NHCO_2CH_2CH_2CH_3$ |
| D-68 | H | Br | $NHCO_2CH_3$ |
| D-69 | F | Br | $NHCO_2CH_2C_6H_5$ |
| D-70 | F | Cl | $NHCO_2CH_2$-(4-$C_2H_5$—$C_6H_4$) |
| D-71 | F | Cl | $NHCO_2CH_2$-(4-$C(CH_3)_3$—$C_6H_4$) |
| D-72 | F | Cl | $NHCO_2CH_2$-(4-$CF_3$—$C_6H_4$) |
| D-73 | F | Cl | $NHCO_2CH_2$-(4-$NO_2$—$C_6H_4$) |
| D-74 | F | Cl | $NHCO_2CH_2$-$Q_1$ |
| D-75 | F | Cl | $NHCO_2CH_2$-$Q_4$ |
| D-76 | F | Cl | $NHCO_2CH(CH_3)C_6H_5$ |
| D-77 | F | Cl | $NHCO_2CH_2CH_2C_6H_5$ |
| D-78 | F | Cl | $NHCO_2CH_2CF_3$ |
| D-79 | F | Cl | $NHCO_2CH_2$-(cyclopentyl) |
| D-80 | F | Cl | $NHCO_2CH_2CH{=}CHCH_3$ (trans) |
| D-81 | F | Cl | $NHCONHCH_2C_6H_5$ |
| D-82 | F | Cl | $NHCO_2CH_2CH{=}CH_2$ |
| D-83 | F | Cl | $NHCO_2CH_2CH{=}CHC_6H_5$ |
| D-84 | F | Cl | $NHCO_2CH_2$-$Q_2$ |
| D-85 | F | Cl | $NHCO_2CH_2$-$Q_3$ |
| D-86 | F | Cl | $NHCO_2CH_2$-$Q_{48}$ |
| D-87 | F | Cl | $NHCO_2CH_2$-($\beta$-naphthyl) |
| D-88 | F | Cl | $NHCO_2$-(4-$CH_3$—$C_6H_4$) |
| D-89 | F | Cl | $NHCON(CH_3)CH_2C_6H_5$ |
| D-90 | F | Cl | $NHCO$-$Q_{32}$ |
| D-91 | F | Cl | $NHC(S)OCH_3$ |
| D-92 | F | Cl | $NHSO_2CH_2C_6H_5$ |
| D-93 | F | Cl | $NHC(S)SCH_3$ |
| D-94 | F | Cl | $NHC(S)OCH_2C_6H_5$ |
| D-95 | F | Cl | $N(CHO)CH_2CO_2CH_3$ |
| D-96 | F | Cl | $NHCH_2CO_2CH_3$ |
| D-97 | F | Cl | $NHCH(CH_3)CO_2CH_3$ |
| D-98 | F | Cl | $NHCH(CH_3)CO_2C_2H_5$ |
| D-99 | F | Cl | $NHCH_2P(O)(OC_2H_5)_2$ |
| D-100 | F | Cl | $NHCH_2SCH_3$ |
| D-101 | F | Cl | $NHCH_2SO_2CH_3$ |
| D-102 | F | Cl | $NHCH_2CN$ |
| D-103 | F | Cl | $NHCO_2CH_2$-(2,4-$(CH_3)_2$—$C_6H_3$) |
| D-104 | F | Cl | $NHCO_2CH_2$-(3,4-$(CH_3)_2$—$C_6H_3$) | in which Q1, Q2, Q3, Q4, Q30, Q32, Q38, Q43 and Q48 are as shown below.

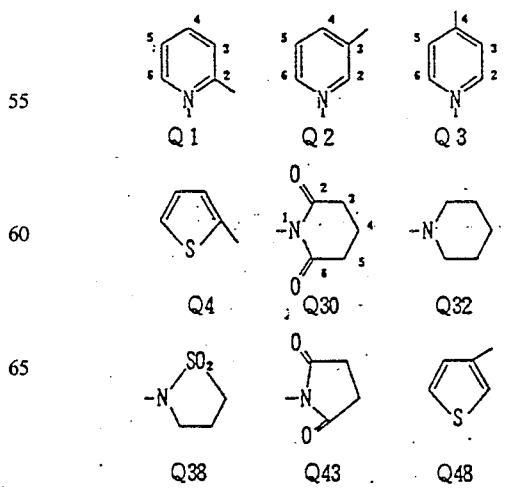

TABLE 2 -continued

| Compound No. | [solvent] | Physical property | |
|---|---|---|---|
| | 3.60(3H, s), 6.35(1H, s), 7.12(1H, d, J=8Hz), 7.39–7.81(7H, m) [CDCl₃] | Melting point | 188–190° C. |
| | 3.18(3H, s), 3.53(3H, s), 6.33(1H, s), 7.05–7.83(7H, m) [CDCL₃] | Melting point | 148–150° C. |
| D - 3 | 3.54(3H, s), 6.36(1H, s), 6.93–7.29(4H, m), 7.62–7.88(3H, m) [CDCL₃] | Melting point | 190–192° C. |
| D - 4 | 3.52(3H, s), 6.36(1H, s), 6.98–7.80(7H, m) [CDCL₃] | Melting point | 211–212° C. |
| D - 5 | 3.52(3H, s), 3.77(3H, s), 6.28(1H, s), 6.70–7.16(4H, m), 7.48–7.69(3H, m) [CDCL₃] | Melting point | 178–179° C. |
| D - 6 | 2.63(3H, s), 3.52(3H, s), 6.37(1H, s), 6.90–7.80(7H, m) [CDCL₃] | Melting point | 183–185° C. |
| D - 7 | 2.34(3H, s), 3.52(3H, s), 6.39(1H, s), 6.87–7.72(7H, m) [CDCL₃] | Melting point | 182–184° C. |
| D - 8 | 2.38((3H, s), 3.57(3H, s), 6.37(1H, s), 7.08–7.33(3H, m), 7.57–7.78(4H, m) [CDCL₃] | Melting point | 149–195° C. |
| D - 9 | 3.54(3H, s), 6.27(1H, s), 7.01–7.25(1H, m), 7.53–7.90(6H, m) [CDCL₃] | Glass like oily product | |
| D - 10 | 3.56(3H, s), 6.37(1H, s), 7.02–8.80(6H, m) [CDCL₃] | Glass like oily product | |
| D - 11 | 3.57(3H, s), 6.29(1H, s), 7.00–7.25(2H, m) 7.57–8.25(5H, m) [CDCL₃] | Melting point | 210–212° C. |
| D - 12 | 3.58(3H, s), 6.30(1H, s), 6.93–7.31(3H, m), 7.45–7.82(3H, m) [CDCL₃] | Melting point | 173–174° C. |
| D - 13 | 3.11(3H, s), 3.53(3H, s), 3.71(3H, s), 4.12(2H, s), 6.34(1H, s), 7.41(1H, d, J=9Hz), 7.80(1H, d, J=7Hz) [CDCL₃] | Viscous oily product | |
| D - 14 | 1.36(3H, t, J=7Hz), 1.48(3H, t, J=7Hz), 3.57(3H, s), 3.80(2H, q, J=7Hz), 4.27(2H, q, J=7Hz), 6.21(1H, s), 7.31(1H, s), 7.47(1H, d, J=2Hz) [CDCL₃] | Melting point | 155–157° C. |
| D - 15 | 2.52(2H, q, J=6Hz), 3.12–3.79(4H, m), 3.47(3H, s), 6.19(1H, s), 7.24(1H, d, J=3Hz), 7.31(1H, br s), 7.41(1H, d, J=7Hz) [CDCL₃] | Melting point | 192–193° C. |
| D - 16 | 1.20(6H, t, J=7Hz), 3.38(3H, s), 2.97(4H, dq, J=7Hz), 5.41(1H, d, J=7Hz), 6.12(1H, s), 7.04(1H, d, J=9Hz), 7.06(1H, d, J=7Hz) [CDCL₃] | Melting point | 130–132° C. |
| D - 17 | 2.15(3H, s), 3.47(3H, s), 6.54(1H, s), 7.70(1H, d, J=9Hz), 7.90(1H, d, J=8Hz), 9.56(1H, br s) [d₆-DMSO] | Melting point | 263–266° C. |
| D - 18 | 3.45(3H, s), 6.2(1H, s), 7.25(1H, d, J=9Hz), 8.13(1H, d, J=7Hz), 8.86(1H, br s) [CDCL₃] | Viscous oily product | |
| D - 19 | 3.44(3H, s), 6.21(1H, s), 7.22(1H, d, J=9Hz), 8.04(1H, d, J=7Hz), 8.44(1H, br s) [CDCL₃] | Melting point | 144–145° C. |

TABLE 2-continued

| Compound No. | $^1$H-NMR δ [solvent] | | Physical property |
|---|---|---|---|
| D - 20 | 1.87(3H, s), 2.20(1H, t, J=2Hz), 3.53(3H, s), 3.62–4.11(1H, m), 4.78–5.21(1H, m), 6.28(1H, s), 7.28(1H, d, J=7Hz), 7.35(1H, d, J=10Hz) [CDCL$_3$] | Melting point | 169–171° C. |
| D - 21 | 3.42(3H, s), 6.28(1H, s), 7.34(1H, d, J=10Hz), 8.17(1H, d, J=8Hz), 8.27(1H, br s), 9.67(1H, br s), [d$_6$-DMSO] | Melting point | 268–270° C. |
| D - 22 | 3.51(3H, s), 3.72(3H, s), 6.30(1H, s), 7.10(1H, br s), 7.27(1H, d, J=9Hz), 8.18(1H, d, J=7Hz) [CDCL$_3$] | Melting point | 136–138° C. |
| D - 23 | 1.26(3H, t, J=7Hz), 3.37(3H, s), 4.16(2H, q, J=7Hz), 6.45(1H, s), 7.57(1H, d, J=9Hz), 7.77(1H, d, J=7Hz), 9.10(1H, br s) [d$_6$-DMSO] | Melting point | 153–155° C. |
| D - 24 | 1.16(1H, t, J=7Hz), 3.16(3H, s), 3.49(3H, s), 3.51(2H, q, J=7Hz), 6.24(1H, s), 7.07(1H, d, J=7Hz), 7.23(1H, d, J=9Hz) [CDCL$_3$] | Melting point | 144–146° C. |
| D - 25 | 0.94(3H, t, J=7Hz), 1.70(2H, m), 3.47(3H, s), 4.04(2H, t, J=7Hz), 6.21(1H, s), 6.95(1H, br s), 7.14(1H, d, J=9Hz), 8.06(1H, d, J=7Hz) [CDCL$_3$] | Melting point | 152–154° C. |
| D - 26 | 0.98(3H, t, J=6Hz), 1.18–1.73(4H, m), 3.48(3H, s), 4.12(2H, t, J=6Hz), 6.25(1H, s), 6.98(1H, br s), 7.16(1H, d, J=9Hz), 8.11(1H, d, J=7Hz) [CDCL$_3$] | Melting point | 117–118° C. |
| D - 27 | 0.98(6H, d, J=6Hz), 1.18–2.25(1H, m), 3.50(3H, s), 3.91(2H, s, J=6Hz), 6.24(1H, s), 7.00(1H, br s), 7.18(1H, d, J=9Hz), 8.11(1H, d, J=7Hz) [CDCL$_3$] | Melting point | 129–131° C. |
| D - 28 | 3.50(3H, s), 3.67(2H, t, J=6Hz), 4.38(2H, t, J=6Hz), 6.24(1H, s), 7.09(1H, br s), 7.18(1H, d, J=9Hz), 8.08(1H, d, J=7Hz) [CDCL$_3$] | Melting point | 153–154° C. |
| D - 29 | 3.49(3H, s), 4.71(2H, s), 6.22(1H, s), 7.17(1H, d, J=8Hz), 7.22(1H, br s), 8.00(1H, d, J=7Hz) [CDCL$_3$] | Melting point | 158–161° C. |
| D - 30 | 3.36(3H, s), 3.51(3H, s), 3.55–3.69(2H, m), 4.20–4.40(2H, m), 6.23(1H, s), 7.10(1H, br s), 7.16(1H, d, J=9Hz), 8.07(1H, d, J=7Hz) [CDCL$_3$] | Melting point | 119–120° C. |
| D - 31 | 2.97(3H, s), 5.11(2H, s), 6.23(1H, s), 7.19(1H, d, J=9Hz), 7.21(1H, br s), 7.26(5H, s), 8.11(1H, d, J=7Hz) [CDCL$_3$] | | Glass-like oily product |
| D - 32 | 3.48(3H, s), 6.21(1H, s), 7.05–7.60(7H, m), 8.20(1H, d, J=7Hz) [CDCL$_3$] | Melting point | 158–160° C. |
| D - 33 | 3.22(3H, s), 3.48(3H, s), 6.23(1H, s), 7.20(1H, d, J=9Hz), 8.11(1H, d, J=7Hz), 8.28(1H, br s) [d$_6$-DMSO] | Melting point | 214–216° C. |
| D - 34 | 2.69(3H, br d, J=3Hz), 3.54(3H, s), 5.62(1H, br s), 6.36(1H, s), 7.15(1H, br s), 7.16(1H, d, J=9Hz), 8.26(1H, d, J=8Hz) [CDCL$_3$] | Melting point | 216–218° C. |
| D - 35 | 1.43(3H, t, J=6Hz), 3.52(3H, s), 4.38(2H, q, J=6Hz), 6.23(1H, s), 7.23(1H, d, J=9Hz), 8.34(1H, d, J=7Hz), 9.29(1H, br s) [CDCL$_3$] | Melting point | 127–129° C. |
| D - 36 | 0.98–1.47(3H, m), 2.42(5H, br s), 3.54(3H, s), | | Glass-like oily product |

TABLE 2-continued

| Compound No. | ¹H-NMR δ [solvent] | Physical property | |
|---|---|---|---|
| | 6.37(1H, s), 7.38(1H, d, J=9Hz), 7.97(1H, s), 8.45(1H, d, J=7Hz), 9.57(1H, br s) [CDCL₃] | | |
| D - 37 | 2.46–3.81(5H, m), 3.46(3H, s), 6.21(1H, s), 7.10(1H, d, J=9Hz), 7.93(1H, d, J=10Hz), 8.14(1H, br s) [CDCL₃] | Melting point | 115–119° C. |
| D - 38 | 2.47–2.94(5H, m), 3.47(3H, br s), 3.61(3H, s), 6.21(1H, s), 7.10(1H, d, J=9Hz), 7.91(1H, br s), 8.14(1H, d, J=7Hz) [CDCL₃] | Melting point | 158–160° C. |
| D - 39 | 0.79–1.41(3H, m), 2.00–3.23(5H, m), 3.52(3H, s), 6.39(1H, s), 7.16(1H, d, J=7Hz), 7.46(1H, d, J=9Hz), [CDCL₃] | Melting point | 161–165° C. |
| D - 40 | 2.69–3.35(5H, m), 3.46(3H, s), 6.78(1H, s), 7.21(1H, d, J=7Hz), 7.43(1H, d, J =9Hz) [d₆-DMSO] | Melting point | 253–254° C. |
| D - 41 | 2.88(4H, s), 3.42(3H, s), 6.39(1H, s), 7.50(1H, d, J=7Hz), 7.64(1H, d, J=9Hz) [d₆-DMSO] | Melting point | 158–161° C. |
| D - 42 | 3.50(3H, s), 6.31(1H, s), 6.86(1H, br s), 7.22(1H, d, J=9Hz), 7.53(1H, d, J=7Hz) [CDCL₃] | | Oily product |
| D - 43 | 3.53(3H, s), 6.32(1H, s), 6.64(1H, br s), 7.28(1H, s), 7.44(1H, d, J=3Hz) [CDCL₃] | Melting point | 165–167° C. |
| D - 44 | 2.95(6H, s), 3.46(3H, s), 6.20(1H, s), 6.63(1H, d, J=7Hz), 7.13(1H, d, J=9Hz), 7.31(1H, s) [CDCL₃] | | Viscous oily product |
| D - 45 | 3.50(3H, s), 6.25(1H, s), 6.95–7.65(4H, m), 8.10(1H, br s), 8.42(1H, d, J=7Hz) [CDCL₃] | Melting point | 148–150° C. |
| D - 46 | 3.49(3H, s), 6.21(1H, s), 6.65–6.79(9H, m) [CDCL₃] | Melting | 220–222° C. (decomposition) |
| D - 47 | 1.29(3H, t, J=7Hz), 2.42–3.81(5H, m), 3.60(3H, br s), 4.19(2H, q, J=7Hz), 6.41(1H, s), 7.25(1H, d, J=10Hz), 8.20(1H, br s) [CDCL₃] | Melting point | 73–75° C. |
| D - 48 | 3.54(3H, s), 6.35(1H, s), 6.80–7.88(8H, m), 8.99(1H, br s) [d₆-DMSO] | Melting point | 217–219° C. |
| D - 49 | 1.48(3H, d, J=7Hz), 3.58(3H, s), 4.51(2H, q, J=7Hz), 6.35(1H, s), 7.20(1H, d, J=9Hz), 7.47–8.01(5H, s), 8.62(1H, br s) [CDCL₃] | Melting point | 175–177° C. |
| D - 50 | 2.34(3H, s) 3.49(3H, s), 6.21(1H, s), 7.16(1H, d, J=8Hz), 7.41(1H, br s), 8.11(1H, d, J=7Hz) [CDCL₃] | Melting point | 149–151° C. |
| D - 51 | 3.50(3H, s), 5.15(2H, s), 6.33(1H, s) 6.80–7.51(6H, m), 8.23(1H, d, J=7Hz) [CDCL₃] | Melting point | 142–144° C. |
| D - 52 | 3.50(3H, s), 5.10(2H, s), 6.25(1H, s), 7.11–7.35(6H, m), 8.11(1H, d, J=7Hz) [CDCL₃] | Melting point | 134–136° C. |
| D - 53 | 2.31(3H, s), 3.48(3H, s), 5.54(2H, s), 6.20(1H, s), 6.95–7.25(6H, m), 8.08(1H, d, J=7Hz) [CDCL₃] | Melting point | 142–143° C. |
| D - 54 | 1.00(9H, s), 3.56(3H, s), 3.86(2H, s), 6.37(1H, s), 7.09(1H, br s), 7.20(1H, d, J=9Hz), 8.22(1H, d, J=7Hz) [CDCL₃] | Melting point | 150–152° C. |

TABLE 2-continued

| Compound No. | $^1$H-NMR δ [solvent] | Physical property | |
|---|---|---|---|
| D - 55 | 3.54(3H, s), 4.19(2H, s), 6.34(1H, s), 7.10–7.41(6H, m), 8.07(1H, d, J=7Hz), 8.61(1H, br s) [CDCL$_3$] | Melting point | 192–193° C. |
| D - 56 | 3.59(3H, s), 6.36(1H, s), 7.35–7.90(8H, m) [d$_6$-DMSO] | Melting point | 189–191° C. |
| D - 57 | 3.48(3H, s), 6.50(1H, s), 7.38–7.90(8H, m) [d$_6$-DMSO] | Melting point | 211–223° C. |
| D - 58 | 3.56(3H, s), 3.80(3H, s), 6.36(1H, s), 6.75–7.66(3H, m), 8.20(1H, br s) [CDCL$_3$] | Melting point | 130–132° C. |
| D - 59 | 3.48(3H, s), 3.74(3H, s), 6.44(1H, s), 7.11–7.96(3H, m), 8.19(1H, br s) [d$_6$-DMSO] | Melting point | 254–256° C. |
| D - 60 | 3.53(3H, s), 3.79(3H, s), 6.33(1H, s), 7.38–7.68(2H, m), 8.19(1H, br s) [d$_6$-DMSO] | Melting point | 183–185° C. |
| D - 61 | 1.30(3H, t, J=7Hz), 3.51(3H, br s), 4.21(2H, q, J=7Hz), 6.32(1H, s), 7.09(1H, br s), 7.44(1H, d, J=8Hz), 8.20(1H, d, J=7Hz) [CDCL$_3$] | Melting point | 147–149° C. |
| D - 62 | 3.49(3H, s), 6.32(1H, s), 7.19–8.00(7H, m) [CDCl$_3$-DMSO-d$_6$] | Melting point | 205–207° C. |
| D - 63 | 3.51(3H, s), 3.79(3H, s), 5.10(2H, s), 6.31(1H, s), 6.78–7.45(6H, m), 8.22(1H, d, J=7Hz) [CDCL$_3$] | Melting point | 147–148° C. |
| D - 64 | 2.38(3H, s), 3.57(3H, s), 5.19(2H, s), 6.33(1H, s), 7.11–7.40((6H, m), 8.26(1H, d, J=8Hz) [CDCL$_3$] | Melting point | 152–154° C. |
| D - 65 | | Melting point | 119–121° C. |
| D - 66 | 3.52(3H, s), 3.73(3H, s), 6.27(1H, s), 7.05(1H, br s), 7.36(1H, d, J=8Hz), 8.08(1H, d, J=7Hz) [CDCL$_3$] | Melting point | 114–116° C. |
| D - 67 | 0.95(3H, t, J=7Hz), 1.28–1.98(2H, m), 3.50(3H, br s), 4.10(2H, t, J=7Hz) 6.31(1H, 2), 7.11(1H, br s), 7.43(1H, d, J=8Hz), 8.19(1H, d, J=7Hz) [CDCL$_3$] | Melting point | 154–157° C. |
| D - 68 | 3.53(3H, s), 3.79(3H, s), 6.36(1H, s), 6.75–8.20(4H, m), [CDCL$_3$] | Melting point | 125–126° C. |
| D - 69 | 3.54(3H, s), 5.11(2H, s), 6.31(1H, s), 7.11–7.60(7H, m), 8.20(1H, d, J=7Hz) [CDCL$_3$] | Melting point | 110–112° C. |
| 8 D - 70 | 1.23(3H, t, J=7Hz), 2.63(2H, q, J=7Hz), 3.54(3H, s), 5.17(2H, s), 6.36(1H, s), 7.20–7.38(6H, m), 8.29(1H, d, J=7Hz), [CDCL$_3$] | Melting point | 131–133° C. |
| D - 71 | 1.32(9H, s), 3.53(3H, s), 5.16(2H, s), 6.35(1H, s), 7.17–7.46(6H, m), 8.27(1H, d, J=7Hz) [CDCL$_3$] | Semi-solid | |
| D - 72 | 3.52(3H, s), 5.23(2H, s), 6.34(1H, s), 7.30–7.70(6H, m), 8.22(1H, d, J=7Hz) [CDCL$_3$] | Melting point | 103–104° C. |
| D - 73 | 3.54(3H, s), 5.27(2H, s), 6.36(1H, s), 7.20–7.70(4H, m), 8.10–8.40(3H, m) [CDCL$_3$] | Glass-like | |
| D - 74 | 3.56(3H, s), 5.32(2H, s), 6.35(1H, s), | Glass-like | |

TABLE 2-continued

| Compound No. | $^1$H-NMR δ [solvent] | Physical property | |
|---|---|---|---|
| | 7.20–7.75(5H, m), 8.27(1H, d, J=7Hz), 8.69(1H, d, J=5Hz) [CDCL$_3$] | | |
| D-75 | 3.52(3H, s), 5.34(2H, s), 6.34(1H, s), 6.88–7.45(5H, m); 8.26(1H, d, J=7Hz), [CDCL$_3$] | Melting point | 167–169° C. |
| D-76 | 1.61(3H, d, J=6Hz), 3.56(3H, s), 5.89(1H, q, J=6Hz), 6.38(1H, s), 7.14–7.55(7H, m), 8.29(1H, d, J=7Hz) [CDCL$_3$] | Melting point | 163–164° C. |
| D-77 | 2.99(2H, t, J=7Hz), 3.54(3H, s), 4.39(2H, t, J=7Hz), 6.35(1H, s), 7.05–7.40(7H, m), 8.20(1H, d, J=8Hz) [CDCL$_3$] | Melting point | 87–88° C. |
| D-78 | 3.56(3H, s), 4.60(2H, q, J=8Hz), 6.38(1H, s), 7.36(1H, d, J=9Hz), 7.38(1H, br s), 8.19(1H, d, J=7Hz) [CDCL$_3$] | Melting point | 164–165° C. |
| D-79 | 1.76–2.26(9H, m), 3.55(3H, s), 4.15(2H, d, J=6Hz), 6.35(1H, s), 7.15(1H, br s), 7.39(1H, d, J=9Hz), 8.26(1H, d, J=7Hz) [CDCL$_3$] | Melting point | 116–118° C. |
| D-80 | 1.74(3H, d, J=5Hz), 3.55(3H, s), 4.61(2H, m), 5.59–5.88(2H, m), 6.39(1H, s), 7.18(1H, br s), 7.34(1H, d, J=9Hz), 8.23(1H, d, J=7Hz), [CDCL$_3$] | Glass-like | |
| D-81 | 3.52(3H, s), 4.34(2H, d, J=5Hz), 5.72(1H, br s), 6.30(1H, s), 6.99(1H, br s), 7.08(1H, d, J=9Hz), 7.20(5H, s), 8.33(1H, d, J=7Hz) [CDCL$_3$] | Melting point | 165–167° C. |
| D-82 | 3.60(3H, s), 4.69(2H, d, J=5Hz), 5.18–6.13(3H, m), 6.41(1H, s), 7.23(1H, br s), 7.36(1H, d, J=9Hz), 8.28(1H, d, J=7Hz) [CDCL$_3$] | Melting point | 148–149° C. |
| D-83 | 3.57(3H, s), 4.87(2H, d, J=6Hz), 6.32–6.72(3H, m), 7.19–7.49(7H, m), 8.27(1H, d, J=7Hz) [CDCL$_3$] | Melting point | 114–116° C. |
| D-84 | 3.56(3H, s), 5.25(2H, s), 6.39(1H, s), 7.15–8.71(7H, m) [CDCL$_3$] | Melting point | 170–171° C. |
| D-85 | 3.59(3H, s), 5.22(2H, s), 6.38(1H, s), 7.12–7.51(4H, m), 8.21(1H, d, J=7Hz), 8.12(2H, d, J=6Hz) [CDCL$_3$] | Melting point | 208–209° C. |
| D-86 | 3.55(3H, s), 5.21(2H, s), 6.40(1H, s), 7.08–7.49(5H, m), 8.30(1H, br s) [CDCL$_3$] | Melting point | 155–156° C. |
| D-87 | 3.49(3H, s), 5.36(2H, s), 6.32(1H, s), 7.21–8.03(9H, m), 8.31(1H, d, J=7Hz) [CDCL$_3$] | Melting point | 130–132° C. |
| D-88 | 2.34(3H, s), 3.50(3H, s), 6.29(1H, s), 6.92–7.55(6H, m), 8.24(1H, d, J=7Hz) [CDCL$_3$] | Melting point | 145–147° C. |
| D-89 | 3.06(3H, s), 3.53(3H, s), 4.59(2H, s), 6.34(1H, s), 6.90–7.40(7H, m), 8.43(1H, d, J=8Hz) [CDCL$_3$] | Melting point | 143–145° C. |
| D-90 | 1.45–1.80(6H, m), 3.28–3.64(7H, m), 6.28(1H, s), 7.00(1H, br s), 7.29(1H, d, J=9Hz), 8.39(1H, d, J=7Hz) [CDCL$_3$] | Melting point | 99–100° C. |
| D-91 | 3.50(3H, s), 4.00(3H, s), 6.35(1H, s), 7.21(1H, d, J=8Hz), 7.85(1H, d, J=7Hz), | Melting point | 123–125° C. |

TABLE 2-continued

| Compound No. | ¹H-NMR δ [solvent] | Physical property | |
|---|---|---|---|
| | 8.19(1H, br s) [CDCL₃] | | |
| D - 92 | 3.57(3H, s), 4.39(2H, s), 6.39(1H, s), 6.78(1H, br s), 7.28(1H, d, J=9Hz), 7.30(5H, s), 7.68(1H, d, J=7Hz) [CDCL₃] | Melting point | 160–162° C. |
| D - 93 | 2.59(3H, s), 3.50(3H, s), 6.22(1H, s), 7.20(1H, d, J=8Hz), 7.91(1H, d, J=7Hz), 8.07(1H, br s) [CDCL₃] | Melting point | 123–125° C. |
| D - 94 | 3.53(3H, s), 5.54(2H, s), 6.34(1H, s), 7.32(1H, d, J=9Hz), 7.36(5H, s), 7.98(1H, d, J=9Hz), 8.38(1H, br s) [CDCL₃] | Melting point | 71–73° C. |
| D - 95 | 3.55(3H, s), 3.72(3H, s), 4.43(2H, s), 6.35(1H, s), 7.47(1H, d, J=9Hz), 7.71(1H, d, J=9Hz), 8.29(1H, s) [CDCL₃] | Melting point | 152–154° C. |
| D - 96 | 3.46(3H, s), 3.62(2H, d, J=5Hz), 3.74(3H, s), 4.91(1H, t, J=5Hz), 6.26(1H, s), 6.35(1H, d, J=7Hz), 7.22(1h, d, J=9Hz) [CDCL₃] | Glass-like | |
| D - 97 | 1.47(3H, d, J=7Hz), 3.72(3H, s), 3.79(3H, s), 4.06(1H, dq, J=7, 7Hz), 4.73(1H, br s), 6.34(1H, s), 6.45(1H, d, J=7Hz), 7.26(1H, d, J=9Hz) [CDCL₃] | Viscous oily product | |
| D - 98 | 1.25(3H, t, J=7Hz), 1.45(3H, d, J=7Hz), 3.48(3H, s), 4.15(1H, dq, J=7, 7Hz), 4.17(2H, q, J=7Hz), 4.82(1H, br s), 6.31(1H, s), 6.45(1H, d, J=7Hz), 7.23(1H, d, J=9Hz) [CDCL₃] | Viscous oily product | |
| D - 99 | | | |
| D-100 | | | |
| D-101 | | | |
| D-102 | | | |
| D-103 | | | |
| D-104 | | | |

The compounds of the present invention synthesized in accordance with the above scheme or Examples including the compounds synthesized in the above Examples are shown below, but the present invention is not limited by these.

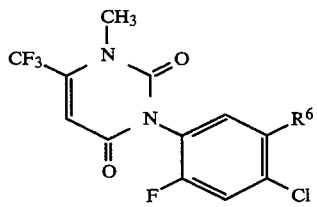

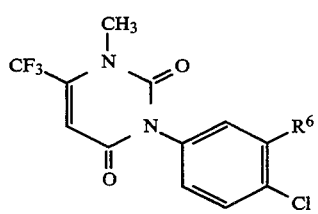

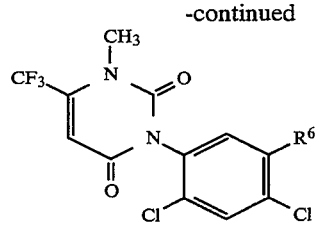

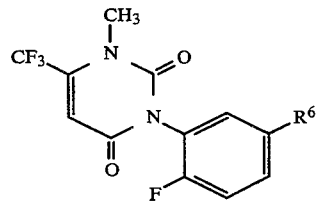

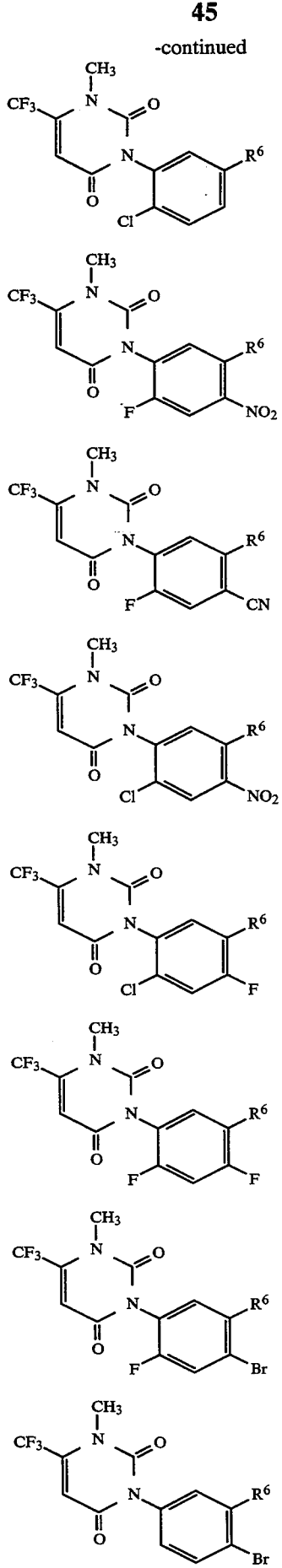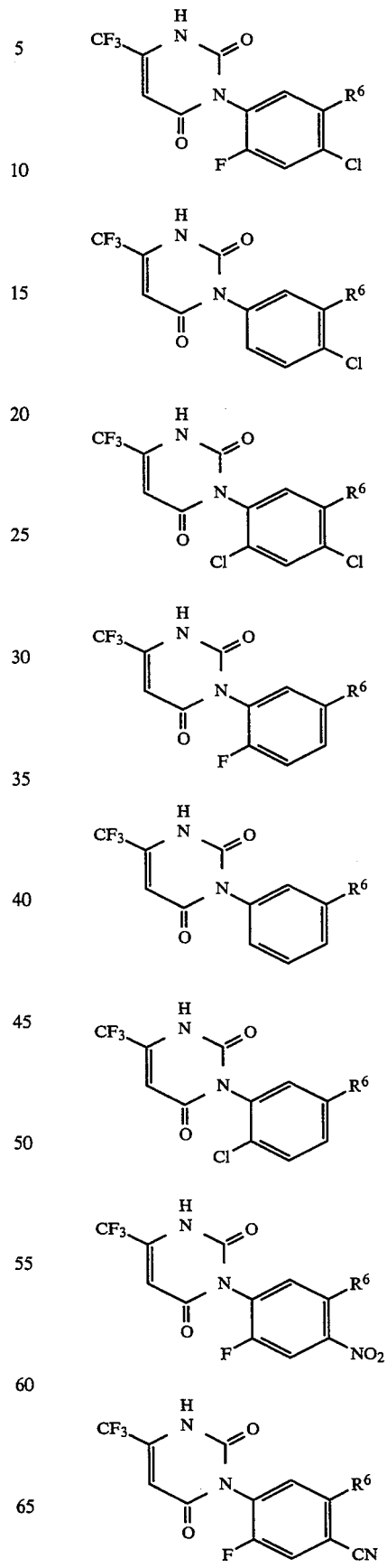

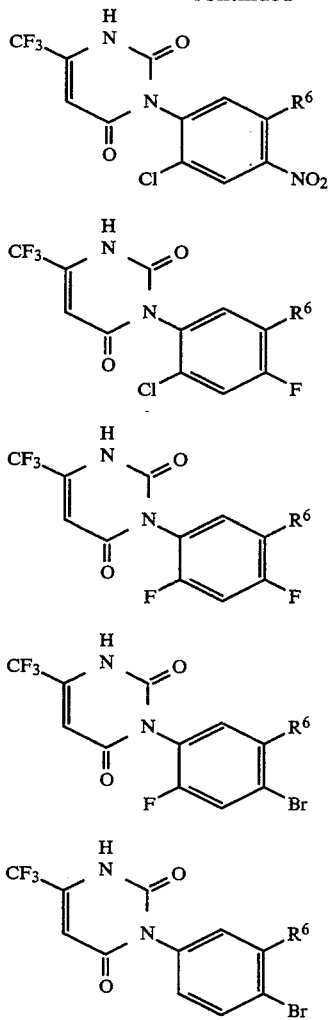

NHSO₂CH₂-(2-I-Ph), NHSO₂CH₂-(3-I-ph),
NHSO₂CH₂-(4-I-Ph), NHSO₂CH₂-(2-Me-Ph),
NHSO₂CH₂-(3-Me-Ph), NHSO₂CH₂-(4-Me-Ph),
NHSO₂CH₂-(2-MeO-Ph), NHSO₂CH₂-(3-MeO-Ph),
NHSO₂CH₂-(4-MeO-Ph), NHSO₂CH₂-(2-NO₂-Ph),
NHSO₂CH₂-(3-NO₂-Ph), NHSO₂CH₂-(4-NO₂-Ph),
NHSO₂CH₂-(2-MeOCO-Ph), NHSO₂CH₂-(3-MeOCO-Ph),
NHSO₂CH₂-(4-MeOCO-Ph), NHSO₂CH₂-(2-CF₃-Ph),
NHSO₂CH₂-(3-CF₃-Ph), NHSO₂CH₂-(4-CF₃-Ph),
NHSO₂CH₂-(2-CF₃O-Ph), NHSO₂CH₂-(3-CF₃O-Ph),
NHSO₂CH₂-(4-CH₃O-Ph), NHSO₂NHCO₂Me,
NHSO₂NHCO₂Et,
NHSO₂NHCO₂-n-Pr, NHSO₂NHCO₂-i-Pr, NHSO₂OMe,
NHSO₂OEt, NHSO₂O-i-Pr, NHSO₂O-n-Pr, NHSO₂OCH₂cl,
NHSO₂OSi(Me)₃, NHSO₂Ph, NHSO₂-(2-F-Ph),
NHSO₂-(3-F-Ph), NHSO₂-(4-F-Ph), NHSO₂-(2-Cl-Ph),
NHSO₂-(3-Cl-Ph), NHSO₂-(4-Cl-Ph), NHSO₂-(2-Br-Ph),
NHSO₂-(3-Br-Ph), NHSO₂-(4-Br-Ph), NHSO₂-(2-I-Ph),
NHSO₂-(3-I-Ph), NHSO₂-(4-I-Ph), NHSO₂-(2-Me-Ph),
NHSO₂-(3-Me-Ph), NHSO₂-(4-Me-Ph), NHSO₂-(2-MeO-Ph),
NHSO₂-(3-MeO-Ph), NHSO₂-(4-MeO-Ph), NHSO₂-(4-Et-Ph),
NHSO₂-(4-n-Pr-Ph), NHSO₂-(4-i-Pr-Ph),
NHSO₂-(4-n-Bu-Ph), NHSO₂-(4-s-Bu-Ph),
NHSO₂-(4-i-Bu-Ph), NHSO₂-(4-t-Bu-Ph),
NHSO₂-(4-t-Am-Ph), NHSO₂-(4-n-Hex-Ph),
NHSO₂-(2-NO₂-Ph), NHSO₂-(3-NO₂-Ph),
NHSO₂-(4-NO₂-Ph), NHSO₂-(2-MeOCO-Ph),
NHSO₂-(3-MeOCO-Ph), NHSO₂-(4-MeOCO-Ph),
NHSO₂-(2-CF₃-Ph), NHSO₂-(3-CF₃-Ph),
NHSO₂-(4-CF₃-Ph), NHSO₂-(2-CF₃O-Ph),
NHSO₂-(3-CF₃O-Ph), NHSO₂-(4-CH₃O-Ph),
NHSO₂-(4-CF₃CF₂O-Ph), NHSO₂-(3-MeCO-Ph),
NHSO₂-(3-HOCO-Ph), NHSO₂-(4-HOCO-Ph),
NHSO₂-(2,4-di-NO₂-Ph), NHSO₂-(4-Cl-3-NO₂-Ph),
NHSO₂-(2-Me-5-NO₂-Ph), NHSO₂-(4-Cl-3-HOCO-Ph),
NHSO₂-(2-MeCONH-Ph), NHSO₂-(3-MeCONH-Ph),
NHSO₂-(4-MeCONH-Ph), NHSO₂-(2-NO₂-4-CF₃-Ph),
NHSO₂-(3,5-di-CF₃-Ph),
NHSO₂-(4-(2,2-dichlorocyclopropyl)-Ph),
NHSO₂-(3-NO₂-4-t-Bu-Ph), NHSO₂-(4-(1-bromoethyl)-Ph),
NHSO₂-(2,5-di-MeO-Ph),
NHSO₂-(4-dimethylamino-3-NO₂-Ph),
NHSO₂-(4-Cl-3-CF₃-Ph), NHSO₂-(2,4-di-Me-3-NO₂-Ph),
NHSO₂-(2,4-di-Cl-5-Me-Ph),
NHSO₂-(4-Cl-2,5-di-Me-Ph), NHSO₂-(2-Cl-6-Me-Ph),
NHSO₂-(3-Cl-4-MeO-Ph), NHSO₂-(3-Cl-2-Me-Ph),
NHSO₂-(2-Cl-5-CF₃-Ph), NHSO₂-(2-Cl-4-CF₃-Ph),
NHSO₂-(2-CN-Ph), NHSO₂-(3-CN-Ph), NHSO₂-(4-CN-Ph),
NHSO₂-(5-F-2-Me-Ph), NHSO₂-(5-Cl-2-MeO-Ph),
NHSO₂-(2,4-di-i-Pr-Ph), NHSO₂-(6-MeO-3-Me-Ph),
NHSO₂-(2,4-di-MeO-Ph), NHSO₂-(3,4-di-MeO-Ph),
NHSO₂-(3,5-di-MeO-Ph), NHSO₂-(2,5-di-MeO-Ph),
NHSO₂-(2,6-di-MeO-Ph), NHSO₂-(2,3-di-MeO-Ph),
NHSO₂-(2,4-di-Cl-Ph), NHSO₂-(3,4-di-Cl-Ph),
NHSO₂-(3,5-di-Cl-Ph), NHSO₂-(2,5-di-Cl-Ph),
NHSO₂-(2,6-di-Cl-Ph), NHSO₂-(2,3-di-Cl-Ph), in which R₆ represent the following:

(Abbreviations indicate respectively the meanings as shown below. Me: methyl group, Et: ethyl group, Ph: phenyl group, n-Bu: normal butyl group, s-Bu: secondary butyl group, i-Bu: iso butyl group, t-Bu: tertiary butyl group, n-Pr: normal propyl group, i-Pr: iso propyl group, n-Am: normal amyl group, t-Am: tertialy amyl group, n-Hex: normal hexyl group, c-Pr: cyclopropyl group, c-Bu: cyclobutyl group, c-pen: cyclopentyl group, c-Hex: cyclohexyl group)
NHSO₂-t-Am, NHSO₂-n-Am, NHSO₂-n-Hex,
NHSO₂CH₂(CH₂)₆Me, NHSO₂CH₂(CH₂)₈Me,
NHSO₂CH₂(CH₂)₁₀Me, NHSO₂CH₂(CH₂)₁₂Me,
NHSO₂CH₂(CH₂)₁₄Me, NHSO₂CH₂(CH₂)₁₆Me,
NHSO₂CH=CH₂, NHSO₂CH₂CH=CH₂,
NHSO₂CH(Me)CH=CH₂,
NHSO₂C(Me)₂CH=CH₂, NHSO₂CH₂C≡CH,
NHSO₂CH(Me)C≡CH, NHSO₂C(Me)₂C≡CH,
NHSO₂CH=CHPh, NHSO₂(CF₂)₃CF₃,
NHSO₂(CF₂)₅CF₃, NHSO₂(CF₂)₇CF₃,
NHSO₂CH₂Si(Me)₃, NHSO₂CH₂SO₂Me,
NHSO₂CH₂Ph,
NHSO₂CH₂CH₂Ph, NHSO₂CH₂-(2-F-Ph),
NHSO₂CH₂-(3-F-Ph), NHSO₂CH₂-(4-F-Ph),
NHSO₂CH₂-(2-Cl-Ph), NHSO₂CH₂-(3-Cl-Ph),
NHSO₂CH₂-(4-Cl-Ph), NHSO₂CH₂-(2-Br-Ph),
NHSO₂CH₂-(3-Br-Ph), NHSO₂CH₂-(4-Br-Ph), NHSO₂-(2,4,6-tri-Cl-Ph), NHSO₂-(2,4-di-F-Ph),
NHSO₂-(3,4-di-F-Ph), NHSO₂-(3,5-di-F-Ph),
NHSO₂-(2,5-di-F-Ph), NHSO₂-(2,6-di-F-Ph),
NHSO₂-(2,5-di-Br-Ph), NHSO₂-(3,4-di-Br-Ph),
NHSO₂-(2-Cl-4-F-Ph), NHSO₂-(3-Cl-4-F-Ph),
NHSO₂-(pentafluoro-Ph), NHSO₂-(pentamethyl-Ph),
NHSO₂-(2,4,6,-tri-Me-Ph), NHSO₂-(2,4,6,-tri-i-Pr-Ph),
NHSO₂-(2,3,5,6-tetra-Me-Ph), NHSO₂-(2,4-di-Me-Ph),
NHSO₂-(3,4-di-Me-Ph), NHSO₂-(3,5-di-Me-Ph),
NHSO₂-(2,5-di-Me-Ph), NHSO₂-(2,6-di-Me-Ph),
NHSO₂-(2,3-di-Me-Ph), NHSO₂-Q1, NHSO₂-Q2,
NHSO₂-Q3, NHSO₂-Q4, NHSO₂-Q5, NHSO₂-Q6,
NHSO₂-Q7, NHSO₂-Q8, NHSO₂-Q9, NHSO₂-Q10,
NHSO₂-Q11, NHSO₂-Q12, NHSO₂-Q13, NHSO₂-(3-CF₃-Q1),
NHSO₂-(3-CON(Me)₂-Q1), NHSO₂-(2Cl-Q2),
NHSO₂-(2-Cl-Q3), NHSO₂-(4,5-di-Br-Q4),
NHSO₂-(2,5-di-Cl-Q4), NHSO₂-(4,5-di-Cl-Q4),
NHSO₂-(5-Cl-Q4), NHSO₂-(5-Br-4-Cl-Q4),
NHSO₂-(4-Br-5-Cl-Q4), NHSO₂-(3-Br-5-Cl-Q4),
NHSO₂-(7-Cl-Q5), NHSO₂-(7-Me-Q5),
NHSO₂-(3,5-di-Me-Q8), NHSO₂-(3-Me-5-Cl-Q8),
NHSO₂-(3-Me-5-MeOCO-Q8), NHSO₂-(4-MeOCO-Q9),
NHSO₂-(4-MeOCO-Q10), NHSO₂-(2,4-di-Me-Q11),
NHSO₂-(3,5-di-Me-Q12), NHCOMe, N(COMe)Me,
N(COMe)Et,
N(COMe)-n-Pr, N(COMe)-i-Pr, N(COMe)CH₂C≡CH,
N(COMe) CH₂CH=CH₂, N(COMe)CH₂Ph,
NHCOEt, NHCO-n-Pr,
NHCO-i-Pr, NHCO-n-Bu, NHCO-s-Bu, NHCO-i-Bu,
NHCO-t-Bu, NHCOC(Me)=CH₂, NHCOCH₂CH=CH₂,
NHCOCH(Me)CH=CH₂, NHCOC(Me)₂CH=CH₂,
NHCOCH₂C≡CH, NHCOCH(Me)C≡CH,
NHCOC(Me)₂C≡CH,
NHCO-(cyclopropyl), NHCOCH(Me)-n-Bu,
NHCOPh, NHCOCH₂Ph,
NHCOCH₂Cl, NHCOCH₂Br, NHCOCHCl₂,
NHCOCCl₃,
NHCOCF₃, NHCOCH₂COMe, NHCOCH₂CH₂CO₂H,
NHCOCH₂CH₂CH₂CO₂Me, NHCOCH₂CH(Me)CH₂CO₂H,
NHCOCH₂CH(Me)CH₂CO₂Me,
NHCOCH₂CH(CF₃)CH₂CO₂H,
NHCOCH₂CH(CF₃)CH₂CO₂Me, N(SO₂Me)COC(Me)=CH₂,
N(SO₂Me)COCH₂CH=CH₂, N(SO₂Me)COCH(Me)CH=CH₂,
N(SO₂Me)COCH₂CH=CH₂, N(SO₂Me)COCH(Me)CH=CH₂,
N(SO₂Me)COC(Me)₂CH=CH₂, N(SO₂Me)COCH₂C≡CH,
N(SO₂Me)COCH(Me)C≡CH, N(SO₂Me)COC(Me)₂C≡CH,
N(SO₂Me)CO-(cyclopropyl), N(SO₂Me)COCH(Me)-n-Bu,
N(SO₂Me)COPh, N(SO₂Me)COCH₂Ph, N(SO₂Me)COCH₂Cl,
N(SO₂Me)COCH₂Br, N(SO₂Me)COCHCl₂,
N(SO₂Me)COCCl₃, N(SO₂Me)COCF₃,
N(SO₂Me)COCH₂COMe, N(SO₂Me)COCH₂CH₂CO₂H,
N(SO₂Me)COCH₂CH₂CH₂CO₂Me,
N(SO₂Me)COCH₂CH(Me)CH₂CO₂H,
N(SO₂Me)COCH₂CH(Me)CH₂CO₂Me,
N(SO₂Me)COCH₂CH(CF₃)CH₂CO₂H,
N(SO₂Me)COCH₂CH(CF₃)CH₂CO₂Me,
N(SO₂Et)COC(Me)=CH₂, N(SO₂Et)COCH₂CH=CH₂,
N(SO₂Et)COCH(Me)CH=CH₂, N(SO₂Et)COC(Me)₂CH=CH₂,
N(SO₂Et)COCH₂C≡CH, N(SO₂Et)COCH(Me)C≡CH,
N(SO₂Et)COC(Me)₂C≡CH, N(SO₂Et)CO-(cyclopropyl),
N(SO₂Et)COCH(Me)CH₂CH₂CH₂Me, N(SO₂Et)COPh,
N(SO₂Et)COCH₂Ph, N(SO₂Et)COCH₂Cl,
N(SO₂Et)COCH₂Br, N(SO₂Et)COCHCl₂,
N(SO₂Et)COCCl₃, N(SO₂Et)COCF₃,
N(SO₂Et)COCH₂COMe, N(SO₂Et)COCH₂CH₂CH₂CO₂H,
N(SO₂Et)COCH₂CH₂CH₂CO₂Me,
N(SO₂Et)COCH₂CH(Me)CH₂CO₂H,
N(SO₂Et)COCH₂CH(Me)CH₂CO₂Me,
N(SO₂Et)COCH₂CH(CF₃)CH₂CO₂H,
N(SO₂Et)COCH₂CH(CF₃)CH₂CO₂Me, NHCOH,
N(COH)Me,
N(COH)Et, N(COH)-n-Pr, N(COH)-i-Pr, N(COH)-n-Bu,
N(COH)-s-Bu, N(COH)-i-Bu, N(COH)-t-Bu,
N(COH)C(Me)=CH₂, N(COH)CH₂CH=CH₂,
N(COH)CH(Me)CH=CH₂, N(COH)C(Me)₂CH=CH₂,
N(COH)CH₂C≡CH, N(COH)CH(Me)C≡CH,
N(COH)C(Me)₂C≡CH, N(COH)-(cyclopropyl),
N(COH)CH(Me)-n-Bu, N(COH)Ph, N(COH)CH₂Ph,
N(COH)CH₂Cl, N(COH)CH₂Br, N(COH)CHCl₂,
N(COH)CCl₃, N(COH)CF₃, N(COH)CH₂COMe,
N(COH)CH₂CH₂CH₂CO₂H, N(COH)CH₂CH₂CH₂CO₂Me,
N(COH)CH₂CH(Me)CH₂CO₂H, N(COH)CH₂CH(Me)CH₂CO₂Me,
N(COH)CH₂CH(CF₃)CH₂CO₂H,
N(COH)CH₂CH(CF₃)CH₂CO₂H,
N(COH)SO₂Me, N(COH)SO₂Et, N(COH)SO₂-n-Pr,
N(COH)SO₂-i-Pr, N(COH)SO₂-n-Bu, N(COH)SO₂-s-Bu,
N(COH)SO₂-i-Bu, H(COH)SO₂-t-Bu, N(SO₂CF₃)₂,
NHCO₂Me, NHCO₂Et, NHCO₂-n-Pr, NHCO₂-i-Pr,
NHCO₂-n-Bu, NHCO₂-s-Bu, NHCO₂-i-Bu, NHCO₂-t-Bu,
N(Me)CO₂Me, N(Me)CO₂Et, N(Me)CO₂-n-Pr,
N(Me)CO₂-i-Pr, N(Me)CO₂-n-Bu, N(Me)CO₂-s-Bu,
N(Me)CO₂-i-Bu, N(Me)CO₂-t-Bu, N(Et)CO₂Me,
N(Et)CO₂Et, N(Et)CO₂-n-Pr, N(Et)CO₂-i-Pr,
N(Et)CO₂-n-Bu, N(Et)CO₂-s-Bu, N(Et)CO₂-i-Bu,
N(Et)CO₂-t-Bu, N(SO₂Me)CO₂Me, N(SO₂Me)CO₂Et,
N(SO₂Me)CO₂-n-Pr, N(SO₂Me)CO₂-i-Pr,
N(SO₂Me)CO₂-n-Bu, N(SO₂Me)CO₂-s-Bu,
N(SO₂Me)CO₂-i-Bu, N(SO₂Me)CO₂-t-Bu,
N(SO₂Et)CO₂Me, N(SO₂Et)CO₂Et, N(SO₂Et)CO₂-n-Pr,
N(SO₂Et)CO₂-i-Pr, N(SO₂Et)CO₂-n-Bu,
N(SO₂Et)CO₂-s-Bu, H(SO₂Et)CO₂-i-Bu,
N(SO₂Et)CO₂-t-Bu, NHCO₂CH₂-t-Bu, NHCO₂-n-Am,
NHCO₂-n-Hex, NHCO₂CH₂(CH₂)₆Me,
NHCO₂(CH₂)₈Me, NHCO₂CH₂(CH₂)₁₄Me,
NHCO₂CH₂(CH₂)₁₆Me, NHCO₂CH=CH₂,
NHCO₂CH₂CH=CH₂, NHCO₂CH(Me)CH=CH₂,
NHCO₂C(Me)₂CH=CH₂, NHCO₂CH₂C≡CH, $NHCO_2CH(Me)C\equiv CH$, $NHCO_2C(Me)_2C\equiv CH$, $NHCO_2CH_2Ph$,
$N(Me)CO_2CH=CH_2$, $N(Me)CO_2CH_2CH=CH_2$,
$N(Me)CO_2CH(Me)CH=CH_2$, $N(Me)CO_2C(Me)_2CH=CH_2$,
$N(Me)CO_2CH_2C\equiv CH$, $N(Me)CO_2CH(Me)C\equiv CH$,
$N(Me)CO_2C(Me)_2C\equiv CH$, $N(Me)CO_2CH_2Ph$,
$NHCO_2CH=CHPh$, $NHCO_2CF_3$, $NHCO_2CH_2CF_3$,
$NHCO_2CH(F)CF_3$, $NHCO_2(CF_2)_3CF_3$,
$NHCO_2(CF_2)_{5}$ $_ICF_3$, $NHCO_2(CF_2)_7CF_3$, $NHCO_2CCl_3$,
$NHCO_2CHCl_2$, $NHCO_2CH_2Cl$, $NHCO_2CH_2CCl_3$,
$NHCO_2CH_2CH_2Cl$, $NHCO_2CH_2CH_2CH_2Cl$,
$NHCO_2CH_2CH(Cl)Me$, $NHCO_2CH_2CH_2OMe$,
$NHCO_2CH_2CH_{OEt}$, $_{NHCO2}Ph$, $N(Me)CO_2Ph$,
$NHCO_2$-(2-F-Ph), $NHCO_2$-(3-F-Ph), $NHCO_2$-(4-F-Ph),
$NHCO_2$-(2-Cl-Ph), $NHCO_2$-(3-Cl-Ph),
$NHCO_2$-(4-Cl-Ph), $NHCO_2$-(2-Br-Ph), $NHCO_2$-(3-Br-Ph),
$NHCO_2$-(4-Br-Ph), $NHCO_2$-(2-I-Ph), $NHCO_2$-(3-I-Ph),
$NHCO_2$-(4-I-Ph), $NHCO_2$-(2-Me-Ph), $NHCO_2$-(3-Me-Ph),
$NHCO_2$-(4-Me-Ph), $NHCO_2$-(2-MeO-Ph), $NHCO_2$-(3-MeO-Ph),
$NHCO_2$-(4-MeO-Ph), $NHCO_2$-(4-Et-Ph), $NHCO_2$-(4-n-Pr-Ph),
$NHCO_2$-(4-i-Pr-Ph), $NHCO_2$-(4-n-Bu-Ph),
$NHCO_2$-(4-s-Bu-Ph), $NHCO_2$-(4-i-Bu-Ph),
$NHCO_2$-(4-t-Bu-Ph), $NHCO_2$-(4-t-Am-Ph),
$NHCO_2$-(4-n-Hex-Ph), $NHCO_2$-(2-NO_2-Ph),
$NHCO_2$-(3-NO_2-Ph), $NHCO_2$-(4-NO_2-Ph),
$NHCO_2$-(2-MeOCO-Ph), $NHCO_2$-(3-MeOCO-Ph),
$NHCO_2$-(4-MeOCO-Ph), $NHCO_2$-(2-CF_3-Ph),
$NHCO_2$-(3-CF_3-Ph), $NHCO_2$-(4-CF_3-Ph),
$NHCO_2$-(2-CF_3O-Ph), $NHCO_2$-(3-CF_3O-Ph),
$NHCO_2$-(4-CF_3-Ph), $NHCO_2$-(4-CF_3CF_2O-Ph),
$NHCO_2$-(3-MeCO-Ph), $NHCO_2$-(3-HOCO-Ph),
$NHCO_2$-(4-HOCO-Ph), $NHCO_2$-(2,4-di-NO_2-Ph),
$NHCO_2$-(4-Cl-3-NO_2-Ph), $NHCO_2$-(2-Me-5-NO_2-Ph),
$NHCO_2$-(4-Cl-3-HOCO-Ph), $NHCO_2$-(2-MeCONH-Ph),
$NHCO_2$-(3-MeCONH-Ph), $NHCO_2$-(4-MeCONH-Ph),
$NHCO_2$-(2-NO_2-4-CF_3-Ph), $NHCO_2$-(3,5-di-CF_3_I-Ph),
$NHCO_2$-(4-(2,2-dichlorocyclopropyl)-Ph),
$NHCO_2$-(3-NO_2-4-t-Bu-Ph), $NHCO_2$-(4-(1-bromoethyl)-Ph),
$NHCO_2$-(2,5-di-MeO-Ph),
$NHCO_2$-(4-dimethylamino-3-NO_2-Ph),
$NHCO_2$-(4-Cl-3-CF_3-Ph), $NHCO_2$-(2,4-di-Me-3-NO_2-Ph),
$NHCO_2$-(2,4-di-Cl-5-Me-Ph),
$NHCO_2$-(4-Cl-2,5-di-Me-Ph), $NHCO_2$-(2-Cl-6-Me-Ph),
$NHCO_2$-(3-Cl-4-MeO-Ph), $NHCO_2$-(3-Cl-2-Me-Ph),
$NHCO_2$-(2 l -Cl- b 5-CF_3-Ph), $NHCO_2$-(2-Cl-4-CF_3-Ph),
$NHCO_2$-(2-CN-Ph), $NHCO_2$-(3-CN-Ph),
$NHCO_2$-(4-CN-Ph), $NHCO_2$-(5-F-2-Me-Ph),
$NHCO_2$-(5-Cl-2-MeO-Ph), $NHCO_2$-(2,4-di-i-Pr-Ph),
$NHCO_2$-(6-MeO-3-Me-Ph), $NHCO_2$-(2,4-di-MeO-Ph),
$NHCO_2$-(3,4-di-MeO-Ph), $NHCO_2$-(3,5-di-MeO-Ph),
$NHCO_2$-(2,5-di-MeO-Ph), $NHCO_2$-(2,6-di-MeO-Ph),
$NHCO_2$-(2,3-di-MeO-Ph), $NHCO_2$-(2,4-di-Cl-Ph),
$NHCO_2$-(3,4-di-Cl-Ph), $NHCO_2$-(3,5-di-Cl-Ph),
$NHCO_2$-(2,5-di-Cl-Ph), $NHCO_2$-(2,6-di-Cl-Ph),
$NHCO_2$-(2,3-di-Cl-Ph), $NHCO_2$-(2,4,6,-tri-Cl-Ph),
$NHCO_2$-(2,4-di-F-Ph), $NHCO_2$-(3,4-di-F-Ph),
$NHCO_2$-(3,5-di-F-Ph), $NHCO_2$-(2,5-di-F-Ph),
$NHCO_2$-(2,6-di-F-Ph), $NHCO_2$-(2,5-di-Br-Ph),
$NHCO_2$-(3,4-di-Br-Ph), $NHCO_2$-(2-Cl-4-F-Ph),
$NHCO_2$-(3-Cl-4-F-Ph), $NHCO_2$-(pentafluoro-Ph),
$NHCO_2$-(pentamethyl-Ph), $NHCO_2$-(2,4,6,-tri-Me-Ph),
$NHCO_2$-(2,4,6-tri-i-Pr-Ph), $NHCO_2$-(2,3,5,6-tetra-Me-Ph),
$NHCO_2$-(2,4-di-Me-Ph), $NHCO_2$-(3,4-di-Me-Ph),
$NHCO_2$-(3,5-di-Me-Ph), $NHCO_2$-(2,5-di-Me-Ph),
$NHCO_2$-(2,6-di-Me-Ph), $NHCO_2$-(2,3-di-Me-Ph),
$NHCO_2CH_2$-(2-F-Ph), $NHCO_2CH_2$-(3-F-Ph),
$NHCO_2CH_2$-(4-F-Ph), $NHCO_2CH_2$-(2-Cl-Ph),
$NHCO_2CH_2$-(3-Cl-Ph), $NHCO_2CH_2$-(4-Cl-Ph),
$NHCO_2CH_2$-(2-Br-Ph), $NHCO_2CH_2$-(3-Br-Ph),
$NHCO_2CH_2$-(4-Br-Ph), $NHCO_2CH_2$-(2-I-Ph),
$NHCO_2CH_2$-(3-I-Ph), $NHCO_2CH_2$-(4I-Ph),
$NHCO_2CH_2$-(2-Me-Ph), $NHCO_2CH_2$-(3-Me-Ph),
$NHCO_2CH_2$-(4-Me-Ph), $NHCO_2CH_2$-(2-MeO-Ph),
$NHCO_2CH_2$-(3-MeO-Ph), $NHCO_2CH_2$-(4-MeO-Ph),
$NHCO_2CH_2$-(4-Et-Ph), $NHCO_2CH_2$-(4-n-Pr-Ph),
$NHCO_2CH_2$-(4-i-Pr-Ph), $NHCO_2CH_2$-(4-n-Bu-Ph),
$NHCO_2CH_2$-(4-s-Bu-Ph), $NHCO_2CH_2$-(4-i-Bu-Ph),
$NHCO_2CH_2$-(4-t-Bu-Ph), $NHCO_2CH_2$-(4-t-Am-Ph),
$NHCO_2CH_2$-(4-n-Hex-Ph), $NHCO_2CH_2$-(2-NO_2-Ph),
$NHCO_2CH_2$-(3-NO_2-Ph), $NHCO_2CH_2$-(4-NO_2,-Ph),
$NHCO_2CH_2$-(2-MeOCO-Ph), $NHCO_2CH_2$-(3-MeOCO-Ph),
$NHCO_2CH_2$-(3,4-di-Me-Ph), $NHCO_2CH_2$-(2,4-di-Me-Ph),
$NHCO_2CH_2$-(4-MeOCO-Ph), $NHCO_2CH_2$-(2-CF_3-Ph),
$NHCO_2CH_2$-(3-CF_3-Ph), $NHCO_2CH_2$-(4-CF_3-Ph),
$NHCO_2CH_2$-(2-CH_3O-Ph), $NHCO_2CH_2$-(3-CF_3O-Ph),
$NHCO_2CH_2$-(4-CF_3O-Ph), $NHCO_2CH_2$-(4-CF_3CF_2O-Ph),
$NHCO_2CH_2$-(3-MeCO-Ph), $NHCO_2CH_2$-(3-HOCO-Ph),
$NHCO_2CH_2$-(4-HOCO-Ph), $NH(CO)SMe$, $NH(CO)SEt$,
$NHCOCO_2Me$, $NHCOCO_2Et$, $NHCOCO_2$-n-Pr, $NHCOCO_2$-i-Pr,
$NHCOCO_2$-n-Bu, $NHCOCO_2$-s-Bu, $NHCOCO_2$-i-Bu,
$NHCOCO_2$-t-Bu, $NHCOCO_2CH_2Ph$, $NHCOCO_2Ph$,
$N(Me)COCO_2Me$, $N(Me)COCO_2Et$, $N(Me)COCO_2$-n-Pr,
$N(Me)COCO_2$-i-Pr, $N(Me)COCO_2$-n-Bu,
$N(Me)COCO_2$-s-Bu, $N(Me)COCO_2$-i-Bu,
$N(Me)COCO_2$-t-Bu, $N(Me)COCO_2CH_2Ph$, $N(Me)COCO_2Ph$,
$N(Et)COCO_2Me$, $N(Et)COCO_2Et$, $N(Et)COCO_2$-n-Pr,
$N(Et)COCO_2$-i-Pr, $N(Et)COCO_2$-n-Bu,
$N(Et)COCO_2$-s-Bu, $N(Et)COCO_2$-i-Bu,
$N(Et)COCO_2$-t-Bu, $N(Et)COCO_2CH_2Ph$, $N(Et)COCO_2Ph$,
$NHSCCl_3$, $NHS(O)CCl_3$, $NHS(O)Me$, $NHS(O)Et$,
$NHS(O)$-n-Pr, $NHS(O)$-i-Pr, $NHS(O)$-n-Bu, $NHS(O)$-s-Bu,
$NHS(O)$-i-Bu, $NHS(O)$-t-Bu, $NHS(O)CH_2Ph$, $NHS(O)Ph$,
$N(Me)SCCl_3$, $N(Me)S(O)CCl_3$, $N(Me)S(O)Me$,
$N(Me)S(O)Et$, $N(Me)S(O)$-n-Pr, $N(Me)S(O)$-n-Pr,
$N(Me)S(O)$-n-Bu, $N(Me)S(O)$-s-Bu, $N(Me)S(O)$-i-Bu,
$N(Me)S(O)$-t-Bu, $N(Me)S(O)CH_2Ph$, $N(Me)S(O)Ph$,
$N(Et)SCCl_3$, $N(Et)S(O)CCl_3$, $N(Et)S(O)Me$,
$N(Et)S(O)Et$, $N(Et)S(O)$-n-Pr, $N(Et)S(O)$-i-Pr,
$N(Et)S(O)$-n-Bu, $N(Et)S(O)$-s-Bu, $N(Et)S(O)$-i-Bu,
$N(Et)S(O)$-t-Bu, $N(Et)S(O)CH_2Ph$, $N(Et)S(O)Ph$,
$NHSO_2NH_2$, $NHSO_2N(Me)_2$, $NHSO_2NHMe$,
$NHSO_2NHEt$, NHSO$_2$NH-n-Pr, NHSO$_2$NH-i-Pr, NHSO$_2$NH-n-Bu, NHSO$_2$NHPh, NHSO$_2$NH-(2-Cl-Ph), NHSO$_2$NH-(3-Cl-Ph), NHSO$_2$NH-(4-Cl-Ph), NHSO$_2$NHCH$_2$Ph, NHCSNH$_2$, NHCON(Me)$_2$, NHCON(Me)OMe, NHCONHMe, NHCONHEt, NHCONH-n-Pr, NHCONH-i-Pr, NHCONH-n-Bu, NHCONH-s-Bu, NHCONH-i-Bu, NHCONH-t-Bu, NHCONHCH$_2$Ph, NHCONHPh, NHCON(Me)Ph, NHCON(OMe)Ph, N=C(OMe)N(Me)$_2$, N=C(SMe)N(Me)$_2$, NHCONHSO$_2$Me, NHCONHSO$_2$Et, NHCONHSO$_2$-n-Pr, NHCONHSO$_2$-i-Pr, NHCONHSO$_2$-n-Bu, NHCONHSO$_2$-s-Bu, NHCONHSO$_2$-i-Bu, NHCONHSO$_2$-t-Bu, NHCONHSO$_2$CH$_2$Ph, NHCONHSO$_2$Ph, NHCONHSO$_2$CF$_3$, NHCSN(Me)2, NHCSN(Me)OMe, NHCSNHMe, NHCSNHEt, NHCSNH-n-Pr, NHCSNH-i-Pr, NHCSNH-n-Bu, NHCSNH-s-Bu, NHCSNH-s-Bu, NHCSNH-i-Bu, NHCSNH-t-Bu, NHCSNHCH$_2$Ph, NHCSNHPh, NHCONHCOMe, NHCONHCOEt, NHCONHCO-(2,6-di-Cl-Ph), NHCONHCO-(2,6-di-F-Ph), NHCSNHCO-(2,6-di-Cl-Ph), NHCSNHCO-(2,6-di-F-Ph), N=CHN(Me)$_2$, N=CHN(Et)$_2$, N=CHN(Et)Me, N=CHH(Et)Ph, N=C(OMe)Ph, N=C(Me)Ph, -Q30, -(4-Me-Q30), -(4-CF$_3$-Q30), -(4-Ph-Q30), -Q31, -Q32, -(4-Me-Q32), -(4-Me-Q33), -(4-H-Q33), -Q34, -(2,6-di-Me-Q34), -Q35, -(2,6-d i-Me-Q35), -Q36, -(3-Me-Q36), -Q37, -Q38, -(3-Me-Q38), -(4-Me-Q38), -(5-Me-Q38), -Q39, -(3-Me-Q39), -(4-Me-Q39), -(5-Me-Q39), -(6-Me-Q39) -(6-Me-Q40), -(6-H-Q40), -(6,3-di-Me-Q40), -(6,4-di-Me-Q40), -(6,5-di-Me-Q40), -Q41, -Q42, -(2,5-di-Me-Q42), -Q43, -Q44, -(3,4-di-Me-Q44), -(3,4-di-Cl-Q44), -Q45, -Q46, -(4-H-Q47), -(4-Me-Q47), -(4-CH$_2$CO$_2$Me-Q47), -(4-CO$_2$Me-Q47), NH-(4,6-di-MeO-Q14), NH-(4,6-di-Me-Q14), CONH-(4,6-di-MeO-Q14), CONH-(4,6-di-Me-Q14), NH-(5-CF-$_3$-3-Cl-Q1), NHP(O)(OMe)$_2$, NHP(O)(OEt)$_2$, NHP(O)(OEt)S-n-Pr, NHP(O)(OEt)SPh, NHP(O)(OEt)O-n-Pr, NHP(O)(O-i-Pr)$_2$, NHP(O)(O-n-Pr)$_2$, NHP(S)(OMe)$_2$, NHP(S)(OEt)$_2$, NHP(S)(OEt)S-n-Pr, NHP(S)(OEt)SPh NHP(S)(OEt)O-n-Pr, NHP(S)(O-i-Pr)$_2$, NHP(S)(O-n-Pr)$_2$, NHP(O)(OMe)Me, NHP(O)(OEt)Me, NHP(O)(OEt)Ph, NHP(O)(O-i-Pr)Me, NHP(O)(O)-n-Pr)Me, NHP(S)(OMe)Me, NHP(S)(OEt)Me, NHP(S)(OEt)Ph, NHP(S)(O)-i-Pr)Me, NHP(S)(O)-n-Pr)Me, NHP(O)(OMe)OH, NHP(O)(OEt)OH, NHCH$_2$CO$_2$H, NHCH$_2$CO$_2$Me, NHCH$_2$CO$_2$Et, NHCH$_2$CO$_2$-n-Pr, NHCH$_2$CO$_2$-i-Pr, NHCH$_2$CO$_2$n-Bu, NHCH$_2$CO$_2$-s-Bu, NHCH$_2$CO$_2$-i-Bu, NHCH$_2$CO$_2$-t-Bu, NHCH$_2$CO$_2$-t-Am, NHCH$_2$CO$_2$-n-Am, NHCH$_2$CO$_2$-n-Hex, NHCH$_2$CO$_2$CH$_2$(CH$_2$)$_6$Me, NHCH$_2$CO$_2$CH$_2$Ph, NHCH$_2$CO$_2$Ph, NHCH$_2$CO$_2$CH$_2$CO$_2$Me, NHCH$_2$CO$_2$CH$_2$CO$_2$Et, NHCH$_2$CO$_2$CH(Me)CO$_2$Me, NHCH$_2$CO$_2$CH(Me)CO$_2$Et, N(Me)CH$_2$CO$_2$Me, N(Me)CH$_2$CO$_2$Et, N(Et)CH$_2$CO$_2$Me, N(Et)CH$_2$CO$_2$Et, N(COMe)CH$_2$CO$_2$Me, N(COMe)CH$_2$CO$_2$Et, N(COPh) CH$_2$CO$_2$Me, N(COPh) CH$_2$CO$_2$Et, NHCH(Me)CO$_2$H, NHCH(Me)CO$_2$Me, NHCH(Me)CO$_2$Et, NHCH(Me)CO$_2$-n-Pr, NHCH(Me)CO$_2$-i-Pr, NHCH(Me)CO$_2$-n-Bu, NHCH(Me)CO$_2$-s-Bu, NHCH(Me)CO$_2$-i-Bu, NHCH(Me)CO$_2$-t-Bu, NHCH(Me)CO$_2$-t-Am, NHCH(Me)CO$_2$-n-Am, NHCH(Me)CO$_2$-n-Hex, NHCH(Me)CO$_2$CH$_2$(CH$_2$)$_6$Me, NHCH(Me)CO$_2$CH$_2$Ph, NHCH(Me)CO$_2$Ph, NHCH(Me)CO$_2$CH$_2$CO$_2$Me, NHCH(Me)CO$_2$CH$_2$CO$_2$Et, NHCH(Me)CO$_2$CH(Me)CO$_2$Me, NHCH(Me)CO$_2$CH(Me)CO$_2$Et, N(Me)CH(Me)CO$_2$Me, N(Me)CH(Me)CO$_2$Et, N(Et)CH(Me)CO$_2$Me, N(Et)CH(Me)CO$_2$Et, N(COMe)CH(Me)CO$_2$Me, (COMe)CH(Me)CO$_2$Et, N(COPh)CH(Me)CO$_2$Me, N(COPh)CH(Me)CO$_2$Et, NHCH(Et)CO$_2$H, NHCH(Et)CO$_2$Me, NHCH(Et)CO$_2$Et, NHCH(Et)CO$_2$-n-Pr, NHCH(Et)CO$_2$-i-Pr, NHCH(Et)CO$_2$-n-Bu, NHCH(Et)CO$_2$-s-Bu, NHCH(Et)CO$_2$-i-Bu, NHCH(Et)CO$_2$-t-Bu, NHCH(Et)CO$_2$-t-Am, NHCH(Et)CO$_2$-n-Am, NHCH(Et)CO$_2$-n-Hex, NHCH(Et)CO$_2$CH$_2$(CH$_2$)$_6$Me, NHCH(Et)CO$_2$CH$_2$Ph, NHCH(Et)CO$_2$Ph, NHCH(CH$_2$OMe)CO$_2$H, NHCH(CH$_2$OMe)CO$_2$Me, NHCH(CH$_2$OMe)CO$_2$Et, NHCH(CH$_2$OMe)CO$_2$-n-Pr, NHCH(CH$_2$OMe)CO$_2$-i-Pr, NHCH(CH$_2$OMe)CO$_2$-n-Bu, NHCH(CH$_2$OMe)CO$_2$-Bu, NHCH(CH$_2$OMe)CO$_2$-i-Bu, NHCH(CH$_2$OMe)CO$_2$-t-Bu, NHCH(CH$_2$OMe)CO$_2$-t-Am, NHCH(CH$_2$OMe)CO$_2$-n-Am, NHCH(CH$_2$OMe)CO$_2$-n-Hex, NHCH(CH$_2$OMe)CO$_2$CH$_2$(CH$_2$)$_6$Me, NHCH(CH$_2$OMe)CO$_2$CH$_2$Ph, NHCH(CH$_2$OMe)CO$_2$Ph, NHCH(CH$_2$OEt)CO$_2$H, NHCH(CH$_2$OEt)CO$_2$Me, NHCH(CH$_2$OEt)CO$_2$Et, NHCH(CH$_2$OEt)CO$_2$-n-Pr NHCH(CH$_2$OEt)CO$_2$-i-Pr, NHCH(CH$_2$OEt)CO$_2$-n-Bu, NHCH(CH$_2$OEt)CO$_2$-s-Bu, NHCH(CH$_2$OEt)CO$_2$-i-Bu, NHCH(CH$_2$OEt)CO$_2$-t-Bu, NHCH(CH$_2$OEt)CO$_2$-t-Am, NHCH(CH$_2$OEt)CO$_2$-n-Am, NHCH(CH$_2$OEt)CO$_2$-n-Hex, NHCH(CH$_2$OEt)CO$_2$CH$_2$(CH$_2$)$_6$Me, NHCH(CH$_2$OEt)CO$_2$CH$_2$Ph, NHCH(CH$_2$OEt)CO$_2$Ph, NHCH(SMe)CO$_2$H, NHCH(SMe)CO$_2$Me, NHCH(SMe)CO$_2$Et, NHCH(SMe)CO$_2$-n-Pr, NHCH(SMe)CO$_2$-i-Pr, NHCH(SMe)CO₂-n-Bu, NHCH(SMe)CO₂-s-Bu, NHCH(SMe)CO₂-i-Bu, NHCH(SMe)CO₂-t-Bu, NHCH(SMe)CO₂-t-Am, NHCH(SMe)CO₂-n-Am, NHCH(SMe)CO₂-n-Hex, NHCH(SMe)CO₂CH₂(CH₂)₆Me, NHCH(SMe)CO₂CH₂Ph, NHCH(SMe)CO₂Ph, NHCH(i-Pr)CO₂Me, NHCH(i-Pr)CO₂Et, NHCH(i-Pr)CO₂-n-Pr, NHCH(i-Pr)CO₂-i-Pr, NHCH(n-Pr)CO₂Me, NHCH(n-Pr)CO₂Et, NHCH(n-Pr)CO₂-n-Pr, NHCH(n-Pr)CO₂-i-Pr, NHCH(Ph)CO₂Me, NHCH(Ph)CO₂Et, NHCH(Ph)CO₂-n-Pr, NHCH(Ph)CO₂-i-Pr, NHCH₂CONH₂, NHCH₂CONHMe, NHCH₂CONHEt, NHCH₂CONH-n-Pr, NHCH₂CONH-i-Pr, NHCH₂CONH-n-Bu, NHCH₂CONH-s-Bu, NHCH₂CONH-i-Bu, NHCH₂CONH-t-Bu, NHCH₂CONH-t-Am, NHCH₂CONH-n-Am, NHCH₂CONH-n-Hex, NHCH₂CONHCH₂(CH₂)₆Me, NHCH₂CONHCH₂Ph, NHCH₂CONHPh, NHCH₂CONHCH₂CO₂Me, NHCH₂CONHCH₂CO₂Et, NHCH₂CONHCH(Me)CO₂Me, NHCH₂CONHCH(Me)CO₂Et, N(Me)CH₂CONHMe, N(Me)CH₂CONHEt, N(Et)CH₂CONHMe, N(Et)CH₂CONHEt, N(COMe)CH₂CONHMe, N(COMe)CH₂CONHEt, N(COPh)CH₂CONHMe, N(COPh)CH₂CONHEt, NHCH(Me)CONH₂, NHCH(Me)CONHMe, NHCH(Me)CONHEt, NHCH(Me)CONH-n-Pr, NHCH(Me)CONH-i-Pr, NHCH(Me)CONH-n-Bu, NHCH(Me)CONH-s-Bu, NHCH(Me)CONH-i-Bu, NHCH(Me)CONH-t-Bu, NHCH(Me)CONH-t-Am, NHCH(Me)CONH-n-Am, NHCH(Me)CONH-n-Hex, NHCH(Me)CONHCH₂(CH₂)₆Me, NHCH(Me)CONHCH₂Ph, NHCH(Me)CONHPh, NHCH(Me)CONHCH₂CO₂Me, NHCH(Me)CONHCH₂CH₂Et, NHCH(Me)CONHCH(Me)CO₂Me, NHCH(Me)CONHCH(Me)CO₂Et, NHCH(Me)CONHCH(Me)Ph, N(Me)CH(Me)CONHMe, N(Me)CH(Me)CONHEt, N(Et)CH(Me)CONHMe, N(Et)CH(Me)CONHEt, N(COMe)CH(Me)CONHMe, N(COMe)CH(Me)CONHEt, N(COPh)CH(Me)CONHMe, N(COPh)CH(Me)CONHEt, NHCH(Et)CONH₂, NHCH(Et)CONHMe, NHCH(Et)CONHEt, NHCH(Et)CONH-n-pr, NHCH(Et)CONH-i-Pr, NHCH(Et)CONH-n-Bu, NHCH(Et)CONH-s-Bu, NHCH(Et)CONH-i-Bu, NHCH(Et)CONH-t-Bu, NHCH(Et)CONH-t-Am, NHCH(Et)CONH-n-Am, NHCH(Et)CONH-n-Hex, NHCH(Et)CONHCH₂(CH₂)₆Me, NHCH(Et)CONHCH₂Ph, NHCH(Et)CONHPh, NHCH(CH₂OMe)CONH₂, NHCH(CH₂OMe)CONHMe, NHCH(CH₂OMe)CONHEt, NHCH(CH₂OMe)CONH-n-Pr, NHCH(CH₂OMe)CONH-i-Pr, NHCH(CH₂OMe)CONH-n-Bu, NHCH(CH₂OMe)CONH-s-Bu, NHCH(CH₂OMe)CONH-i-Bu, NHCH(CH₂OMe)CONH-t-Bu, NHCH(CH₂OMe)CONH-t-Am, NHCH(CH₂OMe)CONH-n-Am, NHCH(CH₂OMe)CONH-n-Hex, NHCH(CH₂OMe)CONHCH₂(CH₂)₆Me, NHCH(CH₂OMe)CONHCH₂Ph, NHCH(CH₂OMe)CONHPh, NHCH(CH₂OEt)CONH₂, NHCH(CH₂OEt)CONHMe, NHCH(CH₂OEt)CONHEt, NHCH(CH₂OEt)CONH-n-Pr, NHCH(CH₂OEt)CONH-i-Pr, NHCH(CH₂OEt)CONH-n-Bu, NHCH(CH₂OEt)CONH-s-Bu, NHCH(CH₂OEt)CONH-i-Bu, NHCH(CH₂OEt)CONH-t-Bu, NHCH(CH₂OEt)CONH-t-Am, NHCH(CH₂OEt)CONH-n-Am, NHCH(CH₂OEt)CONH-n-Hex, NHCH(CH₂OEt)CONHCH₂(CH₂)₆Me, NHCH(CH₂OEt)CONHCH₂Ph, NHCH(CH₂OEt)CONHPh, NHCH(SMe)CONH₂, NHCH(SMe)CONHMe, NHCH(SMe)CONHEt, NHCH(SMe)CONH-n-Pr, NHCH(SMe)CONH-i-Pr, NHCH(SMe)CONH-n-Bu, NHCH(SMe)CONH-s-Bu, NHCH(SMe)CONH-i-Bu, NHCH(SMe)CONH-t-Bu, NHCH(SMe)CONH-t-Am, NHCH(SMe)CONH-n-Am, NHCH(SMe)CONH-n-Hex, NHCH(SMe)CONHCH₂(CH₂)₆Me, NHCH(SMe)CONHCH₂Ph, NHCH(SMe)CONHPh, NHCH(i-Pr)CONHMe, NHCH(i-Pr)CONHEt, NHCH(i-Pr)CONH-n-Pr, NHCH(i-Pr)CONH-i-Pr, NHCH(n-Pr)CONHMe, NHCH(n-Pr)CONHEt, NHCH(n-Pr)CONH-n-Pr, NHCH(n-Pr)CONH-i-Pr, NHCH(Ph)CONHMe, NHCH(Ph)CONHEt, NHCH(Ph)CONH-n-Pr, NHCH(Ph)CONH-i-Pr, NHCH₂CN, NHCH(Me)CN, NHC(Me)₂CN, N(Me)CH₂CN, N(Me)CH(Me)CN, N(Me)C(Me)₂CN, NHCH₂CH₂CO₂Me, NHCH(Me)CH₂CO₂Me, NHCH₂CH₂CH₂CO₂Me, NHCH₂CH₂CH₂CH₂CO₂Me, NHCH₂CH₂CO₂Et, NHCH(Me)CH₂CO₂Et, NHCH₂CH₂CH₂CO₂Et, NHCH₂CH₂CH₂CH₂CO₂Et, NHCH₂P(O)(OMe)₂, NHCH₂P(O)(OEt)₂, NHCH₂P(O)(O-i-Pr)₂, NHCH₂P(O)(O)-n-Pr)₂, NHCH₂P(S)(OMe)₂, NHCH₂P(S)(OEt)₂, NHCH₂P(S)(O-i-Pr)₂, NHCH₂P(S)(O)-n-Pr)₂, NHCH₂P(O)(OMe)Me, NHCH₂P(O)(OEt)Me, NHCH₂P(O)(O-i-Pr)Me, NHCH₂P(O)(O)-n-Pr)Me, NHCH₂P(S)(OMe)Me, NHCH₂P(S)(OEt)Me, NHCH₂P(S)(O-i-Pr)Me,)Me, NHCH₂P(S)(O)-n-Pr)Me, NHCH₂P(O)(OMe)OH, NHCH₂P(O)(OEt)OH, NHCH₂P(O)(OH)₂, NHCH₂CH₂P(O)(OMe)₂, NHCH₂CH₂P(O)(OEt)₂, NHCH₂CH₂P(O)(O-i-Pr)₂, NHCH₂CH₂P(O)(O-n-Pr)₂, NHCH₂CH₂P(S)(OMe)₂, NHCH₂CH₂P(S)(OEt)₂, NHCH₂CH₂P(S)(O-i-Pr)₂, NHCH₂CH₂P(S)(O-n-Pr)₂, NHCH₂CH₂P(O)(OMe)Me, NHCH₂CH₂P(O)(OEt)Me, NHCH₂CH₂P(O)(O-i-Pr)Me, NHCH₂CH₂P(O)(O)-n-Pr)Me, NHCH₂CH₂P(S)(OMe)Me, NHCH$_2$CH$_2$P(S)(OEt)Me, NHCH$_2$CH$_2$P(S)(O)-i-Pr)Me,
NHCH$_2$CH$_2$P(S)(O)-n-Pr)Me, NHCH$_2$CH$_2$P(O)(OMe)OH,
NHCH$_2$CH$_2$P(O)(OEt)OH, NHCH$_2$CH$_2$P(O)(OH)$_2$,
NHCH(P(O)(OMe)$_2$)$_2$, NHCH(P(O)(OEt)$_2$)$_2$,
NHCH(P(O)(O-i-Pr)$_2$)$_2$, NHCH(P(O)(O-n-Pr)$_2$)$_2$,
NHCH(P(O)(OH)$_2$)$_2$, NHCH(P(O)(OMe)$_2$)(P(O)(OH)$_2$),
NHCH(P(O)(OEt)$_2$)(P(O)(OH)$_2$),
NHCH(P(O)(O-i-Pr)$_2$)(P(O)(OH)$_2$),
NHCH(P(O)(O-n-Pr)$_2$)(P(O)(OH)$_2$),
NHC(Me)(P(O)(OMe)$_2$)$_2$, NHC(Me)(P(O)(OEt)$_2$)$_2$,
NHC(Me)(P(O)(O)-i-Pr)$_2$)$_2$, NHC(Me)(P(O)(O-n-Pr)$_2$)$_2$,
NHC(Me)(P(O)(OH)$_2$)$_2$,
NHC(Me)(P(O)(OMe)$_2$)(P(O)(OH)$_2$),
NHC(Me)(P(O)(OEt)$_2$)(P(O)(OH)$_2$),
NHC(Me)(P(O)(O-i-Pr)$_2$)(P(O)(OH)$_2$),
NHC(Me)(P(O)(O)-n-Pr)$_2$)(P(O)(OH)$_2$),
N(SO$_2$Me)CH$_2$CO$_2$H, N(SO$_2$Me)CH$_2$CO$_2$Me,
N(SO$_2$Me)CH$_2$CO$_2$Et, N(SO$_2$Me)CH$_2$CO$_2$-n-Pr,
N(SO$_2$Me)CH$_2$CO$_2$-i-Pr, N(SO$_2$Me)CH$_2$CO$_2$-n-Bu,
N(SO$_2$Me)CH$_2$CO$_2$-s-Bu, N(SO$_2$Me)CH$_2$CO$_2$-i-Bu,
N(SO$_2$Me)CH$_2$CO$_2$-t-Bu, N(SO$_2$Me)CH$_2$CO$_2$-t-Am,
N(SO$_2$Me)CH$_2$CO$_2$-n-Am, N(SO$_2$Me)CH$_2$CO$_2$-n-Hex,
N(SO$_2$Me)CH$_2$CO$_2$CH$_2$(CH$_2$)$_6$Me,
N(SO$_2$Me)CH$_2$CO$_2$CH$_2$Ph, N(SO$_2$Me)CH$_2$CO$_2$Ph,
N(SO$_2$Me)CH$_2$CONH$_2$, N(SO$_2$Me)CH$_2$CONHMe,
N(SO$_2$Me)CH$_2$CONHEt, H(SO$_2$Me)CH$_2$CONH-n-Pr,
N(SO$_2$Me)CH$_2$CONH-i-Pr, N(SO$_2$Me)CH$_2$CONH-n-Bu,
N(SO$_2$Me)CH$_2$CONH-s-Bu, N(SO$_2$Me)CH$_2$CONH-i-Bu,
N(SO$_2$Me)CH$_2$CONH-t-Bu, N(SO$_2$Me)CH$_2$CONH-t-Am,
N(SO$_2$Me)CH$_2$CONH-n-Am, N(SO$_2$Me)CH$_2$CONH-n-Hex,
N(SO$_2$Me)CH$_2$CONHCH$_2$(CH$_2$)$_6$Me,
N(SO$_2$Me)CH$_2$CONHCH$_2$Ph, N(SO$_2$Me)CH$_2$CONHPh,
N(SO$_2$Me)CH(Me)CO$_2$H, N(SO$_2$Me)CH(Me)CO$_2$Me,
N(SO$_2$Me)CH(Me)CO$_2$Et, N(SO$_2$Me)CH(Me)CO$_2$-n-Pr,
N(SO$_2$Me)CH(Me)CO$_2$-i-Pr, N(SO$_2$Me)CH(Me)CO$_2$-n-Bu,
N(SO$_2$Me)CH(Me)CO$_2$-s-Bu, N(SO$_2$Me)CH(Me)CO$_2$-i-Bu,
N(SO$_2$Me)CH(Me)CO$_2$-t-Bu, N(SO$_2$Me)CH(Me)CO$_2$-t-Am,
N(SO$_2$Me)CH(Me)CO$_2$-n-Am, N(SO$_2$Me)CH(Me)CO$_2$-n-Hex,
N(SO$_2$Me)CH(Me)CO$_2$CH$_2$(CH$_2$)$_6$Me,
N(SO$_2$Me)CH(Me)CO$_2$CH$_2$Ph, N(SO$_2$Me)CH Me)CO$_2$Ph,
N(SO$_2$Me)CH(Me)CONH$_2$, N(SO$_2$Me)CH(Me)CONHMe,
N(SO$_2$Me)CH(Me)CONHEt, N(SO$_2$Me)CH(Me)CONH-n-Pr,
N(SO$_2$Me)CH(Me)CONH-i-Pr, N(SO$_2$Me)CH(Me)CONH-n-Bu,
N(SO$_2$Me)CH(Me)CONH-s-Bu, N(SO$_2$Me)CH(Me)CONH-i-Bu,
N(SO$_2$Me)CH(Me)CONH-t-Bu, N(SO$_2$Me)CH(Me)CONH-t-Am,
N(SO$_2$Me)CH(Me)CONH-n-Am, N(SO$_2$Me)CH(Me)CONH-n-Hex,
N(SO$_2$Me)CH(Me)CONHCH$_2$(CH$_2$)$_6$Me,
N(SO$_2$Me)CH(Me)CONHCH$_2$Ph, N(SO$_2$Me)CH(Me)CONHPh,
N(SO$_2$Et)CH$_2$CO$_2$H, N(SO$_2$Et)CH$_2$CO$_2$Me,
N(SO$_2$Et)CH$_2$CO$_2$Et, N(SO$_2$Et)CH$_2$CO$_2$-n-Pr,
N(SO$_2$Et)CH$_2$CO$_2$-i-Pr, N(SO$_2$Et)CH$_2$CO$_2$-n-Bu,
N(SO$_2$Et)CH$_2$CO$_2$-s-Bu, N(SO$_2$Et)CH$_2$CO$_2$-i-Bu,
N(SO$_2$Et)CH$_2$CO$_2$-t-Bu, N(SO$_2$Et)CH$_2$CO$_2$-t-Am,
N(SO$_2$Et)CH$_2$CO$_2$-n-Am, N(SO$_2$Et)CH$_2$CO$_2$-n-Hex,
N(SO$_2$Et)CH$_2$CO$_2$CH$_2$(CH$_2$)$_6$Me,
N(SO$_2$Et)CH$_2$CO$_2$CH$_2$Ph, N(SO$_2$Et)CH$_2$CO$_2$Ph,
N(SO$_2$Et)CH$_2$CONH$_2$, N(SO$_2$Et)CH$_2$CONHMe,
N(SO$_2$Et)CH$_2$CONHEt, N(SO$_2$Et)CH$_2$CONH-n-Pr,
N(SO$_2$Et)CH$_2$CONH-i-Pr, N(SO$_2$Et)CH$_2$CONH-n-Bu,
N(SO$_2$Et)CH$_2$CONH-s-Bu, N(SO$_2$Et)CH$_2$CONH-i-Bu,
N(SO$_2$Et)CH$_2$CONH-t-Bu, N(SO$_2$Et)CH$_2$CONH-t-Am,
N(SO$_2$Et)CH$_2$CONH-n-Am, N(SO$_2$Et)CH$_2$CONH-n-Hex,
N(SO$_2$Et)CH$_2$CONHCH$_2$(CH$_2$)$_6$Me,
N(SO$_2$Et)CH$_2$CONHCH$_2$Ph, N(SO$_2$Et)CH$_2$CONHPh,
N(SO$_2$Et)CH(Me)CO$_2$H, N(SO$_2$Et)CH(Me)CO$_2$Me,
N(SO$_2$Et)CH(Me)CO$_2$Et, N(SO$_2$Et)CH(Me)CO$_2$-n-Pr,
N(SO$_2$Et)CH(Me)CO$_2$-i-Pr, N(SO$_2$Et)CH(Me)CO$_2$-n-Bu,
N(SO$_2$Et)CH(Me)CO$_2$-s-Bu, N(SO$_2$Et)CH(Me)CO$_2$-i-Bu,
N(SO$_2$Et)CH(Me)CO$_2$-t-Bu, N(SO$_2$Et)CH(Me)CO$_2$-t-Am,
N(SO$_2$Et)CH(Me)CO$_2$-n-Am, N(SO$_2$Et)CH(Me(CO$_2$-n-Hex,
N(SO$_2$Et)CH(Me)CO$_2$CH$_2$(CH$_2$)$_6$Me,
N(SO$_2$Et)CH(Me)CO$_2$CH$_2$Ph, N(SO$_2$Et)CH(Me)CO$_2$Ph,
N(SO$_2$Et)CH(Me)CONH$_2$, N(SO$_2$Et)CH(Me)CONHMe,
N(SO$_2$Et)CH(Me)CONHEt, N(SO$_2$Et)CH(Me)CONH-n-Pr,
N(SO$_2$Et)CH(Me)CONH-i-Pr, N(SO$_2$Et)CH(Me)CONH-n-Bu,
N(SO$_2$Et)CH(Me)CONH-s-Bu, N(SO$_2$Et)CH(Me)CONH-i-Bu,
N(SO$_2$Et)CH(Me)CONH-t-Bu, N(SO$_2$Et)CH(Me)CONH-t-Am,
N(SO$_2$Et)CH(Me)CONH-n-Am, N(SO$_2$Et)CH(Me)CONH-n-Hex,
N(SO$_2$Et)CH(Me)CONHCH$_2$(CH$_2$)$_6$Me,
N(SO$_2$Et)CH(Me)CONHCH$_2$Ph, N(SO$_2$Et)CH(Me)CONHPh,
NHMe, NHEt, NH-n-Pr, NH-i-Pr, NH-n-Bu, NH-s-Bu, NH-i-Bu, NH-t-Bu, NH-t-Am, NH-n-Am, NH-n-Hex, NHCH$_2$(CH$_2$)$_6$Me, NHCH$_2$Ph, NHPh, NH-(2-NO$_2$-Ph),
NH-(4-NO$_2$-Ph), NH-(2,4-di-NO$_2$-Ph),
NH-(2-NO$_2$-4-CF$_3$-Ph), NH-(4-NO$_2$-2-CF$_3$-Ph),
NH-(2,6-di-NO$_2$-4-CF$_3$-Ph),
NH-(2,4-di-NO$_2$-6-CF$_3$-Ph),
NH-(2,4,6,-tri-NO$_2$-Ph),
NH-(2,6-di-NO$_2$-4-CF$_3$-5-Cl-Ph), NHCH$_2$-(2-F-Ph),
NHCH$_2$-(3-F-Ph), NHCH$_2$-(4-F-Ph), NHCH$_2$-(2-Cl-Ph),
NHCH$_2$-(3-Cl-Ph), NHCH$_2$-(4-Cl-Ph), NHCH$_2$-(2-Br-Ph),
NHCH$_2$-(3-Br-Ph), NHCH$_2$-(4-Br-Ph), NHCH$_2$-(2-I-Ph),
NHCH$_2$-(3-I-Ph), NHCH$_2$-(4-I-Ph), NHCH$_2$-(2-Me-Ph), NHCH₂-(3-Me-Ph), NHCH₂-(4-Me-Ph), NHCH₂-(2-MeO-Ph),
NHCH₂-(3-MeO-Ph), NHCH₂-(4-MeO-Ph), NHCH₂-(4-Et-Ph),
NHCH₂-(4-n-Pr-Ph), NHCH₂-(4-i-Pr-Ph),
NHCH₂-(4-n-Bu-Ph), NHCH₂-(4-s-Bu-Ph),
NHCH₂-(4-i-Bu-Ph), NHCH₂-(4-t-Bu-Ph),
NHCH₂-(4-t-Am-Ph), NHCH₂-(4-n-Hex-Ph),
NHCH₂-(2-NO₂-Ph), NHCH₂-(3-NO₂-Ph),
NHCH₂-(4-NO₂-Ph), NHCH₂-(2-MeOCO-Ph),
NHCH₂-(3-MeOCO-Ph), NHCH₂-(4-MeOCO-Ph),
NHCH₂-(2-CF₃-Ph), NHCH₂-(3-CF₃-Ph),
NHCH₂-(4-CF₃-Ph), NHCH₂-(2-CH₃O-Ph),
NHCH₂-(3-CF₃O-Ph), NHCH₂-(4-CF₃O-Ph),
NHCH₂-(4-CF₃CF₂O-Ph), NHCH₂-(3-MeCO-Ph),
NHCH₂-(3-HOCO-Ph), NHCH₂-(4-HOCO-Ph), NHCH(Me)Ph,
NHCH₂CH₂Ph, N(Me)₂, N(Et)₂, N(n-Pr)₂, N(i-Pr)₂,
N(Me)Et, N(n-Bu)₂, N(s-Bu)₂, N(i-Bu)₂, N(t-Bu)₂,
N(t-Am)₂, N(n-Am)₂, NHCF₃, NHCH₂CF₃,
NHCH₂CH₂CF₃, NHCH(Me)CF₃, NHCH(CF₃)₂,
NHCH(F)CF₃, NH(CF₂)₃CF₃, NH(CF₂)₅CF₃,
NH(CF₂)₇CF₃, NHCCl₃, NHCHCl₂, NHCH₂CCl₃,
NHCH₂Cl, NHCH₂CH₂Cl, NHCH₂CH₂CH₂Cl,
NHCH₂CH(Cl)Me, NHCH₂C(Cl)=CH₂, NHCH(OH)CCl₃,
NHCH=CH₂, NHCH₂CH=CH₂, NHCH(Me)CH=CH₂,
NHC(Me)₂CH=CH₂, NHCH₂C≡CH, NHCH(Me)C≡CH,
NHC(Me)₂C≡CH, NHCH₂C(Me)=CH₂, N(CH₂CH=CH₂)₂,
N(CH₂C≡CH)₂, NH-c-Pr, NH-c-Bu, NH-c-Pen, NH-c-Hex,
NHCH₂-c-Pr, NHCH₂-c-Bu, NHCH₂-c-Pen, NHCH₂-c-Hex,
NHCH₂OMe, NHCH₂OEt, NHCH₂O-n-Pr, NHCH₂O-i-Pr,
NHCH₂O-n-Bu, NHCH₂O-s-Bu, NHCH₂O-i-Bu, NHCH₂O-t-Bu,
NHCH₂O-t-Am, NHCH₂O-n-Am, NHCH₂O-n-Hex,
NHCH₂OCH₂(CH₂)₆Me, NHCH₂OCH₂Ph, NHCH₂OPh,
NHCH₂CH₂OMe, NHCH₂CH₂OEt, NHCH₂CH₂O-n-Pr,
NHCH₂CH₂O-i-Pr, NHCH₂CH₂O-n-Bu, NHCH₂CH₂O-s-Bu,
NHCH₂CH₂O-i-Bu, NHCH₂CH₂O-t-Bu, NHCH₂CH₂O-t-Am,
NHCH₂CH₂O-n-Am, NHCH₂CH₂O-n-Hex,
NHCH₂CH₂OCH₂(CH₂)₆Me, NHCH₂CH₂OCH₂Ph,
NHCH₂CH₂OPh, NHCH(Me)CH₂OMe, NHCH(Me)CH₂OEt,
NHCH(Me)CH₂O-n-Pr, NHCH(Me)CH₂O-i-Pr,
NHCH(Me)CH₂O-n-Bu, NHCH(Me)CH₂O-s-Bu,
NHCH(Me)CH₂O-i-Bu, NHCH(Me)CH₂O-t-Bu,
NHCH(Me)CH₂O-t-Am, NHCH(Me)CH₂O-n-Am,
NHCH(Me)CH₂O-n-Hex, NHCH(Me)CH₂OCH₂(CH₂)₆Me,
NHCH(Me)CH₂OCH₂Ph, NHCH(Me)CH₂OPh, NHOCH₂CO₂Me,
NHOCH₂CO₂Et, N(Me)OCH₂CO₂Me, N(Me)OCH₂CO₂Et,
NHNH₂, NHNHSO₂Me, NHNHSO₂Et, NHNHSO₂-n-Pr,
NHNHSO₂-i-Pr, NHNHSO₂-n-Bu, NHNHSO₂-s-Bu,
NHNHSO₂-i-Bu, NHNHSO₂-t-Bu, NHNHSO₂-t-Am,
NHNHSO₂-n-Am, NHNHSO₂-n-Hex, NHNHSO₂CH₂(CH₂)₆Me,
NHNHSO₂CH₂Ph, NHNHSO₂Ph, NHN(SO₂Me)₂,
NHN(SO₂Et)₂, NHN(SO₂-n-Pr)₂, NHN(SO₂i-Pr)₂,
NHN(SO₂-n-Bu)₂, NHN(SO₂-s-Bu)₂, NHN(SO₂-i-Bu)₂,
NHN(SO₂-t-Bu)₂, NHN(SO₂-t-Am)₂, NHN(SO₂-n-Am)₂,
NHN(SO₂-n-Hex)₂, NHN(SO₂CH₂(CH₂)₆Me)₂,
NHN(SO₂CH₂Ph)₂, NHN(SO₂Ph)₂, N(NH₂)SO₂Me,
N(NH₂)SO₂Et, N(NH₂)SO₂-n-Pr, N(NH₂)SO₂-i-Pr,
N(NH₂)SO₂-n-Bu, N(NH₂)SO₂-s-Bu,
N(NH₂)SO₂-i-Bu, N(NH₂)SO₂-t-Bu,
N(NH₂)SO₂-t-Am, N(NH₂)SO₂-n-Am,
N(NH₂)SO₂-n-Hex, N(NH₂)SO₂CH₂(CH₂)₆Me,
N(NH₂)SO₂CH₂Ph, N(NH₂)SO₂Ph,
N(COCH₂Cl)CH₂OEt, N(COCH₂Br)CH₂OEt,
N(COCH₂Cl)CH₂O-i-Pr, N(COCH₂Br)CH₂O-i-Pr,
N(COCH₂Cl)CH₂O-n-Bu, N(COCH₂Br)CH₂O-n-Bu,
N(COCH₂Cl)CH₂O-i-Bu, N(COCH₂Br)CH₂O-i-Bu,
N(COCH₂Cl)CH₂CO₂Me, N(COCH₂Br)CH₂CO₂Et,
N(COCH₂Cl)CH(Me)CH₂OMe, N(COCH₂Br)CH(Me)CH₂OMe
N(COCH₂OMe)CH(Me)CO₂Me, N(COCH₂OMe)CH(Me)CO₂Et,
N(COCH₂OMe)-Q15, N(COCH₂OMe)-Q15, N(COCH₂OMe)-Q17,
N(COCH₂OMe)-Q17, N(COCH₂OMe)-Q19, N(COCH₂OMe)-Q19,
N(CO-Q16)CH(Me)CO₂Me, N(COCH₂Cl)-Q17,
N(COCH₂Br)-Q17, N(COCH₂Cl)-Q15, N(COCH₂Br)-Q15,
N(COCH₂Cl)CH(Me)CO₂Me, N(COCH₂Br)CH(Me)CO₂Et,
N(COCH₂Ph)CH(Me)CO₂Me, N(COCH₂Ph)CH(Me)CO₂Et,
N(CO-c-Pr)-Q15, N(CO-c-Pr)-Q15, N(CO-Q18)CH(Me)CO₂Me,
N(CO-Q18)CH(Me)CO₂Et, NHCOCH₂OMe, NHCOCH₂OEt,
NHCH=NOMe, NHCH=NOEt, NHCH₂CON(Me)-(6MeO-Q1),
NHCH₂CON(Me)-(6-Me-Q1), NHCH₂CON(Me)Ph,
NHCOCH₂CH(Me)CH₂CO₂H, NHCOCH₂CH(Me)CH₂CO₂Me,
NHCOCH₂CH(Me)CH₂CO₂Et,
NHCOCH₂CH(CF₃)CH₂CO₂H,
NHCOCH₂CH(CF₃)CH₂CO₂Me,
NHCOCH₂CH(CF₃)CH₂CO₂SMe, NHCH₂SO₂Me,
NHCH₂SEt, NHCH₂SO₂Et, NHCH₂CN
in which Q1 to Q47 are as shown below.

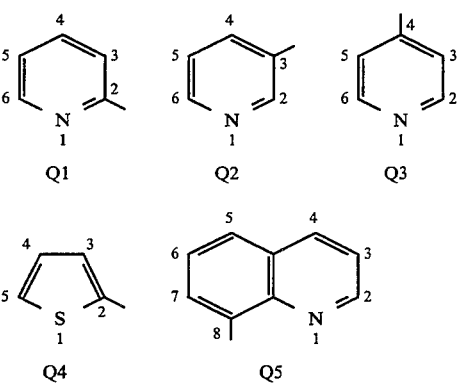

-continued

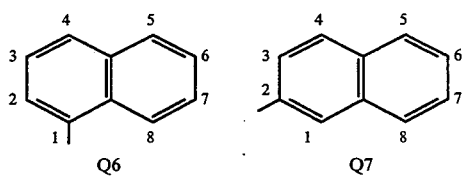
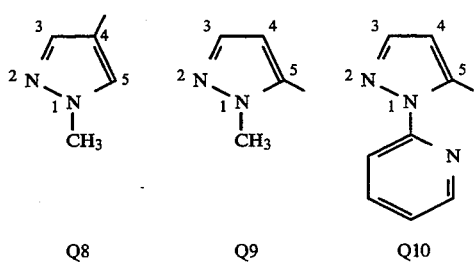
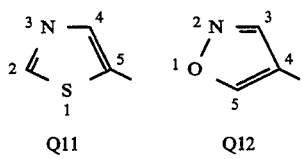
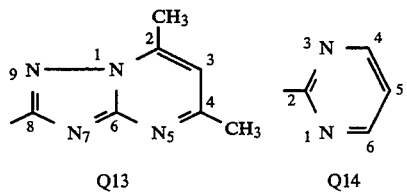
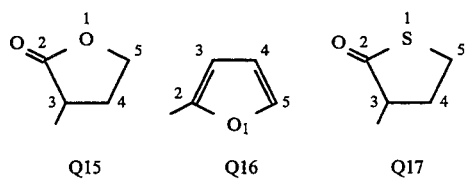
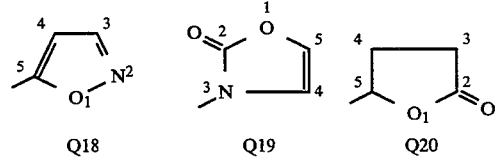
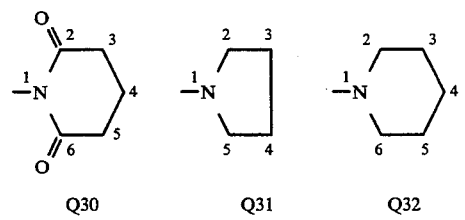
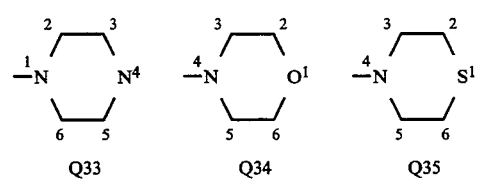

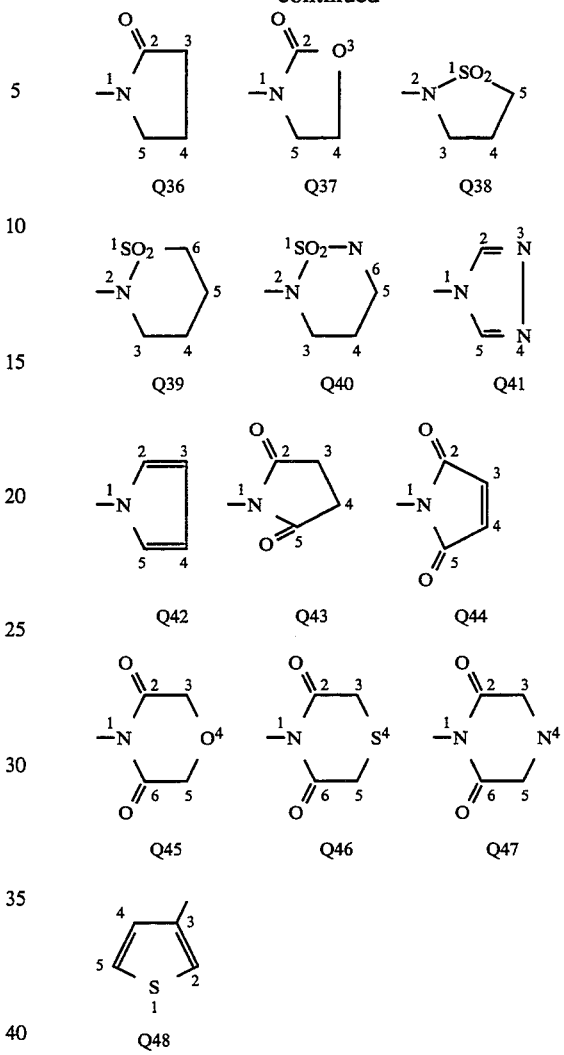

Next, formulation examples of preparations using the compound of the present invention are shown specifically. The formulation examples of the present invention are not limited only to these. In the following formulation examples, all "part"s mean part by weight.

| [Wettable powder] | |
| --- | --- |
| The compound of the present invention | 5–80 parts |
| Solid carrier | 10–85 parts |
| Surfactant | 1–10 parts |
| Others | 1–5 parts |

As the others, there may be mentioned, for example, an anticaking agent.

| [Emulsifiable concentrate] | |
| --- | --- |
| The compound of the present invention | 1–30 parts |
| Liquid carrier | 30–95 parts |
| Surfactant | 5–15 parts |
| [Flowable formulation] | |
| The compound of the present invention | 5–70 parts |
| Liquid carrier | 15–65 parts |
| Surfactant | 5–12 parts |
| Others | 5–30 parts |

As the others, there may be mentioned, for example, an antifreezing agent, a thickening agent, etc.

| [Granular wettable formulation (Dry flowable formulation)] | |
|---|---|
| The compound of the present invention | 20–90 parts |
| Solid carrier | 10–60 parts |
| Surfactant | 1–20 parts |
| [Granule] | |
| The compound of the present invention | 0.01–10 parts |
| Solid carrier | 90–99.99 parts |
| Others | 0–5 parts |
| [Formulation example 1] Wettable powder | |
| Present compound D-12 | 50 parts |
| Zeeklite PFP | 43 parts |
| (Kaolin series clay: produced by Zeeklite Kogyo K.K., tradename) | |
| Sorpol 5050 | 2 parts |
| (Anionic surfactant: produced by Toho Chemical Industry Co., Ltd., tradename) | |
| Runox 1000C | 3 parts |
| (Anionic surfactant: produced by Toho Chemical Industry Co., Ltd., tradename) | |
| Carplex #80 (Anticaking agent) | 2 parts |
| (White carbon: produced by Shionogi & Co., Ltd., tradename) | |

The above components were uniformly mixed and pulverized to prepare a wettable powder.

| [Formulation example 2] Emulsifiable concentrate | |
|---|---|
| Present compound D-12 | 3 parts |
| Xylene | 76 parts |
| Isophorone | 15 parts |
| Sorpol 3005X | 6 parts |
| (Mixture of an nonionic surfactant and an anionic surfactant: produced by Toho Chemical Industry Co., Ltd., tradename) | |

The above components were uniformly mixed to prepare an emulsifiable concentrate.

| [Formulation example 3] Flowable formulation | |
|---|---|
| Present compound D-12 | 35 parts |
| Agrizole S-711 | 8 parts |
| (Nonionic surfactant: produced by Kao Corporation, tradename) | |
| Runox 1000C | 0.5 part |
| (Anionic surfactant: produced by Toho Chemical Industry Co., Ltd., tradename) | |
| 1% Rodopole water | 20 parts |
| (Thickening agent: produced by Rhone-Poulenc S.A., tradename) | |
| Ethylene glycol (Antifreezing agent) | 8 parts |
| Water | 28.5 parts |

The above components were uniformly mixed to prepare a flowable formulation.

| [Formulation example 4] Granular wettable powder (Dry flowable formulation) | |
|---|---|
| Present compound D-12 | 75 parts |
| Isobam No. 1 | 10 parts |
| (Anionic surfactant: produced by Kuraray Isoprene Chemical Co., Ltd., tradename) | |
| Vanilex N | 5 parts |
| (Anionic surfactant: produced by Sanyo Kokusaku Pulp Co., Ltd., tradename) | |
| Carplex #80 | 10 parts |
| (White carbon: produced by Shionogi & Co., Ltd., tradename) | |

The above components were uniformly mixed and finely pulverized to prepare a dry flowable formulation.

| [Formulation example 5] Granule | |
|---|---|
| Present compound D-12 | 0.1 part |
| Bentonite | 55.0 parts |
| Talc | 44.9 parts |

The above components were uniformly mixed and pulverized, and then a small amount of water was added and the mixture was stirred, mixed and kneaded, and granulated by an extrusion type granulating machine and dried to prepare granule.

| [Formulation example 6] Wettable powder | |
|---|---|
| Present compound D-15 | 50 parts |
| Zeeklite PFP | 43 parts |
| (Kaolin series clay: produced by Zeeklite Kogyo K.K., tradename) | |
| Sorpol 5050 | 2 parts |
| (Anionic surfactant: produced by Toho Chemical Industry Co., Ltd., tradename) | |
| Runox 1000C | 3 parts |
| (Anionic surfactant: produced by Toho Chemical Industry Co., Ltd., tradename) | |
| Carplex #80 (Anticaking agent) | 2 parts |
| (White carbon: produced by Shionogi & Co., Ltd., tradename) | |

The above components were uniformly mixed and pulverized to prepare a wettable powder.

| [Formulation example 7] Emulsifiable concentrate | |
|---|---|
| Present compound D-15 | 3 parts |
| Xylene | 76 parts |
| Isophorone | 15 parts |
| Sorpol 3005X | 6 parts |
| (Mixture of an nonionic surfactant and an anionic surfactant: produced by Toho Chemical Industry Co., Ltd., tradename) | |

The above components were uniformly mixed to prepare an emulsifiable concentrate.

| [Formulation example 8] Flowable formulation | |
|---|---|
| Present compound D-15 | 35 parts |
| Agrizole S-711 | 8 parts |
| (Nonionic surfactant: produced by Kao Corporation, tradename) | |
| Runox 1000C | 0.5 part |
| (Anionic surfactant: produced by Toho Chemical Industry Co., Ltd., tradename) | |
| 1% Rodopole water | 20 parts |
| (Thickening agent: produced by Rhone-Poulenc S.A., tradename) | |
| Ethylene glycol (Antifreezing agent) | 8 parts |
| Water | 28.5 parts |

The above components were uniformly mixed to prepare a flowable formulation.

| [Formulation example 9] Granular wettable powder (Dry flowable formulation) | |
|---|---|
| Present compound D-15 | 75 parts |
| Isobam No. 1 | 10 parts |
| (Anionic surfactant: produced by Kuraray Isoprene Chemical Co., Ltd., tradename) | |
| Vanilex N | 5 parts |

| [Formulation example 9] Granular wettable powder (Dry flowable formulation) | |
|---|---|
| (Anionic surfactant: produced by Sanyo Kokusaku Pulp Co., Ltd., tradename) | |
| Carplex #80 | 10 parts |
| (White carbon: produced by Shionogi & Co., Ltd., tradename) | |

The above components were uniformly mixed and finely pulverized to prepare a dry flowable formulation.

| [Formulation example 10] Granule | |
|---|---|
| Present compound D-15 | 0.1 part |
| Bentonite | 55.0 parts |
| Talc | 44.9 parts |

The above components were uniformly mixed and pulverized, and then a small amount of water was added and the mixture was stirred, mixed and kneaded, and granulated by an extrusion type granulating machine and dried to prepare granule.

| [Formulation example 11] Wettable powder | |
|---|---|
| Present compound D-16 | 50 parts |
| Zeeklite PFP | 43 parts |
| (Kaolin series clay: produced by Zeeklite Kogyo K.K., tradename) | |
| Sorpol 5050 | 2 parts |
| (Anionic surfactant: produced by Toho Chemical Industry Co., Ltd., tradename) | |
| Runox 1000C | 3 parts |
| (Anionic surfactant: produced by Toho Chemical Industry Co., Ltd., tradename) | |
| Carplex #80 (Anticaking agent) | 2 parts |
| (White carbon: produced by Shionogi & Co., Ltd., tradename) | |

The above components were uniformly mixed and pulverized to prepare a wettable powder.

| [Formulation example 12] Emulsifiable concentrate | |
|---|---|
| Present compound D-16 | 3 parts |
| Xylene | 76 parts |
| Isophorone | 15 parts |
| Sorpol 3005X | 6 parts |
| (Mixture of an nonionic surfactant and an anionic surfactant: produced by Toho Chemical Industry Co., Ltd., tradename) | |

The above components were uniformly mixed to prepare an emulsifiable concentrate.

| [Formulation example 13] Flowable formulation | |
|---|---|
| Present compound D-16 | 35 parts |
| Agrizole S-711 | 8 parts |
| (Nonionic surfactant: produced by Kao Corporation, tradename) | |
| Runox 1000C | 0.5 part |
| (Anionic surfactant: produced by Toho Chemical Industry Co., Ltd., tradename) | |
| 1% Rodopole water | 20 parts |
| (Thickening agent: produced by Rhone-Poulenc S.A., tradename) | |
| Ethylene glycol (Antifreezing agent) | 8 parts |
| Water | 28.5 parts |

The above components were uniformly mixed to prepare a flowable formulation.

| [Formulation example 14] Granular wettable powder (Dry flowable formulation) | |
|---|---|
| Present compound D-16 | 75 parts |
| Isobam No. 1 | 10 parts |
| (Anionic surfactant: produced by Kuraray Isoprene Chemical Co., Ltd., tradename) | |
| Vanilex N | 5 parts |
| (Anionic surfactant: produced by Sanyo Kokusaku Pulp Co., Ltd., tradename) | |
| Carplex #80 | 10 parts |
| (White carbon: produced by Shionogi & Co., Ltd., tradename) | |

The above components were uniformly mixed and finely pulverized to prepare a wettable powder.

| [Formulation example 15] Granule | |
|---|---|
| Present compound D-16 | 0.1 part |
| Bentonite | 55.0 parts |
| Talc | 44.9 parts |

The above components were uniformly mixed and pulverized, and then a small amount of water was added and the mixture was stirred, mixed and kneaded, and granulated by an extrusion type granulating machine and dried to prepare granule.

| [Formulation example 16] Wettable powder | |
|---|---|
| Present compound D-22 | 50 parts |
| Zeeklite PFP | 43 parts |
| (Kaolin series clay: produced by Zeeklite Kogyo K.K., tradename) | |
| Sorpol 5050 | 2 parts |
| (Anionic surfactant: produced by Toho Chemical Industry Co., Ltd., tradename) | |
| Runox 1000C | 3 parts |
| (Anionic surfactant: produced by Toho Chemical Industry Co., Ltd., tradename) | |
| Carplex #80 (Anticaking agent) | 2 parts |
| (White carbon: produced by Shionogi & Co., Ltd., tradename) | |

The above components were uniformly mixed and pulverized to prepare a wettable powder.

| [Formulation example 17] Emulsifiable concentrate | |
|---|---|
| Present compound D-22 | 3 parts |
| Xylene | 76 parts |
| Isophorone | 15 parts |
| Sorpol 3005X | 6 parts |
| (Mixture of an nonionic surfactant and an anionic surfactant: produced by Toho Chemical Industry Co., Ltd., tradename) | |

The above components were uniformly mixed to prepare an emulsifiable concentrate.

| [Formulation example 18] Flowable formulation | |
|---|---|
| Present compound D-22 | 35 parts |
| Agrizole S-711 | 8 parts |
| (Nonionic surfactant: produced by Kao Corporation, tradename) | |
| Runox 1000C | 0.5 part |
| (Anionic surfactant: produced by Toho Chemical Industry Co., Ltd., tradename) | |
| 1% Rodopole water | 20 parts |

| [Formulation example 18] Flowable formulation | |
| --- | --- |
| (Thickening agent: produced by Rhone-Poulenc S.A., tradename) | |
| Ethylene glycol (Antifreezing agent) | 8 parts |
| Water | 28.5 parts |

The above components were uniformly mixed to prepare a flowable formulation.

| [Formulation example 19] Granular wettable powder (Dry flowable formulation) | |
| --- | --- |
| Present compound D-22 | 75 parts |
| Isobam No. 1 | 10 parts |
| (Anionic surfactant: produced by Kuraray Isoprene Chemical Co., Ltd., tradename) | |
| Vanilex N | 5 parts |
| (Anionic surfactant: produced by Sanyo Kokusaku Pulp Co., Ltd., tradename) | |
| Carplex #80 | 10 parts |
| (White carbon: produced by Shionogi & Co., Ltd., tradename) | |

The above components were uniformly mixed and finely pulverized to prepare a wettable powder.

| [Formulation example 20] Granule | |
| --- | --- |
| Present compound D-22 | 0.1 part |
| Bentonite | 55.0 parts |
| Talc | 44.9 parts |

The above components were uniformly mixed and pulverized, and then a small amount of water was added and the mixture was stirred, mixed and kneaded, and granulated by an extrusion type granulating machine and dried to prepare granule.

| [Formulation example 21] Wettable powder | |
| --- | --- |
| Present compound D-24 | 50 parts |
| Zeeklite PFP | 43 parts |
| (Kaolin series clay: produced by Zeeklite Kogyo K.K., tradename) | |
| Sorpol 5050 | 2 parts |
| (Anionic surfactant: produced by Toho Chemical Industry Co., Ltd., tradename) | |
| Runox 1000C | 3 parts |
| (Anionic surfactant: produced by Toho Chemical Industry Co., Ltd., tradename) | |
| Carplex #80 (Anticaking agent) | 2 parts |
| (White carbon: produced by Shionogi & Co., Ltd., tradename) | |

The above components were uniformly mixed and pulverized to prepare a wettable powder.

| [Formulation example 22] Emulsifiable concentrate | |
| --- | --- |
| Present compound D-24 | 3 parts |
| Xylene | 76 parts |
| Isophorone | 15 parts |
| Sorpol 3005X | 6 parts |
| (Mixture of an nonionic surfactant and an anionic surfactant: produced by Toho Chemical Industry Co., Ltd., tradename) | |

The above components were uniformly mixed to prepare an emulsifiable concentrate.

| [Formulation example 23] Flowable formulation | |
| --- | --- |
| Present compound D-24 | 35 parts |
| Agrizole S-711 | 8 parts |
| (Nonionic surfactant: produced by Kao Corporation, tradename) | |
| Runox 1000C | 0.5 part |
| (Anionic surfactant: produced by Toho Chemical Industry Co., Ltd., tradename) | |
| 1% Rodopole water | 20 parts |
| (Thickening agent: produced by Rhone-Poulenc S.A., tradename) | |
| Ethylene glycol (Antifreezing agent) | 8 parts |
| Water | 28.5 parts |

The above components were uniformly mixed to prepare a flowable formulation.

| [Formulation example 24] Granular wettable powder (Dry flowable formulation) | |
| --- | --- |
| Present compound D-24 | 75 parts |
| Isobam No. 1 | 10 parts |
| (Anionic surfactant: produced by Kuraray Isoprene Chemical Co., Ltd., tradename) | |
| Vanilex N | 5 parts |
| (Anionic surfactant: produced by Sanyo Kokusaku Pulp Co., Ltd., tradename) | |
| Carplex #80 | 10 parts |
| (White carbon: produced by Shionogi & Co., Ltd., tradename) | |

The above components were uniformly mixed and finely pulverized to prepare a wettable powder.

| [Formulation example 25] Granule | |
| --- | --- |
| Present compound D-24 | 0.1 part |
| Bentonite | 55.0 parts |
| Talc | 44.9 parts |

The above components were uniformly mixed and pulverized, and then a small amount of water was added and the mixture was stirred, mixed and kneaded, and granulated by an extrusion type granulating machine and dried to prepare granule.

For practical use, the wettable powder, the emulsifiable concentrate, the flowable formulation and the granular wettable powder are diluted 50 to 1000-fold with water and applied so that the dose of an effective component is 0.0001 to 10 kg per one hectare (ha).

Next, availability of the compounds of the present invention as a herbicide is explained specifically by referring to the following test examples.

[Test example 1] Test of herbicidal effect by soil treatment

In a plastic box having a length of 15 cm, a width of 22 cm and a depth of 6 cm was charged a sterilized diluvial soil, and *Echinochloa crus-galli* (barnyardgrass), *Digitaria adscendens* (Crabgrass), *Cyperus microira* (annual sedge), *Solanum nigrum* (black nightshade), *Galinsoga ciliata* (hairy galinsoga), *Rorippa indica* (indian field cress), rice, corn, wheat, soybean and cotton were sewed mixedly and after covering with soil about 1 cm, chemicals were applied uniformly using a small sized spray on the surface of the soil so that the dose of the effective ingredient is as predetermined. The chemical liquor at applying was used by diluting the preparation prepared according to the above formulation examples, etc, with water and this was applied. After 3 weeks from the application of the chemical liquor, herbicidal effect against respective weeds and crops were examined according to the following judgement standard. The results are shown in Table 3.

Judgement Standard

5-Weed killing rate 90% or more (substantially completely killed)
4-Weed killing rate 70 to 90%
3-Weed killing rate 40 to 70%
2-Weed killing rate 20 to 40%
1-Weed killing rate 5 to 20%
0-Weed killing rate 5% or lower (substantially no effect)

The above weed killing rate was obtained by the following equation by after measuring an above-ground green forage weight in the chemical treated area and an above-ground green forage weight in the non-treated area.

Weed killing rate=(1−(above-ground green forage weight in chemical treated area/above-ground green forage weight in non-treated area))×100

Test Example 2

Test of Herbicidal Effect by Foliar Treatment

In a plastic box having a length of 15 cm, a width of 22 cm and a depth of 6cm was charged a sterilized diluvial soil, and seeds of *Echinochloa crus-galli* (barnyardgrass), *Digitaria adscendens* (Crabgrass), Cyperus microira (annual sedge), *Solanum nigrum* (black nightshade), *Galinsoga ciliata* (hairy galinsoga), *Rorippa indica* (indian field cress), rice, corn, wheat, soybean, cotton and sugar beet were spot-sewed and after covering with soil about 1 cm. Each kinds of plants were reached to 2 to 3-leaf stage, chemicals were applied uniformly to the foliar portion so that the dose of the effective ingredient is as predetermined.

The chemical liquor at applying was used by diluting the preparation prepared according to the above formulation examples, etc., with water and this was applied using a small sized spray to whole surface of the foilar portion. After 4 weeks from the application of the chemical liquor, herbicidal effect against respective weeds and crops were examined according to the judgement standard in Test example 1. The results are shown in Table 4.

Test Example 3

Test of Herbicidal Effect Under Watering Condition

In 1/5000 are Wagner pot was placed a diluvial soil and water was charged therein and mixed to make a watering condition with a water depth of 2 cm. Each seed of *Echinochloa crus-galli* (barnyardgrass), *Monochoria vaginalis (ducksalad)*, *Rotala indica* (toothcap) and *Scirpus juncoides* (bulrush) was sewed mixedly in the above pot. Also, root of *Sagittaria pygmaea* (arrowhead) and *Cyperus serotinus* (perennial flat sedge) were placed therein and rice seedlings at 2.5-leaf stage was transplanted. The pot was placed in a green house at 25° to 30° C. to grow plants, and 2 days after sewing, diluted chemical solution was added dropwise to the water surface with a messpipet so that the dose of the chemical as predetermined. After 3 weeks from the dropping of the chemical liquor, herbicidal effect against respective weeds and crops were examined according to the judgement standard in Test Example 1. The results are shown in Table 5.

Symbols in the respective tables mean as shown below,
N: *Echinochloa crus-galli* (barnyardgrass)
M: *Digitaria adscendens* (crabgrass)
K: *Cyperus microiria* (annual sedge)
H: *Solanum nigrum* (black nightshade)
D: *Galinsoga ciliata* (hairy galinsoga)
I: *Rorippa indica* (Indian field grass)
R: rice
T: corn
W: wheat
S: soybean
C: cotton
B: sugar beet
a: *Scirpus juncoides* (bulrush)
b: *Monochoria vaginalis* (ducksalad)
c: *Rotala indica* (toothcap)
d: *Sagittaria pygmaea* (arrowhead)
e: *Cyperus serotinus* (perennial flat sedge)
f: transplanted rice

TABLE 3

| Compound No. | Dose (g/a) | N | M | K | H | D | I | R | T | W | S | C |
|---|---|---|---|---|---|---|---|---|---|---|---|---|
| D-1 | 0.4 | 3 | 2 | 5 | 5 | 5 | 5 | 0 | 0 | 0 | 0 | 1 |
| D-2 | 0.4 | 3 | 2 | 5 | 5 | 2 | 5 | 1 | 0 | 0 | 0 | 0 |
| D-3 | 0.4 | 2 | 3 | 5 | 5 | 5 | 5 | 0 | 0 | 0 | 0 | 0 |
| D-4 | 0.4 | 4 | 5 | 5 | 5 | 5 | 5 | 0 | 0 | 0 | 0 | 0 |
| D-5 | 0.4 | 2 | 4 | 5 | 5 | 5 | 5 | 1 | 0 | 0 | 0 | 1 |
| D-6 | 0.4 | 2 | 3 | 4 | 5 | 5 | 5 | 0 | 0 | 0 | 0 | 1 |
| D-7 | 0.4 | 4 | 3 | 5 | 5 | 5 | 5 | 1 | 0 | 0 | 0 | 0 |
| D-8 | 0.4 | 2 | 2 | 4 | 5 | 5 | 5 | 0 | 0 | 0 | 0 | 0 |
| D-9 | 0.4 | 2 | 4 | 5 | 5 | 5 | 5 | 0 | 0 | 0 | 0 | 0 |
| D-10 | 0.4 | 1 | 2 | 4 | 5 | 5 | 5 | 0 | 0 | 0 | 0 | 0 |
| D-11 | 0.4 | 2 | 2 | 3 | 5 | 5 | 5 | 0 | 0 | 0 | 0 | 0 |
| D-12 | 0.4 | 4 | 5 | 5 | 5 | 5 | 5 | 1 | 0 | 0 | 0 | 2 |
| D-13 | 0.4 | 2 | 4 | 4 | 5 | 5 | 5 | 0 | 0 | 0 | 0 | 1 |
| D-14 | 0.1 | 5 | 5 | 5 | 5 | 5 | 5 | 1 | 0 | 0 | 0 | 0 |
| D-15 | 0.4 | 4 | 5 | 5 | 5 | 5 | 5 | 1 | 1 | 0 | 1 | 2 |
| D-16 | 0.1 | 1 | 3 | 5 | 5 | 5 | 5 | 1 | 0 | 0 | 0 | 0 |
| D-17 | 0.4 | 1 | 2 | 1 | 5 | 4 | 5 | 0 | 0 | 0 | 0 | 1 |
| D-18 | 0.4 | 2 | 1 | 5 | 5 | 5 | 5 | 0 | 0 | 0 | 0 | 0 |
| D-19 | 0.4 | 3 | 4 | 5 | 5 | 5 | 5 | 0 | 0 | 0 | 0 | 0 |
| D-20 | 0.1 | 3 | 5 | 5 | 5 | 5 | 5 | 1 | 0 | 0 | 0 | 1 |
| D-21 | 0.4 | 3 | 5 | 5 | 5 | 5 | 5 | 0 | 0 | 0 | 1 | 2 |
| D-22 | 0.1 | 5 | 5 | 5 | 5 | 5 | 5 | 1 | 1 | 1 | 0 | 0 |
| D-23 | 0.1 | 4 | 5 | 5 | 5 | 5 | 5 | 0 | 1 | 0 | 0 | 1 |
| D-24 | 0.1 | 4 | 5 | 5 | 5 | 5 | 5 | 1 | 0 | 1 | 0 | 1 |
| D-25 | 0.1 | 3 | 4 | 5 | 5 | 5 | 5 | 1 | 0 | 0 | 0 | 1 |
| D-26 | 0.1 | 3 | 4 | 5 | 5 | 5 | 5 | 0 | 0 | 0 | 0 | 0 |
| D-27 | 0.1 | 4 | 3 | 5 | 5 | 5 | 5 | 0 | 1 | 0 | 0 | 1 |
| D-28 | 0.1 | 3 | 4 | 5 | 5 | 5 | 5 | 0 | 0 | 0 | 0 | 0 |
| D-29 | 0.4 | 1 | 2 | 2 | 5 | 5 | 5 | 0 | 0 | 0 | 0 | 0 |
| D-30 | 0.4 | 3 | 4 | 5 | 5 | 5 | 5 | 1 | 0 | 1 | 0 | 1 |
| D-31 | 0.4 | 4 | 5 | 5 | 5 | 5 | 5 | 0 | 0 | 0 | 0 | 0 |
| D-32 | 0.4 | 2 | 3 | 5 | 5 | 5 | 5 | 0 | 0 | 0 | 0 | 0 |
| D-33 | 0.4 | 1 | 2 | 3 | 4 | 5 | 5 | 0 | 0 | 0 | 0 | 0 |
| D-34 | 0.4 | 1 | 2 | 4 | 5 | 5 | 5 | 0 | 0 | 0 | 0 | 0 |
| D-35 | 0.4 | 1 | 3 | 5 | 5 | 3 | 5 | 0 | 0 | 0 | 0 | 0 |
| D-36 | 1.6 | 1 | 2 | 5 | 5 | 3 | 5 | 0 | 0 | 0 | 0 | 0 |
| D-37 | 1.6 | 2 | 3 | 5 | 5 | 5 | 5 | 1 | 0 | 0 | 0 | 0 |
| D-38 | 1.6 | 2 | 4 | 5 | 5 | 5 | 5 | 0 | 0 | 0 | 0 | 0 |
| D-39 | 1.6 | 4 | 5 | 5 | 5 | 5 | 5 | 0 | 0 | 1 | 1 | 1 |
| D-40 | 1.6 | 3 | 4 | 5 | 5 | 5 | 5 | 0 | 1 | 1 | 0 | 1 |
| D-41 | 0.4 | 3 | 4 | 5 | 5 | 5 | 5 | 0 | 0 | 0 | 0 | 0 |
| D-42 | 1.6 | 2 | 4 | 5 | 5 | 5 | 5 | 0 | 0 | 0 | 0 | 0 |
| D-43 | 1.6 | 3 | 4 | 5 | 5 | 5 | 5 | 0 | 0 | 0 | 0 | 0 |
| D-44 | 0.4 | 3 | 4 | 5 | 5 | 5 | 5 | 0 | 0 | 0 | 0 | 0 |
| D-48 | 0.4 | 1 | 1 | 5 | 5 | 5 | 5 | 0 | 0 | 0 | 0 | 0 |
| D-49 | 0.4 | 1 | 3 | 5 | 5 | 5 | 5 | 1 | 0 | 0 | 0 | 0 |
| D-50 | 0.4 | 4 | 4 | 5 | 5 | 5 | 5 | 2 | 0 | 1 | 0 | 0 |
| D-51 | 0.4 | 3 | 3 | 5 | 5 | 5 | 5 | 0 | 0 | 0 | 0 | 0 |
| D-52 | 0.4 | 2 | 2 | 5 | 5 | 2 | 5 | 0 | 0 | 0 | 0 | 0 |
| D-53 | 0.4 | 3 | 3 | 5 | 5 | 5 | 5 | 1 | 0 | 1 | 0 | 0 |
| D-54 | 0.4 | 1 | 2 | 4 | 5 | 5 | 5 | 0 | 1 | 1 | 1 | 0 |
| D-55 | 0.4 | 0 | 1 | 2 | 5 | 5 | 5 | 0 | 0 | 0 | 0 | 0 |
| D-56 | 0.4 | 1 | 1 | 5 | 5 | 5 | 5 | 0 | 0 | 0 | 0 | 0 |
| D-57 | 0.4 | 1 | 1 | 5 | 5 | 5 | 5 | 0 | 0 | 0 | 0 | 0 |
| D-58 | 0.4 | 4 | 5 | 5 | 5 | 5 | 5 | 0 | 0 | 1 | 1 | 1 |

TABLE 3-continued

| Compound No. | Dose (g/a) | N | M | K | H | D | I | R | T | W | S | C |
|---|---|---|---|---|---|---|---|---|---|---|---|---|
| D-59 | 0.4 | 4 | 5 | 5 | 5 | 5 | 5 | 0 | 1 | 1 | 1 | 1 |
| D-60 | 0.4 | 2 | 4 | 5 | 5 | 3 | 5 | 0 | 0 | 0 | 0 | 0 |
| D-61 | 0.1 | 5 | 5 | 5 | 5 | 5 | 5 | 3 | 2 | 2 | 1 | 2 |
| D-62 | 0.4 | 4 | 4 | 5 | 5 | 5 | 5 | 1 | 0 | 0 | 0 | 2 |
| D-63 | 0.4 | 3 | 2 | 5 | 5 | 5 | 5 | 0 | 0 | 0 | 0 | 0 |
| D-64 | 0.4 | 2 | 1 | 5 | 5 | 5 | 5 | 0 | 0 | 0 | 0 | 0 |
| D-65 | 0.4 | 1 | 2 | 5 | 5 | 5 | 5 | 0 | 0 | 1 | 0 | 0 |
| D-66 | 0.1 | 5 | 5 | 5 | 5 | 5 | 5 | 0 | 0 | 0 | 0 | 0 |
| D-67 | 0.1 | 1 | 2 | 5 | 5 | 5 | 5 | 0 | 0 | 0 | 0 | 0 |
| D-68 | 0.4 | 5 | 5 | 5 | 5 | 5 | 5 | 1 | 0 | 0 | 2 | 2 |
| D-69 | 0.4 | 5 | 5 | 5 | 5 | 5 | 5 | 0 | 0 | 3 | 0 | 3 |
| D-70 | 1.6 | 4 | 5 | 5 | 5 | 5 | 5 | 0 | 0 | 0 | 0 | 0 |
| D-71 | 1.6 | 0 | 2 | 5 | 5 | 5 | 5 | 0 | 0 | 0 | 0 | 1 |
| D-72 | 1.6 | 4 | 4 | 5 | 5 | 5 | 5 | 0 | 0 | 0 | 0 | 0 |
| D-73 | 1.6 | 5 | 5 | 5 | 5 | 5 | 5 | 0 | 0 | 1 | 0 | 0 |
| D-74 | 0.4 | 5 | 5 | 5 | 5 | 5 | 5 | 1 | 1 | 0 | 1 | 1 |
| D-75 | 1.6 | 5 | 5 | 5 | 5 | 5 | 5 | 1 | 1 | 1 | 1 | 1 |
| D-76 | 0.4 | 5 | 5 | 5 | 5 | 5 | 5 | 0 | 0 | 0 | 0 | 0 |
| D-77 | 0.4 | 5 | 5 | 5 | 5 | 5 | 5 | 0 | 0 | 0 | 0 | 0 |
| D-78 | 0.4 | 5 | 5 | 5 | 5 | 5 | 5 | 1 | 2 | 1 | 3 | 3 |
| D-79 | 1.6 | 5 | 5 | 5 | 5 | 5 | 5 | 2 | 1 | 0 | 3 | 1 |
| D-80 | 0.4 | 5 | 5 | 5 | 5 | 5 | 5 | 0 | 0 | 0 | 0 | 0 |
| D-81 | 1.6 | 2 | 3 | 5 | 5 | 5 | 5 | 1 | 0 | 0 | 0 | 0 |
| D-82 | 0.4 | 5 | 5 | 5 | 5 | 5 | 5 | 3 | 1 | 2 | 1 | 0 |
| D-83 | 1.6 | 2 | 5 | 5 | 5 | 5 | 5 | 0 | 0 | 0 | 3 | 3 |
| D-84 | 1.6 | 3 | 5 | 5 | 5 | 5 | 5 | 1 | 0 | 0 | 0 | 0 |
| D-85 | 1.6 | 4 | 4 | 5 | 5 | 4 | 5 | 0 | 0 | 0 | 0 | 0 |
| D-86 | 0.4 | 5 | 5 | 5 | 5 | 5 | 5 | 0 | 1 | 0 | 0 | 0 |
| D-87 | 1.6 | 2 | 2 | 4 | 5 | 3 | 5 | 0 | 0 | 0 | 0 | 0 |
| D-88 | 0.4 | 1 | 2 | 5 | 5 | 5 | 5 | 0 | 0 | 0 | 0 | 0 |
| D-89 | 0.1 | 2 | 4 | 5 | 5 | 5 | 5 | 0 | 0 | 0 | 0 | 0 |
| D-90 | 1.6 | 5 | 5 | 5 | 5 | 5 | 5 | 0 | 0 | 0 | 0 | 0 |
| D-91 | 0.4 | 5 | 5 | 5 | 5 | 5 | 5 | 1 | 1 | 0 | 1 | 1 |
| D-92 | 0.4 | 3 | 1 | 5 | 5 | 5 | 5 | 0 | 0 | 0 | 0 | 1 |
| D-93 | 1.6 | 5 | 5 | 5 | 5 | 5 | 5 | 0 | 0 | 0 | 0 | 0 |
| D-94 | 1.6 | 2 | 5 | 5 | 5 | 5 | 5 | 1 | 0 | 1 | 0 | 0 |
| D-95 | 6.3 | 2 | 5 | 5 | 5 | 5 | 5 | 1 | 0 | 0 | 0 | 5 |
| D-96 | 1.6 | 5 | 5 | 5 | 5 | 5 | 5 | 2 | 0 | 2 | 2 | 2 |
| D-97 | 0.4 | 5 | 5 | 5 | 5 | 5 | 5 | 0 | 0 | 0 | 0 | 3 |
| D-98 | 0.4 | 5 | 5 | 5 | 5 | 5 | 5 | 0 | 0 | 0 | 0 | 1 |

TABLE 4

| Compound No. | Dose (g/a) | N | M | K | H | D | I | R | T | W | S | C | B |
|---|---|---|---|---|---|---|---|---|---|---|---|---|---|
| D-1 | 0.4 | 2 | 1 | 5 | 5 | 5 | 5 | 1 | 1 | 0 | 4 | 5 | 5 |
| D-2 | 0.4 | 2 | 1 | 5 | 5 | 3 | 2 | 0 | 2 | 0 | 3 | 4 | 5 |
| D-3 | 0.4 | 2 | 1 | 5 | 5 | 5 | 5 | 0 | 1 | 0 | 3 | 5 | 5 |
| D-4 | 0.4 | 4 | 5 | 5 | 5 | 5 | 5 | 1 | 3 | 0 | 5 | 5 | 5 |
| D-5 | 0.4 | 2 | 3 | 5 | 5 | 5 | 5 | 1 | 2 | 0 | 4 | 4 | 5 |
| D-6 | 0.4 | 2 | 3 | 5 | 5 | 5 | 5 | 1 | 1 | 0 | 4 | 5 | 5 |
| D-7 | 0.4 | 3 | 3 | 5 | 5 | 5 | 5 | 2 | 2 | 0 | 5 | 5 | 5 |
| D-8 | 0.4 | 2 | 1 | 5 | 5 | 5 | 5 | 0 | 0 | 0 | 3 | 5 | 5 |
| D-9 | 0.4 | 2 | 3 | 5 | 5 | 5 | 5 | 1 | 2 | 0 | 3 | 4 | 5 |
| D-10 | 0.4 | 2 | 2 | 5 | 5 | 5 | 5 | 0 | 0 | 0 | 2 | 5 | 5 |
| D-11 | 0.4 | 3 | 3 | 5 | 5 | 5 | 4 | 1 | 2 | 1 | 4 | 4 | 4 |
| D-12 | 0.1 | 4 | 3 | 5 | 5 | 5 | 5 | 0 | 2 | 0 | 3 | 4 | 5 |
| D-13 | 0.4 | 2 | 1 | 5 | 5 | 5 | 4 | 0 | 2 | 1 | 2 | 5 | 5 |
| D-14 | 0.1 | 3 | 2 | 5 | 5 | 5 | 5 | 1 | 2 | 1 | 5 | 5 | 5 |
| D-15 | 0.4 | 2 | 3 | 5 | 5 | 5 | 5 | 1 | 2 | 0 | 5 | 5 | 5 |
| D-16 | 0.1 | 2 | 2 | 4 | 5 | 5 | 2 | 1 | 1 | 0 | 2 | 5 | 5 |
| D-17 | 1.6 | 1 | 2 | 1 | 5 | 5 | 5 | 0 | 0 | 0 | 3 | 2 | 3 |
| D-18 | 0.4 | 2 | 2 | 5 | 5 | 5 | 5 | 0 | 0 | 0 | 3 | 5 | 5 |
| D-19 | 1.6 | 4 | 2 | 5 | 5 | 5 | 5 | 0 | 1 | 2 | 4 | 5 | 4 |
| D-20 | 0.4 | 3 | 4 | 5 | 5 | 5 | 5 | 2 | 3 | 1 | 3 | 4 | 4 |
| D-21 | 0.4 | 2 | 2 | 2 | 5 | 5 | 3 | 0 | 0 | 0 | 3 | 2 | 3 |
| D-22 | 0.1 | 2 | 3 | 5 | 5 | 5 | 5 | 1 | 2 | 0 | 5 | 5 | 5 |
| D-23 | 0.1 | 2 | 5 | 5 | 5 | 5 | 5 | 1 | 2 | 0 | 5 | 5 | 5 |
| D-24 | 0.1 | 2 | 3 | 5 | 5 | 5 | 4 | 1 | 1 | 2 | 4 | 5 | 5 |
| D-25 | 0.1 | 2 | 4 | 5 | 5 | 5 | 4 | 1 | 2 | 1 | 4 | 5 | 5 |
| D-26 | 0.1 | 2 | 3 | 5 | 5 | 5 | 4 | 1 | 1 | 0 | 4 | 5 | 5 |
| D-27 | 0.1 | 3 | 3 | 5 | 5 | 5 | 4 | 1 | 1 | 1 | 5 | 5 | 5 |
| D-28 | 0.1 | 2 | 3 | 5 | 5 | 5 | 5 | 1 | 1 | 0 | 5 | 5 | 5 |
| D-29 | 0.4 | 2 | 3 | 5 | 5 | 5 | 5 | 0 | 0 | 0 | 2 | 4 | 3 |
| D-30 | 0.4 | 4 | 3 | 5 | 5 | 5 | 5 | 1 | 1 | 0 | 4 | 5 | 5 |
| D-31 | 0.4 | 3 | 2 | 5 | 5 | 5 | 5 | 0 | 1 | 0 | 3 | 5 | 5 |
| D-32 | 0.4 | 2 | 2 | 5 | 5 | 5 | 5 | 0 | 1 | 0 | 2 | 5 | 4 |
| D-33 | 1.6 | 4 | 2 | 2 | 5 | 5 | 5 | 1 | 0 | 0 | 4 | 5 | 5 |
| D-34 | 1.6 | 2 | 2 | 5 | 5 | 5 | 5 | 1 | 2 | 1 | 4 | 5 | 5 |
| D-35 | 0.4 | 2 | 3 | 5 | 5 | 5 | 5 | 0 | 0 | 0 | 3 | 2 | 2 |
| D-36 | 0.4 | 2 | 2 | 5 | 5 | 5 | 3 | 0 | 0 | 0 | 3 | 5 | 3 |
| D-37 | 0.4 | 2 | 3 | 5 | 5 | 5 | 2 | 0 | 0 | 0 | 3 | 5 | 5 |
| D-38 | 0.4 | 2 | 2 | 5 | 5 | 5 | 4 | 0 | 1 | 0 | 4 | 5 | 5 |
| D-39 | 1.6 | 3 | 4 | 5 | 5 | 5 | 5 | 0 | 2 | 0 | 5 | 5 | 5 |
| D-40 | 1.6 | 2 | 3 | 5 | 5 | 5 | 5 | 0 | 2 | 1 | 4 | 5 | 5 |
| D-41 | 0.4 | 3 | 4 | 2 | 5 | 5 | 5 | 1 | 3 | 0 | 5 | 4 | 3 |
| D-42 | 1.6 | 2 | 2 | 5 | 5 | 5 | 5 | 0 | 1 | 0 | 2 | 4 | 3 |
| D-43 | 1.6 | 3 | 2 | 5 | 5 | 5 | 4 | 1 | 1 | 0 | 2 | 5 | 5 |
| D-44 | 0.4 | 1 | 2 | 2 | 5 | 5 | 5 | 0 | 0 | 0 | 2 | 3 | 3 |
| D-48 | 0.4 | 1 | 1 | 5 | 5 | 5 | 5 | 0 | 0 | 0 | 2 | 5 | 5 |
| D-49 | 0.4 | 2 | 1 | 5 | 5 | 5 | 5 | 1 | 2 | 1 | 5 | 5 | 5 |
| D-50 | 0.4 | 2 | 1 | 5 | 5 | 5 | 5 | 2 | 2 | 1 | 4 | 5 | 5 |
| D-51 | 0.4 | 5 | 2 | 5 | 5 | 5 | 5 | 1 | 4 | 4 | 5 | 5 | 5 |
| D-52 | 0.4 | 4 | 2 | 5 | 5 | 5 | 5 | 1 | 3 | 1 | 5 | 5 | 5 |
| D-53 | 0.4 | 5 | 2 | 5 | 5 | 5 | 5 | 1 | 3 | 1 | 5 | 5 | 5 |
| D-54 | 0.4 | 2 | 1 | 5 | 5 | 5 | 5 | 1 | 3 | 1 | 5 | 5 | 5 |
| D-56 | 0.4 | 1 | 1 | 5 | 5 | 5 | 2 | 0 | 0 | 0 | 3 | 5 | 5 |
| D-57 | 1.6 | 1 | 1 | 5 | 5 | 5 | 5 | 0 | 1 | 1 | 1 | 5 | 4 |

TABLE 4-continued

| Compound No. | Dose (g/a) | N | M | K | H | D | I | R | T | W | S | C | B |
|---|---|---|---|---|---|---|---|---|---|---|---|---|---|
| D-58 | 0.4 | 2 | 4 | 5 | 5 | 5 | 5 | 0 | 1 | 1 | 4 | 5 | 5 |
| D-59 | 1.6 | 3 | 4 | 5 | 5 | 5 | 5 | 2 | 2 | 1 | 5 | 5 | 5 |
| D-60 | 1.6 | 2 | 3 | 5 | 5 | 4 | 3 | 1 | 2 | 1 | 5 | 5 | 5 |
| D-61 | 0.1 | 2 | 1 | 5 | 5 | 5 | 5 | 2 | 3 | 2 | 3 | 5 | 5 |
| D-62 | 0.4 | 2 | 1 | 5 | 5 | 5 | 5 | 1 | 2 | 1 | 5 | 5 | 5 |
| D-63 | 0.4 | 2 | 2 | 5 | 5 | 5 | 5 | 1 | 2 | 1 | 3 | 5 | 2 |
| D-64 | 0.4 | 2 | 1 | 5 | 5 | 5 | 5 | 1 | 3 | 1 | 4 | 5 | 4 |
| D-65 | 0.4 | 2 | 1 | 5 | 5 | 5 | 5 | 1 | 3 | 2 | 5 | 5 | 5 |
| D-66 | 0.1 | 3 | 2 | 5 | 5 | 5 | 5 | 1 | 2 | 0 | 5 | 3 | 5 |
| D-67 | 0.1 | 1 | 1 | 5 | 5 | 5 | 5 | 0 | 2 | 1 | 4 | 5 | 5 |
| D-68 | 0.4 | 3 | 1 | 2 | 5 | 5 | 5 | 0 | 0 | 0 | 3 | 3 | 2 |
| D-69 | 0.4 | 4 | 0 | 2 | 5 | 5 | 5 | 1 | 3 | 3 | 5 | 5 | 1 |
| D-70 | 1.6 | 1 | 1 | 2 | 5 | 5 | 5 | 1 | 3 | 0 | 1 | 2 | 1 |
| D-71 | 1.6 | 0 | 0 | 2 | 5 | 5 | 5 | 0 | 2 | 0 | 4 | 3 | 1 |
| D-72 | 1.6 | 2 | 0 | 2 | 5 | 5 | 4 | 1 | 1 | 0 | 3 | 3 | 1 |
| D-73 | 1.6 | 3 | 0 | 2 | 5 | 5 | 5 | 1 | 2 | 1 | 3 | 3 | 3 |
| D-74 | 0.4 | 2 | 0 | 1 | 5 | 5 | 5 | 1 | 1 | 1 | 3 | 3 | 2 |
| D-75 | 1.6 | 4 | 0 | 0 | 5 | 4 | 4 | 1 | 3 | 1 | 3 | 3 | 0 |
| D-76 | 0.4 | 2 | 0 | 1 | 5 | 5 | 5 | 0 | 2 | 0 | 2 | 4 | 0 |
| D-77 | 0.4 | 3 | 0 | 2 | 5 | 5 | 5 | 0 | 2 | 0 | 5 | 3 | 2 |
| D-78 | 0.4 | 3 | 0 | 2 | 5 | 5 | 5 | 1 | 3 | 1 | 3 | 3 | 2 |
| D-79 | 1.6 | 5 | 1 | 5 | 5 | 5 | 5 | 2 | 4 | 1 | 4 | 5 | 2 |
| D-80 | 0.4 | 4 | 0 | 3 | 5 | 5 | 5 | 1 | 2 | 0 | 3 | 3 | 1 |
| D-81 | 1.6 | 1 | 0 | 1 | 5 | 5 | 5 | 1 | 1 | 0 | 3 | 3 | 1 |
| D-82 | 0.4 | 4 | 1 | 2 | 5 | 5 | 4 | 2 | 3 | 1 | 4 | 3 | 1 |
| D-83 | 1.6 | 1 | 1 | 3 | 5 | 5 | 5 | 1 | 2 | 0 | 4 | 4 | 1 |
| D-84 | 1.6 | 2 | 1 | 0 | 5 | 5 | 5 | 3 | 1 | 1 | 2 | 3 | 2 |
| D-85 | 1.6 | 0 | 0 | 0 | 5 | 4 | 5 | 0 | 0 | 0 | 1 | 0 | 0 |
| D-86 | 0.4 | 1 | 0 | 1 | 5 | 4 | 3 | 0 | 2 | 0 | 1 | 2 | 0 |
| D-87 | 1.6 | 0 | 0 | 1 | 5 | 4 | 5 | 0 | 1 | 0 | 0 | 1 | 0 |
| D-88 | 0.4 | 1 | 1 | 4 | 5 | 5 | 5 | 0 | 0 | 0 | 2 | 2 | 2 |
| D-89 | 0.1 | 2 | 1 | 4 | 5 | 5 | 5 | 0 | 0 | 0 | 4 | 3 | 2 |
| D-90 | 1.6 | 1 | 1 | 2 | 5 | 5 | 5 | 1 | 1 | 0 | 3 | 3 | 3 |
| D-91 | 0.4 | 4 | 1 | 2 | 5 | 5 | 5 | 1 | 1 | 0 | 4 | 3 | 2 |
| D-92 | 0.4 | 1 | 1 | 2 | 5 | 5 | 5 | 0 | 1 | 0 | 2 | 5 | 2 |
| D-93 | 1.6 | 1 | 1 | 1 | 5 | 5 | 5 | 0 | 0 | 0 | 3 | 3 | 3 |
| D-94 | 1.6 | 2 | 3 | 3 | 5 | 5 | 5 | 1 | 1 | 2 | 3 | 5 | 0 |
| D-95 | 6.3 | 2 | 1 | 3 | 5 | 5 | 5 | 0 | 0 | 0 | 2 | 5 | 2 |
| D-96 | 1.6 | 5 | 2 | 5 | 5 | 5 | 5 | 2 | 0 | 2 | 3 | 5 | 3 |
| D-97 | 0.4 | 5 | 2 | 5 | 5 | 5 | 5 | 5 | 0 | 4 | 5 | 5 | 5 |
| D-98 | 0.4 | 5 | 3 | 5 | 5 | 5 | 5 | 5 | 0 | 5 | 4 | 5 | 5 |

TABLE 5

| Compound No. | Dose (g/a) | N | a | b | c | d | e | f |
|---|---|---|---|---|---|---|---|---|
| D-31 | 0.4 | 5 | 5 | 5 | 5 | 4 | 5 | 0 |
| D-53 | 0.4 | 5 | 5 | 5 | 5 | 4 | 5 | 0 |
| D-54 | 0.4 | 5 | 5 | 5 | 5 | 5 | 5 | 0 |
| D-61 | 0.4 | 5 | 5 | 5 | 5 | 5 | 5 | 0 |
| D-62 | 0.4 | 5 | 5 | 5 | 5 | 5 | 5 | 0 |
| D-63 | 0.4 | 5 | 5 | 5 | 5 | 5 | 5 | 0 |
| D-64 | 0.4 | 5 | 5 | 5 | 5 | 5 | 5 | 0 |
| D-65 | 0.4 | 5 | 5 | 5 | 5 | 5 | 5 | 0 |
| D-66 | 0.4 | 5 | 5 | 5 | 5 | 5 | 5 | 0 |
| D-67 | 0.4 | 5 | 5 | 5 | 5 | 5 | 5 | 0 |
| D-69 | 0.4 | 5 | 5 | 5 | 5 | 5 | 5 | 0 |
| D-70 | 0.4 | 5 | 5 | 5 | 5 | 4 | 5 | 0 |
| D-76 | 0.4 | 5 | 5 | 5 | 5 | 4 | 5 | 0 |
| D-77 | 0.4 | 5 | 5 | 5 | 5 | 5 | 5 | 0 |
| D-80 | 0.4 | 5 | 4 | 5 | 5 | 5 | 5 | 0 |
| D-82 | 0.4 | 5 | 5 | 5 | 5 | 5 | 4 | 0 |
| D-89 | 0.4 | 5 | 5 | 5 | 5 | 5 | 5 | 0 |
| D-91 | 0.4 | 5 | 5 | 5 | 5 | 5 | 4 | 0 |
| D-96 | 0.4 | 5 | 5 | 5 | 5 | 5 | 4 | 0 |

Utilizability in Industry

The uracil derivative represented by the formula (I) of the present invention can be used for important crops with safety and shows high herbicidal effect against many weeds with low dose, and is available as an active ingredient for a selective herbicide.

We claim:

1. An uracil derivative, which is represented by the formula (1):

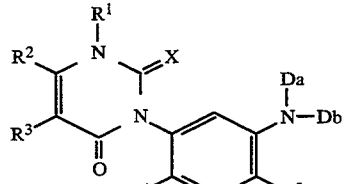

in which
$R^1$ represents a hydrogen atom, a $C_1$ to $C_3$ alkyl group or a $C_1$ to $C_3$ haloalkyl group;
$R^2$ represents a $C_1$ to $C_6$ haloalkyl group;
$R^3$ represents a hydrogen atom, a $C_1$ to $C_6$ alkyl group, a $C_1$ to $C_6$ haloalkyl group, a hydroxymethyl group, a halogen atom or a nitro group;
$R^4$ represents a hydrogen atom or a halogen atom;
$R^5$ represents a hydrogen atom, a halogen atom, a nitro group or a cyano group;
X represents an oxygen atom or a sulfur atom;
$D_a$ and $D_b$ each independently represents a hydrogen atom, a $C_1$ to $C_8$ alkyl group, a $C_1$ to $C_6$ haloalkyl group, a $C_3$ to $C_8$ cycloalkyl group, a $C_3$ to $C_8$ cycloalkyl($C_1$ to $C_4$)alkyl group, a $C_2$ to $C_8$ alkenyl group, a $C_3$ to $C_8$ alkynyl group, a $C_2$ to $C_8$ haloalkenyl group, a $C_3$ to $C_8$ haloalkynyl group, a $C_3$ to $C_8$ halocycloalkyl group, a $C_3$ to $C_8$ halocycloalkyl($C_1$ to $C_4$)alkyl group, $CH(OH)CCl_3$, Ar in which Ar represents a phenyl group or a naphthyl group each of which may be substituted by one or two or more substituents and the substituent may be selected from a $C_1$ to $C_4$ alkyl group, a $C_3$ to $C_6$ cycloalkyl group, a $C_1$ to $C_4$ haloalkyl group, a $C_3$ to $C_6$ halocycloalkyl group, a halogen atom, a cyano group, a nitro group, a hydroxy group, a $C_1$ to $C_4$ alkoxy group, a $C_1$ to $C_4$ haloalkoxy group, a $C_1$ to $C_4$ alkylcarbonyl group, a carboxyl group, a $C_1$ to $C_4$ alkoxycarbonyl group, an amino group, a $C_1$ to $C_4$ alkylamino group, an acetamino group, a N,N-dimethylamino group and a methanesulfonyl group, —$L^1$—Ar in which Ar has the same meaning as above, and $L^1$ represents a $C_1$ to $C_6$ alkyl chain, a $C_2$ to $C_6$ alkenyl chain or a $C_2$ to $C_6$ alkynyl chain each of which may be branched, Het in which Her represents a 5-membered heterocyclic residue, a 6-membered heterocyclic residue or a fused heterocyclic residue each of which contains, as a ring constituent atom, at least one atom selected from a sulfur atom, an oxygen atom and a nitrogen atom and may be substituted by one or two or more substituents, and the substituent may be selected from a $C_1$ to $C_4$ alkyl group, a $C_3$ to $C_6$ cycloalkyl group, a $C_1$ to $C_4$ haloalkyl group, a $C_3$ to $C_6$ halocycloalkyl group, a halogen atom, a cyano group, a nitro group, a hydroxy group, a $C_1$ to $C_4$ alkoxy group, a $C_1$ to $C_4$ haloalkoxy group, a $C_1$ to $C_4$ alkylcarbonyl group, a carboxyl group, a $C_1$ to $C_4$ alkoxycarbonyl group, an amino group, a $C_1$ to $C_4$ alkylamino group, an acetamino group, a N,N-dimethylamino group and a methanesulfonyl group, —$L^1$—Het in which Het and $L^1$ have the same meanings as above, —$L^2$—$D^{52}$ in which $D^{52}$ represents a hydrogen atom, a $C_1$ to $C_{20}$ alkyl group, a $C_1$ to $C_{20}$ haloalkyl group, a $C_3$ to $C_8$ cycloalkyl group, a $C_3$ to $C_8$ cycloalkyl($C_1$ to $C_4$)alkyl group, a $C_2$ to $C_8$ alkenyl group, a $C_3$ to $C_8$ alkynyl group, a $C_2$ to $C_8$ haloalkenyl group, a $C_3$ to $C_8$ haloalkynyl group, a $C_3$ to $C_8$ halocycloalkyl group, a $C_3$ to $C_8$ halocycloalkyl ($C_1$ to $C_4$)alkyl group, a $C_1$ to $C_4$ alkoxy($C_1$ to $C_4$)alkyl group, Ar (Ar has the same meaning as above), —$L^1$—Ar group (Ar and $L^1$ have the same meanings as above), Het (Het has the same meaning as above)or —$L^1$—Het (Het and $L^1$ have the same meanings as above), and $L^2$ represents —(O)—, —C(S)—, —$SO_2$—, —S(O)—, —S—, —O—, —C(O)O—, —C(O)S—, —C(S)O—, —C(S)S— or —C(O)C-(O)O—, —$L^3$—O—$D^{52}$ in which $D^{52}$ has the same meaning as above, and $L^3$ represents a $C_1$ to $C_6$ alkyl chain, a $C_2$ to $C_6$ alkenyl chain or a $C_2$ to $C_6$ alkynyl chain each of which may be substituted by one or two or more substituents and may be branched and the substituent may be selected from a $C_1$ to $C_4$ alkyloxycarbonyl group, a $C_1$ to $C_4$ haloalkyl group, a $C_1$ to $C_4$ alkoxy($C_1$ to $C_4$)alkyl group, a $C_1$ to $C_4$ alkylthio group, Ar (Ar has the same meaning as above), —$L^1$—Ar group (Ar and $L^1$ have the same meanings as above), Het (Het has the same meaning as above- )and —$L^1$—Het (Het and $L^1$ have the same meanings as above), —$L^3$—S—$D^{52}$ in which $D^{52}$ and $L^3$ have the same meanings as above, —$L^3$—(O)—$D^{52}$ in which $D^{52}$ and $L^3$ have the same meanings as above, —$L^3$—C(S)—$D^{52}$ in which $D^{52}$ and $L^3$ have the same meanings as above, —$L^3$—C(O)O—$D^{52}$ in which $D^{52}$ and $L^3$ have the same meanings as above, —O—$L^3$—C(O)O—$D^{52}$ in which $D^{52}$ and $L^3$ have the same meanings as above, —$L^3$—C(O)S—$D^{52}$ in which $D^{52}$ and $L^3$ have the same meaning as above, —O—$L^3$—C(O)S—$D^{52}$ in which $D^{52}$ and $L^3$ have the same meanings as above, —(O)—$ND^{52}D^{53}$ in which $D^{52}$ has the same meaning as above, and $D^{53}$ represents a hydrogen atom, a $C_1$ to $C_8$ alkyl group, a $C_1$ to $C_8$ haloalkyl group, a $C_1$ to $C_6$ alkoxy group, a $C_1$ to $C_6$ alkylcarbonyl group, a $C_1$ to $C_6$ haloalkylcarbonyl group, a $C_1$ to $C_6$ alkoxycarbonyl group, a $C_1$ to $C_6$ alkylsulfonyl group, a $C_1$ to $C_6$ haloalkylsulfonyl group, Ar (Ar has the same meaning as above), —$L^1$—Ar group (Ar and $L^1$ have the same meanings as above), —(O)—Ar (Ar has the same meaning as above), —C(O)—Ar (Ar has the same meaning as above)or —$SO_2$—Ar (Ar has the same meaning as above), and alternatively $D^{52}$ and $D^{53}$ together with a nitrogen atom to which they are attached may form a 5- to 7-membered ring, and ring constituent atoms are selected from a carbon atom, a nitrogen atom, an oxygen atom and a sulfur atom, —C(S)—$ND^{52}D^{53}$ in which $D^{52}$ and $D^{53}$ have the same meanings as above, —$L^3$—C(O)—$ND^{52}D^{53}$ in which $D^{52}$, $D^{53}$ and $L^3$ have the same meanings as above, —$L^3$—C(S)—$ND^{52}D^{53}$ in which $D^{52}$, $D^{53}$ and $L^3$ have the same meanings as above, —$SO_2$—$ND^{52}D^{53}$ in which $D^{52}$ and $D^{53}$ have the same meanings as above, —$SO_2O$—$D^{53}$ in which $D^{53}$ has the same meaning as above, —$SO_2O$—$Si(CH_3)_3$, —$SO_2$—$L^1$—$Si(CH_3)_3$ in which $L^1$ has the same meaning as above,

—$SO_2CH_2SO_2CH_3$,

—$P(O)(OD^{52})(OD^{53})$ in which $D^{52}$ and $D^{53}$ have the same meanings as above, —$P(O)(OD^{52})(SD^{53})$ in which $D^{52}$ and $D^{53}$ have the same meanings as above, —$P(O)(OD^{52})D^{53}$ in which $D^{52}$ and $D^{53}$ have the same meanings as above, —$P(O)(SD^{52})D^{53}$ in which $D^{52}$ and $D^{53}$ have the same meanings as above, —$P(S)(OD^{52})(OD^{53})$ in which $D^{52}$ and $D^{53}$ have the same meanings as above, —$P(S)(OD^{52})(SD^{53})$ in which $D^{52}$ and $D^{53}$ have the same meanings as above, —$P(S)(OD^{52})D^{53}$ in which $D^{52}$ and $D^{53}$ have the same meanings as above, —$P(S)(SD^{52})D^{53}$ in which $D^{52}$ and $D^{53}$ have the same meanings as above, —$L^3$—$P(O)(OD^{52})(OD^{53})$ in which $D^{52}$, $D^{53}$ and $L^3$ have the same meanings as above, —$L^3$—$P(O)(OD^{52})(SD^{53})$ in which $D^{52}$, $D^{53}$ and $L^3$ have the same meanings as above, —$L^3$—P(O)(OD$^{52}$)D$^{53}$ in which D$^{52}$, D$^{53}$ and L$^3$ have the same meanings as above, —$L^3$—P(O)(SD$^{52}$)D$^{53}$ in which D$^{52}$, D$^{53}$ and L$^3$ have the same meanings as above, —$L^3$—P(S)(OD$^{52}$)(OD$^{53}$)in which D$^{52}$, D$^{53}$ and L$^3$ have the same meanings as above, —$L^3$P—P(S)(OD$^{52}$)(SD$^{53}$)in which D$^{52}$, D$^{53}$ and L$^3$ have the same meanings as above, —$L^3$—P(S)(OD$^{52}$)D$^{53}$ in which D$^{52}$, D$^{53}$ and L$^3$ have the same meanings as above, —$L^3$—P(S)(SD$^{52}$)D$^{53}$ in which D$^{52}$, D$^{53}$ and L$^3$ have the same meanings as above, —C(D$^{53}$)(P(O)(OD$^{52}$)$_2$)$_2$ in which D$^{52}$ and D$^{53}$ have the same meanings as above, =CD$^{52}$D$^{54}$ in which D$^{52}$ has the same meaning as above, and D$^{54}$ represents a hydrogen atom, a halogen atom, a $C_1$ to $C_6$ alkyl group, a $C_1$ to $C_6$ alkoxy group, a $C_1$ to $C_6$ alkylthio group or Ar (Ar has the same meaning as above), —$L^3$—CN in which $L^3$ has the same meaning as above, —ND$^{52}$D$^{53}$ in which D$^{52}$ and D$^{53}$ have the same meanings as above, —CH=N—O—D$^{52}$ in which D$^{52}$ has the same meaning as above, =CD$^{54}$—ND$^{52}$D$^{53}$ in which D$^{52}$, D$^{53}$ and D$^{54}$ have the same meanings as above, —$L^2$—D$^{55}$ in which $L^2$ has the same meaning as above, and D$^{55}$ represents a $C_1$ to $C_6$ alkyl group, a $C_2$ to $C_6$ alkenyl group or a $C_2$ to $C_6$ alkynyl group each of which may be substituted by one or two or more of a $C_1$ to $C_6$ haloalkyl group or one or two or more of a $C_1$ to $C_4$ alkyloxycarbonyl group and may be branched, or —$L^1$—SO$_2$—D$^{56}$ in which $L^1$ has the same meaning as above, and D$^{56}$ represents a $C_1$ to $C_6$ alkyl group; and alternatively $D_a$ and $D_b$ may form a 3- to 8-membered ring and the ring constituent atoms are selected from a carbon atom, a nitrogen atom, an oxygen atom, a sulfur atom and a phosphorus atom, and the ring may be substituted by one or two or more of a substituent, and the substituent may be selected from a $C_1$ to $C_4$ alkyl group, a $C_3$ to $C_6$ cycloalkyl group, a $C_1$ to $C_4$ haloalkyl group, a $C_3$ to $C_6$ halocycloalkyl group, a halogen atom, a cyano group, a nitro group, a hydroxy group, a $C_1$ to $C_4$ alkoxy group, a $C_1$ to $C_4$ haloalkoxy group, a $C_1$ to $C_4$ alkylcarbonyl group, a carboxyl group, a $C_1$ to $C_4$ alkoxycarbonyl group, an amino group, a $C_1$ to $C_4$ alkylamino group, an acetamino group, a N,N-dimethylamino group and a methanesulfonyl group:

provided that except for the case where $D_a$ and $D_b$ both represent hydrogen atoms, the case where $D_a$ represents —$L^2$—D$^{52}$ ($L^2$ represents —SO$_2$—, and D$^{52}$ represents the $C_1$ to $C_4$ alkyl group or the $C_1$ to $C_3$ haloalkyl group) and $D_b$ represents the hydrogen atom, the $C_1$ to $C_4$ alkyl group, the $C_2$ to $C_5$ alkenyl group, the $C_3$ to $C_5$ alkynyl group, the $C_2$ to $C_5$ acyl group, the $C_1$ to $C_4$ alkylsulfonyl group or the ($C_1$ to $C_3$ alkoxy) $C_1$ to $C_2$ alkyl group are excluded.

2. An uracil derivative according to claim 1, which is represented by the formula (1):

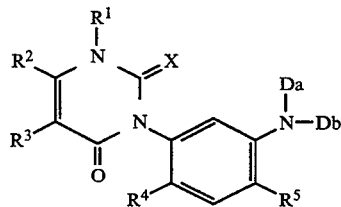

in which
$R^1$ represents a methyl group;
$R^2$ represents a trifluoromethyl group;
$R^3$ represents a hydrogen atom;
$R^4$ represents a hydrogen atom or a halogen atom;
$R^5$ represents a halogen atom;
X represents an oxygen atom;
$D_a$ and $D_b$ each independently represents a hydrogen atom, a $C_1$ to $C_6$ alkyl group, a $C_3$ to $C_6$ alkenyl group, a $C_3$ to $C_6$ alkynyl group, —$L^1$—Ar in which $L^1$ represents a $C_1$ to $C_6$ alkyl chain, a $C_2$ to $C_6$ alkenyl chain or a $C_2$ to $C_6$ alkynyl chain each of which may be branched, and Ar represents a phenyl group or a naphthyl group each of which may be substituted by one or two or more of a substituent, and the substituent may be selected from a $C_1$ to $C_4$ alkyl group, a $C_1$ to $C_4$ haloalkyl group, a halogen atom, a nitro group, a $C_1$ to $C_4$ alkoxy group and a $C_1$ to $C_4$ alkoxycarbonyl group, Het in which Het represents a pyridine ring, a thiophene ring and a furan ring, —$L^1$—Het in which Het and $L^1$ have the same meanings as above, —$L^2$—D$^{52}$ in which D$^{52}$ represents a hydrogen atom, a $C_1$ to $C_6$ alkyl group, a $C_1$ to $C_6$ haloalkyl group, a $C_3$ to $C_8$ cycloalkyl group, a $C_3$ to $C_8$ cycloalkyl($C_1$ to $C_2$)alkyl group, a $C_3$ to $C_6$ alkenyl group, a $C_3$ to $C_6$ alkynyl group, a $C_1$ to $C_4$ alkoxy($C_1$ to $C_4$)alkyl group, Ar (Ar has the same meaning as above), —$L^1$—Ar (Ar and $L^1$ have the same meanings as above), Het (Het has the same meaning as above) or —$L^1$—Het (Het and $L^1$ have the same meanings as above), and $L^2$ represents —C(O)—, —C(S)—, —SO$_2$—, —S(O)—, —S—, —C(O)O—, —C(O)S—, —C(S)O—, —C(S)S— or —C(O)C(O)O—, —$L^3$—O—D$^{52}$ in which D$^{52}$ has the same meaning as above, and $L^3$ represents a $C_1$ to $C_6$ alkyl chain, a $C_2$ to $C_6$ alkenyl chain or a $C_2$ to $C_6$ alkynyl chain each of which may be substituted by one or more of a $C_1$ to $C_4$ haloalkyl group or a $C_1$ to $C_4$ alkyloxycarbonyl group and may be branched, —$L^3$—C(O)O—D$^{52}$ in which D$^{52}$ and $L^3$ have the same meanings as above, —C(O)—ND$^{52}$D$^{53}$ in which D$^{52}$ has the same meaning as above, and D$^{53}$ represents a hydrogen atom, a $C_1$ to $C_6$ alkyl group, a $C_1$ to $C_6$ alkoxy group, a $C_1$ to $C_4$ alkylsulfonyl group, Ar (Ar has the same meaning as above) or —$L^1$—Ar group (Ar and $L^1$ have the same meanings as above), and alternatively D$^{52}$ and D$^{53}$ together with a nitrogen atom to which they are attached may form a 5- or 6-membered ring, —C(S)—ND$^{52}$D$^{53}$ in which D$^{52}$ and D$^{53}$ have the same meanings as above, —L³—C(O)—ND⁵²D⁵³ in which D⁵², D⁵³ and L³ have the same meanings as above, —L³—C(S)—ND⁵²D⁵³ in which D⁵², D⁵³ and L³ have the same meanings as above, —P(O)(OD⁵²)(OD⁵³) in which D⁵² and D⁵³ have the same meanings as above, —L³—P(O)(OD⁵²)(OD⁵³) in which D⁵², D⁵³ and L³ have the same meanings as above, —L³—CN in which L³ has the same meaning as above, =CD⁵⁴—ND⁵²D⁵³ in which D⁵² and D⁵³ have the same meanings as above, and D⁵⁴ represents a hydrogen atom, a halogen atom, a $C_1$ to $C_6$ alkyl group, a $C_1$ to $C_6$ alkoxy group, a $C_1$ to $C_4$ alkylthio group or Ar (Ar has the same meaning as above), —L²—D⁵⁵ in which L² has the same meaning as above, and D⁵⁵ represents a $C_1$ to $C_6$ alkyl group, a $C_2$ to $C_6$ alkenyl group or a $C_2$ to $C_6$ alkynyl group each of which may be substituted by one or two or more of a $C_1$ to $C_4$ haloalkyl group or one or two or more of a $C_1$ to $C_4$ alkyloxycarbonyl group and may be branched, or —L¹—SO₂—D⁵⁶ in which L¹ has the same meaning as above, and D⁵⁶ represents a $C_1$ to $C_4$ alkyl group;

and alternatively $D_a$ and $D_b$ together with a nitrogen atom to which they are attached may form a ring represented by

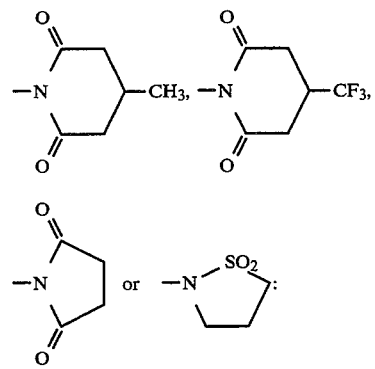

provided that except for the case where $D_a$ and $D_b$ both represent hydrogen atoms, the case where $D_a$ represents —L²—D⁵² (L² represents —SO₂—, and D⁵² represents the $C_1$ to $C_4$ alkyl group or the $C_1$ to $C_3$ haloalkyl group), and $D_b$ represents a hydrogen atom, a $C_1$ to $C_4$ alkyl group, a $C_2$ to $C_5$ alkenyl group, a $C_3$ to $C_5$ alkynyl group, a $C_2$ to $C_5$ acyl group, a $C_1$ to $C_4$ alkylsulfonyl group or a ($C_1$ to $C_3$ alkoxy) $C_1$ to $C_2$ alkyl group are excluded.

3. A herbicide comprising the uracil derivative as defined in claim 1 as an effective ingredient and a carrier.

4. A herbicide comprising the uracil derivative as defined in claim 2 as an effective ingredient and a carrier.

5. A method for killing weeds and inhibiting their growth which comprises applying the uracil derivative as defined in claim 1 in an amount effective for killing the weeds.

6. A method for killing weeds and inhibiting their growth which comprises applying the uracil derivative as defined in claim 2 in an amount effective for killing the weeds.

* * * * *

UNITED STATES PATENT AND TRADEMARK OFFICE
CERTIFICATE OF CORRECTION

PATENT NO. : 5,356,863
DATED : October 18, 1994
INVENTOR(S) : Jun Satow et al.

It is certified that error appears in the above-identified patent and that said Letters Patent is hereby corrected as shown below:

| COL. | LINE | |
|---|---|---|
| 1, | 28, | delete "21th" and insert --21st--. |
| 2, | 23, | delete "3" and insert --$R^3$--; |
|  | 24, | delete "4" and insert --$R^4$--; |
|  | 25, | delete "5" and insert --$R^5$--. |

UNITED STATES PATENT AND TRADEMARK OFFICE
CERTIFICATE OF CORRECTION

PATENT NO. : 5,356,863
DATED : October 18, 1994
INVENTOR(S) : Jun Satow et al.

It is certified that error appears in the above-identified patent and that said Letters Patent is hereby corrected as shown below:

COL.   LINE 3,   50, delete "studied" and insert -- studying --;

delete between lines 5 and 15, delete

"  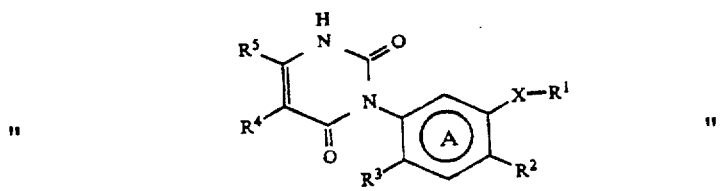  "

and insert

--  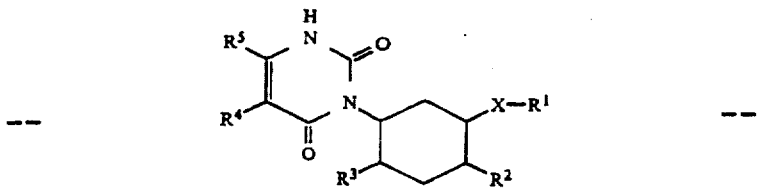  --

.

4,   49, delete "-O$_2$-" and insert -- SO$_2$ --;

62, delete "Her" and insert --Het--.

UNITED STATES PATENT AND TRADEMARK OFFICE
CERTIFICATE OF CORRECTION

PATENT NO. : 5,356,863

DATED : October 18, 1994

INVENTOR(S) : Jun Satow et al.

It is certified that error appears in the above-identified patent and that said Letters Patent is hereby corrected as shown below:

| COL. | LINE | |
|---|---|---|
| 5, | 19, | delete ","; |
| | 21, | delete "-C(O)-AR" and insert -- -C(S)-AR --. |
| 10, | 31, | delete "[2.2.21]" and insert --[2.2.2]--. |
| 12, | 34, | delete "[2.2.21[" and insert --[2.2.2]--. |
| 13, | 54, | insert -- -C(O)S- -- after "-C(O)O-,". |
| 14, | 3, | delete "$L^3C(O)-(O)-D^{52}$" and insert -- $L^3-C(O)-(O)-D^{52}$ --. |
| | 35, | delete "$-L^3-(O)-ND^{52}D^{53}$" and insert -- $-L^3-C-(O)ND^{52}D^{53}$ --. |
| 28, | 38, | insert --)-- after "chlorophenyl". |
| 47, | 48, | delete "tertialy" and insert --tertiarly--. |
| 75, | 20, | delete "Her" and insert --Het--; |
| | 53, | delete " -(O)- " and insert -- -C(O)-. |

UNITED STATES PATENT AND TRADEMARK OFFICE
CERTIFICATE OF CORRECTION

PATENT NO. : 5,356,863
DATED : October 18, 1994
INVENTOR(S) : Jun Satow et al.

It is certified that error appears in the above-identified patent and that said Letters Patent is hereby corrected as shown below:

COL.    LINE 76,     5, delete "-L$^3$-(O)-D$^{52}$" and insert ---L$^3$C(O)-D$^{52}$--;

17, delete "-(O)-ND$^{52}$D$^{53}$" and insert -- -C(O)-ND$^{52}$D$^{53}$ --;

27, delete "-(O)-Ar" and insert -- -C(O)-Ar --;

28, delete "-C(O)-Ar" and insert -- -C(S)-Ar --.

Signed and Sealed this

Nineteenth Day of May, 1998

*Attest:*

*Attesting Officer*

BRUCE LEHMAN

*Commissioner of Patents and Trademarks*